(12) United States Patent
Chang

(10) Patent No.: US 9,057,109 B2
(45) Date of Patent: Jun. 16, 2015

(54) DIAGNOSIS OF MELANOMA AND SOLAR LENTIGO BY NUCLEIC ACID ANALYSIS

(71) Applicant: DermTech International, La Jolla, CA (US)

(72) Inventor: Sherman H. Chang, San Diego, CA (US)

(73) Assignee: DERMTECH INTERNATIONAL, La Jolla, CA (US)

( * ) Notice: Subject to any disclaimer, the term of this patent is extended or adjusted under 35 U.S.C. 154(b) by 0 days.

(21) Appl. No.: 14/199,900

(22) Filed: Mar. 6, 2014

(65) Prior Publication Data

US 2014/0256584 A1 Sep. 11, 2014

Related U.S. Application Data

(63) Continuation of application No. 14/172,784, filed on Feb. 4, 2014, which is a continuation of application No. 12/991,685, filed as application No. PCT/US2009/044035 on May 14, 2009, now abandoned.

(60) Provisional application No. 61/058,149, filed on Jun. 2, 2008, provisional application No. 61/053,988, filed on May 16, 2008, provisional application No. 61/127,731, filed on May 14, 2008.

(51) Int. Cl.
*C12Q 1/68* (2006.01)

(52) U.S. Cl.
CPC ............. *C12Q 1/6886* (2013.01); *C12Q 1/68* (2013.01); *C12Q 2600/112* (2013.01); *C12Q 2600/158* (2013.01); *C12Q 2600/178* (2013.01)

(58) Field of Classification Search
CPC ........................................................ C12Q 1/68
USPC ........................................................ 435/6.1
See application file for complete search history.

(56) References Cited

U.S. PATENT DOCUMENTS

| | | | |
|---|---|---|---|
| 4,365,409 A | 12/1982 | Riley et al. |
| 4,458,066 A | 7/1984 | Caruthers et al. |
| 4,537,776 A | 8/1985 | Cooper |
| 4,683,195 A | 7/1987 | Mullis et al. |
| 4,683,202 A | 7/1987 | Mullis et al. |
| 4,836,217 A | 6/1989 | Fischer et al. |
| 4,851,510 A | 7/1989 | Khan |
| 4,971,800 A | 11/1990 | Chess et al. |
| 5,460,939 A | 10/1995 | Hansborough et al. |
| 5,493,009 A | 2/1996 | Ferrone |
| 5,583,032 A | 12/1996 | Torrence et al. |
| 5,654,286 A | 8/1997 | Hostetler |
| 5,753,612 A | 5/1998 | Mitrani |
| 5,807,522 A | 9/1998 | Brown et al. |
| 5,811,239 A | 9/1998 | Frayne |
| 5,858,683 A | 1/1999 | Keesee |
| 5,962,477 A | 10/1999 | Mak |
| 5,989,815 A | 11/1999 | Skolnick et al. |
| 6,054,277 A | 4/2000 | Furcht et al. |
| 6,056,859 A | 5/2000 | Ramsey et al. |
| 6,129,983 A | 10/2000 | Schumann et al. |
| 6,203,987 B1 | 3/2001 | Friend et al. |
| 6,312,909 B1 | 11/2001 | Shyjan |
| 6,355,439 B1 | 3/2002 | Chung et al. |
| 6,410,019 B1 | 6/2002 | DeSimone et al. |
| 6,410,240 B1 | 6/2002 | Hodge et al. |
| 6,551,799 B2 | 4/2003 | Gurney et al. |
| 6,720,145 B2 | 4/2004 | Rheins et al. |
| 6,726,971 B1 | 4/2004 | Wong |
| 6,891,022 B1 | 5/2005 | Steward et al. |
| 6,949,338 B2 | 9/2005 | Rheins et al. |
| 7,183,057 B2 | 2/2007 | Benson |
| 7,247,426 B2 | 7/2007 | Yakhini et al. |
| 7,267,951 B2 | 9/2007 | Alani et al. |
| 7,297,480 B2 | 11/2007 | Vogt |
| 7,615,349 B2 | 11/2009 | Riker et al. |
| 7,662,558 B2 | 2/2010 | Liew |
| 7,919,246 B2 * | 4/2011 | Lai et al. ................. 435/6.11 |
| 7,989,165 B2 | 8/2011 | Benson |
| 8,067,173 B2 | 11/2011 | Liew |
| 8,389,215 B2 | 3/2013 | Krueger et al. |

(Continued)

FOREIGN PATENT DOCUMENTS

| | | |
|---|---|---|
| JP | 2010014689 | 1/2010 |
| WO | WO00/10579 | 3/2000 |

(Continued)

OTHER PUBLICATIONS

Hodson et al. 1995. In situ PCR for visualization of microscale distribution of specific genes and gene products in prokaryotic communities. Applied and environmental microbiology. 61(11):4074-4082.
U.S. Appl. No. 12/114,669 Office Action dated Jun. 30, 2014.
U.S. Appl. No. 14/240,698, filed Feb. 24, 2014, Chapman et al.
U.S. Appl. No. 13/847,434 Office Action dated Mar. 21, 2014.
CA2770521 Office Action dated Feb. 24, 2014.
Ackerman et al. Charcot-Leyden crystal protein (galectin-10) is not a dual function galectin with lysophospholipase activity but binds a lysophospholipase inhibitor in a novel structural fashion. J Biol Chem 277(17): 1485968. (2002).

(Continued)

*Primary Examiner* — Ardin Marschel
(74) *Attorney, Agent, or Firm* — Wilson Sonsini Goodrich & Rosati

(57) ABSTRACT

The present invention provides methods for diagnosing melanoma and/or solar lentigo in a subject by analyzing nucleic acid molecules obtained from the subject. The present invention also provides methods for distinguishing melanoma from solar lentigo and/or dysplastic nevi and/or normal pigmented skin. The methods include analyzing expression or mutations in epidermal samples, of one or more skin markers. The methods can include the use of a microarray to analyze gene or protein profiles from a sample.

18 Claims, 31 Drawing Sheets

(56) References Cited

U.S. PATENT DOCUMENTS

| | | | |
|---|---|---|---|
| 8,492,102 | B2 | 7/2013 | Kashani-Sabet et al. |
| 8,541,170 | B2 | 9/2013 | Kennedy et al. |
| 2001/0051344 | A1 | 12/2001 | Shalon et al. |
| 2002/0037538 | A1 | 3/2002 | Trepicchio et al. |
| 2002/0086019 | A1 | 7/2002 | Wolf et al. |
| 2002/0110824 | A1 | 8/2002 | Rheins et al. |
| 2002/0115086 | A1 | 8/2002 | Rheins et al. |
| 2002/0119471 | A1 | 8/2002 | Rheins et al. |
| 2002/0127573 | A1 | 9/2002 | Rheins et al. |
| 2002/0150918 | A1 | 10/2002 | Rheins et al. |
| 2002/0165192 | A1 | 11/2002 | Kerr et al. |
| 2002/0197604 | A1 | 12/2002 | Rheins et al. |
| 2003/0010888 | A1 | 1/2003 | Shimada et al. |
| 2003/0032617 | A1 | 2/2003 | Harel et al. |
| 2003/0037538 | A1 | 2/2003 | Rendahl et al. |
| 2003/0044406 | A1 | 3/2003 | Dingivan |
| 2003/0049256 | A1 | 3/2003 | Tobinick |
| 2003/0108896 | A1 | 6/2003 | Vogt |
| 2003/0113906 | A1 | 6/2003 | Sangha et al. |
| 2003/0133936 | A1 | 7/2003 | Byrne et al. |
| 2003/0152923 | A1 | 8/2003 | Yakhini et al. |
| 2003/0207315 | A1 | 11/2003 | Burmer et al. |
| 2003/0224422 | A1 | 12/2003 | Evans et al. |
| 2003/0224465 | A1 | 12/2003 | Nevalainen et al. |
| 2004/0191782 | A1 | 9/2004 | Wang |
| 2005/0221334 | A1 | 10/2005 | Benson |
| 2005/0261210 | A1 | 11/2005 | Bhatnagar |
| 2006/0019256 | A1 | 1/2006 | Clarke et al. |
| 2006/0019286 | A1 | 1/2006 | Horvitz et al. |
| 2006/0040335 | A1 | 2/2006 | Butt et al. |
| 2006/0182755 | A1 | 8/2006 | Bodary-Winter et al. |
| 2006/0294615 | A1 | 12/2006 | Lin |
| 2007/0059717 | A1 | 3/2007 | Pascual et al. |
| 2007/0077553 | A1 | 4/2007 | Bentwich |
| 2007/0082347 | A1 | 4/2007 | Lanchbury et al. |
| 2007/0099209 | A1 | 5/2007 | Clarke et al. |
| 2007/0179198 | A1 | 8/2007 | Iwai et al. |
| 2007/0281314 | A1 | 12/2007 | Benson |
| 2008/0032293 | A1 | 2/2008 | Szabo et al. |
| 2008/0138819 | A1 | 6/2008 | Vogt |
| 2009/0082265 | A1 | 3/2009 | Bartel et al. |
| 2009/0111095 | A1 | 4/2009 | Nishimura et al. |
| 2009/0299640 | A1 | 12/2009 | Ellis et al. |
| 2010/0279877 | A1 | 11/2010 | Vogt |
| 2011/0059113 | A1 | 3/2011 | Celebi |
| 2011/0091384 | A1 | 4/2011 | Alani et al. |
| 2011/0158953 | A1 | 6/2011 | Scott |
| 2011/0159496 | A1 | 6/2011 | Kashani-Sabet et al. |
| 2011/0160080 | A1 | 6/2011 | Chang et al. |
| 2011/0262464 | A1 | 10/2011 | Chin et al. |
| 2011/0287034 | A1 | 11/2011 | Frank et al. |
| 2012/0065086 | A1 | 3/2012 | Benson |
| 2012/0071343 | A1 | 3/2012 | Ma et al. |
| 2012/0201750 | A1 | 8/2012 | Ryu |
| 2013/0079423 | A1 | 3/2013 | Abkevich et al. |
| 2013/0143747 | A1 | 6/2013 | Gutin et al. |
| 2013/0244256 | A1 | 9/2013 | Clarke et al. |
| 2013/0302242 | A1 | 11/2013 | Stone et al. |
| 2013/0344481 | A1 | 12/2013 | Kashani-Sabet et al. |
| 2014/0045915 | A1 | 2/2014 | Skog et al. |

FOREIGN PATENT DOCUMENTS

| | | |
|---|---|---|
| WO | WO03/001985 | 1/2003 |
| WO | WO2005/100603 | 10/2005 |
| WO | WO2006/002433 | 1/2006 |
| WO | WO2006/039399 | 4/2006 |
| WO | WO2007/023808 | 3/2007 |
| WO | WO2008/013772 | 11/2008 |
| WO | WO2011/039734 | 4/2011 |
| WO | WO2011/067549 | 6/2011 |
| WO | WO2012/013931 | 2/2012 |
| WO | WO2012/115885 | 8/2012 |
| WO | WO2012/125411 | 9/2012 |
| WO | WO2012/174282 | 12/2012 |
| WO | WO2013/022995 | 2/2013 |
| WO | WO2013/033609 | 3/2013 |
| WO | WO2013/098797 | 7/2013 |
| WO | WO2013/184905 | 12/2013 |
| WO | WO2014/028461 | 2/2014 |
| WO | WO2014/028884 | 2/2014 |

OTHER PUBLICATIONS

Affymetrix GeneChip Human Genome U133 Array Set HG-U133A, Geo Expression, Mar. 11, 2002 (XP002361324).

Aitman. DNA microarrays in medical practice. BMJ. 323(7313): 611-5 (2001).

Albert et al. Years of potential life lost: another indicator of the impact of cutaneous malignant melanoma on society. J Am Acad Dermato. 1990, 23(2 Pt 1):308-310.

Alberts et al. The immune system. Molecular Biology of the Cell. New York, NY, Garland Publishing, Inc. pp. 1229-1235 (1994).

Allison et al. A mixture model approach for the analysis of microarray gene expression data. Computational Statistics and Data Analysis 39: 1-20 (2002).

AppliedBiosystems, User Bulletin #2: Relative quantitation of gene expression. http://docs.appliedbiosystems.com/pebiodocs/04303859.pdf (2001).

Asada et al., Cytokine Gene Expression during the Eliciation Phase of Contact Sensitivity: Regulation by Endogenous IL-4, Journal of Investigative Dermatology. 108(4):406-411 (1997).

Asadullah et al., Cytokines: inreleukin and interferon therapy in dermatology Clinical & Experimental Dermatology 27: 578-584 (2002).

AU2008247502 Examination Report dated Jan. 31, 2013.

Ausubel et al., Current Protocols in Molecular Biology, section 4.7.1 (1987)adr.

Baehrecke. miRNAs: micro managers of programmed cell death. Curr Biol 13(12):R473-5 (2003).

Baker et al. Normal keratinocytes express Toll-like receptors (TLRs) 1, 2 and 5: modulation of TLR expression in chronic plaque psoriasis. Br J Dermatol 148(4): 670-9 (2003).

Baldi et al. A Bayesian framework for the analysis of microarray expression data: regularized t- test and statistical inferences of gene changes. Bioinformatics. 17(6):509-519 (2001).

Baldi et al., cDNA array technology in melanoma: an overview, J. Cell. Physiol., 196(2):219-223 (2003).

Bartel. MicroRNAs: genomics, biogenesis, mechanism, and function. Cell116(2): 281-97 (2004).

Bashir, et al. Physical and physiological effects of stratum corneum tape stripping. Skin Res Technol 7(1): 40-8. (2001).

Bataille, Clin. Exp. Dermatol. 25(6):464-467, 2000.

Bayon et al. Mechanisms of cell signaling in immune-mediated inflammation. Cytokines Cell Mol Ther 4(4): 275-86 (1998).

Becker et al., J. Invest. Dermatol. 116:983-988, 2001.

Becker et al. Experimental Dermatology (2010) 19:157-164.

Benavides et al. Impaired hair follicle morphogenesis and cycling with abnormal epidermal differentiation in nackt mice, a cathepsin L-deficient mutation. Am J Pathol 161(2): 693-703 (2002).

Benson et al. A comparison of keratin gene expression between inflamed and control skin obtained by tape harvest Journal of Investigative Dermatology, 122(3):A48 (2004).

Benson et al. An analysis of select pathogenic messages in lesional and non-lesional skin using non-invasive tape harvesting. Journal of Investigative Dermatology 2006, 126(10):2234-2241.

Benson et al., GenBank, Nucleic Acids. Res. 30(1):17-20 (2002).

Berger et al. A reappraisal of the 21-day cumulative irritancy test in man, J. Toxicol-Cut and Ocular Toxicol 1(2), 101-107 (1982).

Bertucci et al. Gene expression profiling of cancer by use of DNA arrays: how far from the clinic? Lancet Oncol 2(11): 674-82 (2001).

Bittner et al., Molecular classification of cutaneous malignant melanoma by gene expression profiling, Nature, 406:536-540 (2000).

Boelsma et al. Expression of skin-derived antileukoproteinase (SKALP) in reconstructed human epidermis and its value as a marker for skin irritation. Acta Derm Venereol 78(2): 107-13 (1998).

(56) References Cited

OTHER PUBLICATIONS

Borevitz et al. Large-scale identification of single-feature polymorphisms in complex genomes. Genome Res 2003, 13(3):513-523.
Boxman et al. Proteomic analysis of skin irritation reveals the induction of HSP27 by sodium lauryl sulphate in human skin. Br J Dermatol 146(5): 777-85 (2002).
Brand et al. Untersuchung Menschlicher Hautlymphe: Unterscheiden Sich Irritative Und Allergische Kontaktdermatititiden Bezuglich ihres Zytokinmusters? Zeitschrift Fur Hautkrankheiten, vol. 72, 1997, pp. 435-440.
Brand et al., IL-1B Protein in Human Skin Lymph Does Not Discriminiate Allergic from Irritant Contact Dermatitis, Contact Dermatitis, 35:152-156, Munksgaard, Denmark (1996).
Brennecke et al. Bantam encodes a developmentally regulated microRNA that controls cell proliferation and regulates the proapoptotic gene hid in Drosophila. Cell113(1): 25-36 (2003).
Breslow, Ann. Surg. 172:902-908, 1970.
Bunge et al. Improvement of Methodology for Assessing Bioequivalence of Topical Products, http://www.fda.gov/ohrms/dockets/ac/03/slides3996s2 07 bunge.pdf Oct. 22, 2003.
Bustin. Quantification of mRNA using real-time reverse transcription PCR (RT-PCR): trends and problems. J Mol Endocrinol 29(1): 23-39 (2002).
Cachia et al., "CDKN2A mutation and deletion status in thin and thick primary melanoma", *Clin. Cancer Res.*6(9):3511-3515, 2000.
Cai et al. Kaposi's sarcoma-associated herpesvirus expresses an array of viral microRNAs in latently infected cells. Proc Natl Acad Sci U S A. Apr. 12, 2005;102(15):5570-5. Epub Mar. 30, 2005.
Calin et al. A MicroRNA signature associated with prognosis and progression in chronic lymphocytic leukemia. N Engl J Med. Oct. 27, 2005;353(17):1793-801.
Callen et al. AAD Consensus statement on psoriasis therapies. J Amer Acad Dermatol 2003: 49:897-899).
Carr et al. Gene-expression profiling in human cutaneous melanoma. Oncogene 2003, 22(20):3076-3080.
Chakraboty et al., Differential gene expression in genetically matched mouse melanoma cells with different metastic potential, Gene 315L165 (2003).
Chen et al. MicroRNAs modulate hematopoietic lineage differentiation. Science 303(5654): 83-6 (2004).
Chung et al. (1996). Factors that control extravascular fibrinolysis. Semin Thromb Hemost 22(6): 479-88.
Chung et al. (2001). Sodium dodecyl sulfate induces plasminogen activator inhibitor type 2 expression in epidermal keratinocytes in vivo and in vitro. J Invest Dermatol 117(3): 647-53.
Ciafre et al. Extensive modulation of a set of icroRNAs in primary glioblastoma. Biochem Biophys Res Commun. Sep. 9, 2005;334(4):1351-8.
Clauser et al., Rapid mass spectrometromic peptide sequencing and mass matching for characterization of human melanoma proteins isolated by two-dimensional PAGE, PNAS 92:5072 (1995).
Colonna. (2003). TREMs in the immune system and beyond. Nat Rev Immunol 3(6):445-53.
Conner et al., "Detection of sickle cell Beta S-golbin allele by hybridization with synthetic oligonucleotides," *Proc. Natl. Acad. Sci. USA* 80: 278 (1983).
Coquette et al. (2003). Analysis of interleukin-1alpha (IL-1alpha) and interleukin-8 (IL-8) expression and release in in vitro reconstructed human epidermis for the prediction of in vivo skin irritation and/or sensitization. Toxicol in Vitro 17(3): 311-21.
Corsini and Galli, Cytokines and Irritant Dermatitis, Toxicology Letters, vol. 102-103, 1998, pp. 277-282.
Cullander et al., A quantitative minimally invasive assay for the detection of metals in the stratum corneum, J Pharm Biomed Anal. (2000) 22(2):265-79.
Cumberbatch et al. (2002). Differential regulation of epidermal langerhans cell migration by interleukins (IL)-1alpha and IL-1beta during irritant- and allergen-induced cutaneous immune responses. Toxicol Appl Pharmacol 182(2): 126-35.

Cummins et al. The colorectal microRNAome. Proc Natl Acad Sci U S A. Mar. 7, 2006;103(10):3687-92. Epub Feb. 27, 2006.
Curtin et al. The New England Journal of Medicine, Nov. 2005, vol. 353 No. 20, pp. 2135-2147.
Davy et al., Ephrin-A5 modulates cell adhesion and morphology in an integrin-dependent manner, EMBOJ. 19(2):5396-5403 (2000).
Deeds et al., "Patterns of melastatin mRNA expression in melanocytic tumors," *Human Pathology* 31(11):1346-1356, 2000.
Dekker et al., Characterization of interleukin-1 alpha-induced melanoma cell motility: inhibition by type I and type II receptor-blocking moncolonal antibodies, Melanoma Res. 7(3):223-230 (1997).
Dembinska-Kiec et al. Biochimica et Biophysica Acta (2005) 1740: 222-239.
Dong et al., Chemokines and diseases. European Journal of Dermatology. 13: 224-230 (2003).
Draft Guidance for Industry on Topical Dermatological Drug Product NDA's and ANDA's-In Vivo Bioavailability, Bioequivalence, in Vitro Release and Associated Studies: Dermatopharmacokinetics (DPK) Method Issues, http://srpub.pharma.org/letters/08.17.98.topical.derm.html. PRMA 1998.
Dreher et al., Colorimetric Method for Quantifying Human Stratum Corneum Removed by Adhesive Tape Stripping, Acta Derma Venereol (Stockholm) vol. 78, pp. 186-189.
Duncan et al., "Melastatin expression and prognosis in cutaneous malignant melanoma," *Journal of Clinical Oncology* 19(2):568-576, 2001.
Easty et al. Up-regulation of ephrin-A1 during melanoma progression, Int. J. Cancer, 84:494 (1999).
Edelman et al. Analysis of sample set enrichment scores: assaying the enrichment of sets of genes for individual samples in genome-wide expression profiles. Bioinformatics 2006, 22(14):e108-116.
Efron et al. Empirical hayes methods and false discovery rates for microarrays. Genet Epidemiol. 2002, 23(1):70-86.
EP05768406.0 Search Report dated Feb. 20, 2008.
EP08747580 Search Report dated Apr. 8, 2010.
EP09747631.1 Office Action dated Oct. 17, 2012.
EP09747631.1 Search Report dated Oct. 20, 2011.
EP10191595 Search Report dated Nov. 22, 2011.
EP13165664.7 Search Report dated Oct. 29, 2013.
EP9942356 Supplementary Parial EP Search Report dated Jun. 26, 2003.
Esquela-Kerscher et al. Oncomirs—microRNAs with a role in cancer. Nat Rev Cancer. Apr. 2006;6(4):259-69.
Farage et al., Further Development of Noninvavise Methods for Assessing Human Skin Irritation, Abstract #1909, The Proctor and Gamble Company, (1998).
Feghali et al. (1997). Cytokines in acute and chronic inflammation. Front Biosci 2: d12-26.
Flier et al. (1999). The CXCR3 activating chemokines IP-10, Mig, and IP-9 are expressed in allergic but not in irritant patch test reactions. J Invest Dermatol 113(4):574-8.
Fray et al. (2003). A potent, selective inhibitor of matrix metalloproteinase-3 for the topical treatment of chronic dermal ulcers. J Med Chem 46(16): 3514-25.
Freedberg et al., Keratins and the Keratinocyte Activiation Cycle, The Journal of Investigative Dermatology, vol. 116, No. 5, May 2001, pp. 633-640.
Galiegue et al. (2002). Exploitation of expression profiles: examples in oncology. J Soc Biol 196(4): 313-5.
Garofano et al., Advances in Forensic Haemogenetic. 6: 281-283 (1996).
Garofano et al., Comparison of Powerplex 16 System and Other Multiplex STR Typing Kits on Casework, (Reporto Carabinieri Investigazioni Scientifiche, Parma, Italia, 2000. Reference available at: http://www.promega.com/geneticidproc/ussymp1lproc/default.htm.
Garrett et al. Tired of the same old grind in the new genomics and proteomics era? Targets: Innovations in Genomics & Proteomics 1(5):156-162 (2002).
Genecard (www.genecards.org)—Accessed Nov. 11, 2009.
Gerritsen et al. Repeated tape stripping of normal skin: a histological assessment and comparison with events seen in psoriasis. Arch Dermatol Res 286(8):455-61 (1994).

(56) References Cited

OTHER PUBLICATIONS

Gershenwald et al. Gene expression profiling of human cutaneous melanoma: are we there yet? Cancer Bioi Ther 2004, 3(1):121-123.
Ghali et al., Epidermal and Hair Follicle Progenitor Cells express Melanoma-Associated Chondroitin Sulfate Proteoglycan Core Protein. Journal of Investigative Dermatology 122:433-442 (2004).
Gibson et al., A Novel Method for Real Time Quantitative RT-PCR. Genome Research 6: 995-1001 (1996).
Gloster et al. The epidemiology of skin cancer. Dermatol Surg. 1996. 22(3):217-226.
Goldschmidt, H., M.D., et al., Desquamation of the Human Horny Layer, Archives of Dermatology (1967) vol. 95, pp. 583-586.
Graham. Basic Pathologic Changes in Skin, in Dermal Pathology, Wd. J H Graham, W C Johnson, and E B Helwig, Harper-Row, Hagerstown, MD, pp. 119-135 (1972).
Grammatico et al., Involvement of the 4q21 region in human malignant melanomans: cytogenic and immunocytochemical characterization of three primary cell cultures, World. J. of Surgery 19:350 (1995).
Grangsjo et al., Different Pathways in Irritant Contact Eczema? Early Differences in the Epidermal Elemental Content and Expression of Cytokines after Application of 2 Different Irritants, Contact Dermititis, 35:355-360, Munksgaard, Denmark (1996).
Granstein R.D., New treatments for psoriasis N Engl J Med. 2001:345(4):284-287.
GRO1. Cancer Genetics Web. (www.cancer-genetics.org) 2 pages (2003).
Gyorffy et al. A web-based data warehouse on gene expression in human malignant melanoma. Journal of Investigative Dermatology. 2007 vol. 127 pp. 394-399. Published online Aug. 31, 2006.
Hamid et al., In Vivo Expression of IL-12 and IL-13 in Atopic Dermatitis, Journal of Allergy and Clinical Immunology, vol. 98, No. 1, Jul. 1996, pp. 1-8.
Hammond. MicroRNAs as oncogenes. Curr Opin Genet Dev. Feb. 2006; 16(1):4-9. Epub Dec. 19, 2005.
Haqq et al., The gene expression signatures of melanoma progression, Proc. Natl. Acad. Sci. U.S.A., 102(17):6092-6097 (2005).
Haskill et al., Identification of three related human GRO genes encoding cytokine functions, PNAS 87:7732 (1990).
Hatfield et al. (2003). Differential analysis of DNA microarray gene expression data. Mol. Microbiol. 47(4): 871-877.
Heid et al. Real Time Quantative PCR. Genome Research 6: 986-994 (1996).
Herouy. (2001). Matrix metalloproteinases in skin pathology (Review). Int J Mol Med 7(1): 3-12.
Hirao et al., Elevation of Interleukin 1 Receptor Antagonist in the Stratum Corneum of Sunexposed and Ultraviolet B-irradiated Human Skin, Journal of Investigative Dermatology (1996) vol. 106, No. 5, pp. 1102-1107.
Hirao et al., Elevation of Interleukin 1 Receptor Antagonist in the Stratum Corneum of Sun-Exposed and Ultravioloet B-Irradiated Human Skin, The Journal of Investigative Dermatology, 106(5):767-768 (1972).
Hoefakker et al. (1995). In vivo cytokine profiles in allergic and irritant contact dermatitis. Contact Dermatitis 33(4): 258-66 Munksgaard, Denmark (1995).
Hoffrage et al. (2000). Communicating Statistical Information. Science 290(5500): 2261-2262.
Hojyo-Tomoka et al., Does Cellophane Tape Stripping Remove the Horny Layer? Archives of Dermatology (1972) vol. 106, No. 5, pp. 767-768.
Holland et al., "Detection of specific ploymerase charin reaction product by utilizing the 5'—3' exonuclease activity of *Thermus aquaticus* DNA polymerase," Proc Natl Acad Sci USA, 88(16):7276 (1991).
Holleran et al, Regulationof epidermal sphingolipid synthesis by permeability barrier function, J. Lipid Research, 32:1151-58 (1991).

Howie et al., Epidermal Keratinocyte Production of Interferon-gama Immunoreactive Protein and mRNA is an Early Event in Allergic Contact Dermatitis, Journal of Investigative Dermatology, vol. 196, No. 6, 1996, pp. 1218-1223.
Hung et al. (2002). Global gene expression profiling in *Escherichia coli* K12: The effects of leucine-responsive regulatory protein. J. Biol. Chem. 277(43): 40309-40323.
Ichinose. (2001). Physiopathology and regulation of factor XIII. Thromb Haemost 86(1): 57-65.
Ijland et al., Expression of Angiogenic and Immunosuppressive Factors by Uveal Melanoma Cell Lines, Melanoma Research, 9:445-450 (1999).
Inozume et al., Novel melanoma antigen, FCRL/FREB, identified by CDNA profile comparision using DNA chip Are immunogenic in multiple melanoma patients, Int. J. Cancer: 114, 283-290 (2005).
Iorio et al. MicroRNA gene expression deregulation in human breast cancer. Cancer Res. Aug. 15, 2005;65(16):7065-70.
Jemal et al. Cancer statistics, 2003. CA Cancer J Clin 2003. 53(1):5-26.
Jovanovic, Archive of Oncology, 2005 vol. 13 pp. 75-77.
Junghans, Volker et al., Epidermal Cytokines IL-IB, TNF-a, and IL-12 in Patients with Atopic Dermatitis: Response to Application of House Dust Mite Antigens, The Journal of Investigative Dermatology, vol. 111, No. 6, Dec. 1998, pp. 1184-1188.
Kahari et al. (1997). Matrix metalloproteinases in skin. Exp Dermatol 6(5): 199-213.
Kalia et al. Homogeneous transport in a heterogeneous membrane: water diffusion across human stratum corneum in vivo. Biophys J 71(5):2692-700 (1996).
Kallioniemi, Biochip technologies in cancer research, Ann Med, Mar., 33(2):142-7 (2001).
Katerinaki et al., TNF-alpha increases human melanoma cell invasion and migration in vitro: the role of proteolytic enzymes, British Journ. of Cancer 89:1123 (2003).
Katz, H.I, M.D., et al., Skin surface touch print for diagnosing fungal infections, American Family Physician (1985) vol. 31, No. 4, pp. 189-194.
Kawada et al. (1997). Processing of cathepsins L, B and D in psoriatic epidermis. Arch Dermatol Res 289(2): 87-93.
Kerkhoff et al. (1999). The regulatory role of MRP8 (S100A8) and MRP14 (S100A9) in the transendothelial migration of human leukocytes. Pathobiology 67(5-6): 230-2.
Kilpatrick. (2002). Animal lectins: a historical introduction and overview. Biochim Biophys Acta 1572(2-3): 187-97.
Kim et al. The promise ofmicroarray technology in melanoma care. Cancer Contro. 2002, 9(1):49-53.
Klaschka et al., Individual Transparency Patterns of Adhesive-tape Strip Series of the Stratum Corneum, International Journal of Dermatology (1977), vol. 16. No. 10, pp. 836-841.
Klaschka et al., New Measuring Device of Horny Layer Transparency, Archives of Dermatology (1975) vol. 254, pp. 313-325.
Komine et al. (2001). Interleukin-1 induces transcription of keratin K6 in human epidermal keratinocytes. J Invest Dermatol 116(2): 330-8.
Komine et al. Regulation of epidermal expression of keratin K17 in inflammatory skin diseases. J Invest Dermatol 107(4): 569-75 (1996).
Kondo et al. Characterization of Epidermal Cytokine Profiles in Sensitization and elicitaion Phases of Allergic Contact dermatitis as well as Irritant Contact dermatitis in Mouse skin. Lymphokine and Cytokine Res. 1994, vol. 13, No. 6, pp. 367-375.
Kong et al. A multivariate approach for integrating genome-wide expression data and biological knowledge. Bioinformatics 2006.
Koning et al., T Cell Subsets and Cytokines in Allergic and Non-allergic Children. I. Analysis of IL-4 IFN-gamma and IL-13 mRNA Expression and Protein Production, Cytokine, vol. 9, No. 6, 1997, pp. 416-426.
Krasteva, M. 1993. Int. Dermatol. 32:547-560.
Kroese et al., Genetics in Medicine, 2006, vol. 6, p. 475-480.
Kupper, M., 1993. Am. J Dermatopathol. 11 :69-73.
Lacroix et al. (2002). A low-density DNA microarray for analysis of markers in breast cancer. Int J Biol Markers 17(1): 5-23.

(56) References Cited

OTHER PUBLICATIONS

Landegren e al, "DNA Diagnostics—Molecular Techniques and automation," Science, 242: 229-237 (1988).
Landegren et al., "A ligase-mediated gene detection technique," Science 241: 1077 (1988).
Lee et al. The *C. elegans* heterochronic gene lin-4 encodes small RNAs with antisense complementarity to lin-14. Cell 75(5): 843-54 (1993).
Lendeckel et al. (2003). Synergistic action of DPIV and APN in the regulation of T cell function. Adv Exp Med Biol 524: 123-31.
Lener et al., Expression profiling of aging in the human skin, Experimental Gerontology, 41:387-397 (2006).
Li et al. (2001). Model-based analysis of oligonucleotide arrays: expression index computation and outlier detection. Proc. Natl. Acad. Sci. U. S. A. 98(1): 31-36.
Liotta and Petricoin, "Molecular profiling of Human Cancer," *Nature Reviews/Genetics* 1:48-56, 2000.
Lobmann et al. (2002). Expression of matrix-metalloproteinases and their inhibitors in the wounds of diabetic and non-diabetic patients. Diabetologia 45(7): 1011-6.
Long et al. (2001). Improved statistical inference from DNA microarray data using analysis of variance and a Bayesian statistical framework. Analysis of global gene expression in *Escherichia coli* K12. J. Biol. Chem. 276(23): 19937-19944.
Lu et al., MicroRNA expression profiles classify human cancers, Nature, 435(7043):834-838 (2005).
Lucas et al. (2002). Massive inflammatory syndrome and lymphocytic immunodeficiency in KARAP/DAP12-transgenic mice. Eur J Immunol 32(9): 2653-63.
Lucentini. The Scientist (2004) vol. 18, p. 20.
Maddox et al. 1983; J. Exp. Med. 158:121 1-1216.
Marionnet et al. (2003). Modulation of gene expression induced in human epidermis by environmental stress in vivo. J Invest Dermatol. 121(6):1447-58.
Marttin et al., A Critical Comparison of Methods to Quantify Stratum corneum removed by Tape Stripping, Skin Pharmacology (1996) vol. 9, pp. 69-77.
McCarty et al. Epidermal hyperplasia overlying human melanoma correlates with tumour depth and angiogenesis. Melanoma Res 2003, 13(4): 379-387.
McKenzie et al., Interleukin-1 receptor antagonist inhibits subutaneous B16 melanoma growth in vivo, Anticancer Research, 1996, vol. 16, No. 1, pp. 437-441, see abstract.
McLean et al., Pharmacogenomic Analysis of Cytogenetic Response in Chronic Myeloid Leukemia Patients Treated with Imatinib Clinical Cancer Research, 10:155-165 (2004).
Melen et al. (1996). Human MxB protein, an interferon-alpha-inducible GTPase, contains a nuclear targeting signal and is localized in the heterochromatin region beneath the nuclear envelope. J Biol Chem 271(38): 23478-86.
Michael et al. Reduced accumulation of specific microRNAs in colorectal neoplasia. Mol Cancer Res. Oct. 2003;1(12):882-91.
Mitchell et al. Global analysis of cellular transcription following infection with an HIV-based vector. Mol Ther 2003, 8(4):674-687.
Miyashiro et al., "Molecular strategy for detecting metastatic cancers with use of multiple tumor-specific MAGE-A genes," *Clinical Chemistry* 47(3):505-512, 2001.
Molhuizen et al. (1995). Structural, biochemical, and cell biological aspects of the serine proteinase inhibitor SKALP/elafin/ESI. Biol Chem Hoppe Seyler 376(1): 1-7.
Morhenn et al. A noninvasive method for quantifying and distinguishing inflammatory skin reactions, Journal of the American Academy of Dermatology, 41(5 pt 1): 687-692 (1999).
Muller-Decker et al. (1998). Arachidonic acid metabolism in primary irritant dermatitis produced by patch testing of human skin with surfactants. Toxicol Appl Pharmacol 153(1): 59-67.
Muller-Decker, K., G. Furstenberger, et al. (1994). Keratinocyte-derived proinflammatory key mediators and cell viability as in vitro parameters of irritancy: a possible alternative to the Draize skin irritation test. Toxicol Appl Pharmacol 127(1): 99108.

Nair et al. Virus-encoded microRNAs: novel regulators of gene expression. Trends Microbiol. Mar. 10, 2006.
Nickoloff et al., Clinical Immunology and Immunopathology 73(1): 63-68 (1994).
Nickoloff, B.J., M.D., Ph. D et al., Perturbation of epidermal barrier function correlates with initiation of cytokine cascade in human skin, Journal of the American Academy of Dermatology (1994) vol. 30, No. 4, pp. 535-546.
Nikkola et al., High Expression Levels of Collagenase-1 and Stromelysin-1 Correlate with Shorter Disease-Free Survival in Human Metastic Melanoma, Int. J. Cancer 97:432-438 (2002).
Nurmi et al., High-performance real time quantitative RT-PCR using lanthanide probes and a dual temperature hybridization assay, Analytical Chemistry, 74(14) 3525-3532 (2002).
Ohmen D. et al., Overexpression of IL-10 in Atopic Dermatitis, The Journal of Immunology, vol. 154, 1995, pp. 1956-1963.
Onodera et al., Macrophage migration inhibition factor up-regulates expression of matrix metalloproteinases in synovial fibroblasts of rheumatoid arthritis, J. Biol. Chem, 275:444-450 (2000).
Page et al. The Power Atlas: a power and sample size atlas for microarray experimental design and research. BMC Bioinformatics 2006, 7:84.
Paik et al. A multigene assay to predict recurrence of tamoxifen-treated, nodenegative breast cancer. N Eng J Med 2004, 351(27):2817-2826.
Paludan et al., Use of the polymerase chan reaction in quantification of interleukin 8 mRNA in minute epidermal samples, J. Invest. Derm. 99:830-835, 1992.
Pang et al. Pathway analysis using random forests classification and regression. Bioinformatics 2006, 22(16):2028-2036.
Pavey et al. Microarray expression profiling in melanoma reveals a BRAF mutation signature. Oncogene 2004, 23(23):4060-4067.
PCT/US1999/19012 International Preliminary Examination Report dated May 26, 2000.
PCT/US1999/19012 International Search Report dated Jan. 31, 2000.
PCT/US2002/20728 International Preliminary Examination Report dated Feb. 2, 2005.
PCT/US2002/20728 International Search Report dated Oct. 27, 2003.
PCT/US2005/10911 International Preliminary Report on Patentability dated Oct. 4, 2006.
PCT/US2005/10911 International Search Report dated Nov. 18, 2005.
PCT/US2005/10911 Written Opinion dated Nov. 18, 2005.
PCT/US2007/009686 International Preliminary Report on Patentability dated Oct. 22, 2008.
PCT/US2007/009686 International Search Report and Written Opinion dated Dec. 18, 2007.
PCT/US2008/062545 International Preliminary Report on Patentability dated Nov. 10, 2009.
PCT/US2008/062545 International Search Report dated Sep. 18, 2008.
PCT/US2008/062545 Written Opinion dated Sep. 18, 2008.
PCT/US2009/44035 International Preliminary Report on Patentability dated Nov. 17, 2010.
PCT/US2009/44035 International Search Report and Written Opinion dated Sep. 3, 2009.
Perkins et al. (2002). A non-invasive tape absorption method for recovery of inflammatory mediators to differentiate normal from compromised scalp conditions. Skin Res Technol 8(3): 187-93.
Perkins et al., A noninvasive method to assess skin irritation and compromised skin conditions using simple tape adsorption of molecular markers of inflammation, Skin Res. Technol. 7(4):227-237 (2001).
Perkins et al., Development of a Noninvasive Method for Assessing Human Skin Irritation, The Toxicologist, 36(1):365 (1997).
Petit-Zeman. MicroRNAs hit the big time. Nat Rev Drug Discov. Jan. 2006;5(1):5.
Phan et al. (2002). Role of the C-terminal propeptide in the activity and maturation of gamma γ-interferon-inducible lysosomal thiol reductase (GILT). Proc Natl Acad Sci U S A 99(19): 12298-303.

(56) References Cited

OTHER PUBLICATIONS

Pilcher et al. (1999). Role of matrix metalloproteinases and their inhibition in cutaneous wound healing and allergic contact hypersensitivity. Ann N Y Acad Sci 878: 12-24.
Pistoor et al., Novel Predictive Assay for Contact Allergens Using Human Skin Explant Cultures, American Journal of Pathology 149(1):337-343 (1996).
Potts et al., Physical Methods for Studying Stratum Corneum Lipids, Seminars in Dermatology (1992) vol. 11, No. 2, pp. 129-138.
Raval et al. (2003). Loss of expression of tropomyosin-1, a novel class II tumor suppressor that induces anoikis, in primary breast tumors. Oncogene 22(40): 6194-203.
Reinhart et al. The 21-nucleotide let-7 RNA regulates developmental timing in *Caenorhabditis elegans*. Nature 403(6772):901-6 (2000).
Rougier et al., In Vivo Correlation Between Stratum Corneum Resevoir Function and Percutaneous Absorption, J. Investigative Dermatology, 81:275-278 (1983).
Rougier et al., In Vivo Percutaneous Penetration of Some organic Compounds Related to Anatomic Site in Humans: Predictive Assessment by the Stripping Method, J. Pharmaceutical Sciences, 76:451-454 (1987).
Rougier et al., Regional variation in percutaneous absorption in man: measurement by the stripping method, Arch Dermatol Res. (1986) 278(6): 465-9.
Rougier et al., The measurement of the stratum corneum reservoir. A predictive method for in vivo percutaneous absorption studies: influence of application time, J Invest Dermatol. (1985) 84(1):66-8.
Rowe, A. et al., Interleukin-4 and the Interleukin-4 Receptor in Allergic Contact Dermatitis, Contact Dermatitis, vol. 38, No. 1, Jan. 1998, pp. 36-39.
Rudert, Genomics and proteomics tools for the clinic, Curr Opin. Mol. Ther., Dec.; 2(6):633 42 (2000).
Ryan et al. Cytokine mRNA Expression in Human Epidermis After Patch Treatment with Rhus and Sodium Lauryl Sulfate, American Journal of Contact Dermatitis, vol. 10, No. 3, Sep. 1999, pp. 127-135.
Saiki et al., *Bio/Technology* 3:1008-1012 (1985).
Samal et al. (1994). Cloning and characterization of the cDNA encoding a novel human pre-B-cell colony-enhancing factor. Mol Cell Biol 14(2): 14317.
Satagopan et al. (2003). A statistical perspective on gene expression data analysis. Stat Med 22(3): 481-99.
Seftor et al. Cooperative interactions of laminin 5 gamma2 chain, matrix metalloproteinase-2, and membrane type-1-matrix/metalloproteinase are required for mimicry of embryonic vasculogenesis by aggressive melanoma. Cancer Res 2001, 61(17):6322-6327.
Shintani et al., Growth-Regulated Oncogene-1 Expression is Associated with Angiogenesis and Lymph Node Metastasis in Human Oral Cancer, Oncology 66:316-322 (2004).
Shattuck et al., MGSA/GRO transcription is differentially regulated in normal retinal pigment epithelial and melanoma cells. Molecular and Cellular Biology 14 (1): 791-802 (1994).
Si et al., Expression of the Neuroglandular Antigen and Analogues in Melanoma. CD9 Expression Appears Inversely Related to Metastic Potential of Melanoma, Int. J. Cancer 54:37-43 (1993).
Slack et al. MicroRNAs as a potential magic bullet in cancer. Future Oncol. Feb. 2006;2(1):73-82.
Smyth et al. Statistical issues in eDNA microarray data analysis. Methods Mol Biol 2003, 224:111-136.
Soufir et al., Association Between Endothelin Receptor B Nonsynonymous Variants and Melanoma Risk, Journ. Nat'l. Cancer Inst. 97(17):1297-1301 (2005).
Stolz et al. Semiquantitative analysis of histologic criteria in thin malignant melanomas. J Am Acad Dermato.1989, 20(6): 1115-1120.
Stuart et al. In silico dissection of cell-type associated patterns of gene expression in prostate cancer. Proc Natl Acad Sci USA 2004, 101(2):615-620.
Su et al. Identification of tumor-suppressor genes using human melanoma cell lines UACC903, UACC903(+6), and SRS3 by comparison of expression profiles. Mol Carcinog 2000, 28(2):119-127.
Suzuki et al. (2000). Control selection for RNA quantitation. Biotechniques 29(2): 332-7.
Syrokou et al. (2002). Synthesis and expression of mRNA encoding for different versican splice variants is related to the aggregation of human epithelial mesothelioma cells. Anticancer Res 22(6C): 4157-62.
Tagawa. A microRNA cluster as a target of genomic amplification in malignant lymphoma. Leukemia. Nov. 2005;19(11):2013-6.
Tetsuji, H. et al., Elevation of Interleukin 1 Receptor Antagonist in the Stratum Corneum of Sunexposed and Ultraviolet B-irradiated Human Skin, Journal of Investigative Dermatology (1996) vol. 106, No. 5, pp. 1102-1107.
Thatcher et al. miRNA Expression Analysis During Normal Zebrafish Development and Following Inhibition of the Hedgehog and Notch Signaling PathwaysDevelopmental Dynamics (2007) 236: 2172-2180.
Thiele et al. Macromolecular carbonyls in human stratum corneum: a biomarker for environmental oxidant exposure? FEBS letters 422: 403-406 (1998).
Thiele et al. Protein Oxidation in Human Stratum Corneum: susceptibility of Keratins to Oxidation in Vitro and Presence of a Keratin Oxidation Gradient in Vivo. Journal of Investigative Dermatology 113: 335-339 (1999).
Thorey et al. (2001). The $Ca^{2+}$-binding proteins S100A8 and S100A9 are encoded by novel injury-regulated genes. J Biol Chem 276(38): 35818-25.
Tibshirani et al. Diagnosis of multiple cancer types by shrunken centroids of gene expression. Proc Natl Acad Sci USA 2002, 99(10):6567-6572.
Tomic-Canic et al. (1998). Epidermal signal transduction and transcription factor activation in activated keratinocytes. J Dermatol Sci 17(3): 167-81.
Torabian et al. Current Opinion in Oncology (2005) 17:167-171.
Torre and Gino, Epidermal Cells on Stubs Used for Detection of GSR with SEM-EDX: Analysis of DNA Polymorphisms, Journal of Forensic Sciences, JFSCA, vol. 41, No. 4, Jul. 1996, pp. 658-659.
Tricarico et al. (2002). Quantitative real-time reverse transcription polymerase chain reaction: normalization to rRNA or single housekeeping genes is inappropriate for human tissue biopsies. Anal Biochem 309(2): 293-300.
Ulfgren et al. (2000). An immunohistochemical analysis of cytokine expression in allergic and irritant contact dermatitis. Acta Derm Venereol 80(3): 167-70.
U.S. Appl. No. 11/710,661 Office Action dated Jan. 11, 2010.
U.S. Appl. No. 11/710,661 Office Action dated Jul. 14, 2009.
U.S. Appl. No. 11/710,661 Office Action dated Jul. 21, 2010.
U.S. Appl. No. 13/136,278 Office Action dated Mar. 14, 2012.
U.S. Appl. No. 13/136,278 Office Action dated Sep. 25, 2012.
U.S. Appl. No. 13/847,434 Office Action dated Oct. 10, 2013.
U.S. Appl. No. 09/375,609 Office Action dated Dec. 18, 2003.
U.S. Appl. No. 09/375,609 Office Action dated Jan. 31, 2001.
U.S. Appl. No. 09/375,609 Office Action dated Jul. 12, 2001.
U.S. Appl. No. 09/967,658 Office Action dated Apr. 22, 2003.
U.S. Appl. No. 09/967,658 Office Action dated Jun. 6, 2003.
U.S. Appl. No. 09/970,617 Office Action dated Jun. 2, 2004.
U.S. Appl. No. 09/972,531 Office Action dated Jun. 14, 2004.
U.S. Appl. No. 09/976,356 Office Action dated Sep. 24, 2003.
U.S. Appl. No. 09/976,361 Office Action dated Jun. 28, 2004.
U.S. Appl. No. 09/976,613 Office Action dated Jun. 28, 2004.
U.S. Appl. No. 10/184,846 Office Action dated May 5, 2005.
U.S. Appl. No. 10/184,846 Office Action dated Sep. 26, 2006.
U.S. Appl. No. 10/816,457 Office Action dated Mar. 13, 2006.
U.S. Appl. No. 10/816,457 Office Action dated Sep. 5, 2005.
U.S. Appl. No. 11/788,644 Office Action dated Jul. 25, 2008.
U.S. Appl. No. 12/114,669 Office Action dated Aug. 5, 2010.
U.S. Appl. No. 12/114,669 Office Action dated Jan. 6, 2011.
U.S. Appl. No. 12/114,669 Office Action dated Jun. 21, 2011.
U.S. Appl. No. 12/114,669 Office Action dated Nov. 17, 2009.
U.S. Appl. No. 12/991,685 Office Action dated Mar. 12, 2013.
U.S. Appl. No. 12/991,685 Office Action dated Nov. 4, 2013.
Vallejo et al. (2000). Central role of thrombospondin-1 in the activation and clonal expansion of inflammatory T cells. J Immunol 164(6): 2947-54.

(56) References Cited

OTHER PUBLICATIONS

Van Der Molen, R.G. et al., Tape stripping of human stratum corneum yields cell layers that originiate from various depths because of furrows in the skin, Archives of Dermatological Research (1997) vol. 289, pp. 514-518.
Van Der Valk et al., A functional study of the skin barrier to evaporative water loss by means of repeated cellophane-tape stripping, Clinical and Experimental Dermatology (1990) vol. 15, No. 3, pp. 180-182.
van Hoogdalem, Assay of Erythromycin in Tape Strips of Human Stratum corneum and Some Preliminary results in Man, Skin Pharmacol (1992) vol. 5, pp. 124-128.
van Ruissen et al. (1998). Differential effects of detergents on keratinocyte gene expression. J Invest Dermatol 110(4): 358-63.
Verhoef. (1991). The phagocytic process and the role of complement in host defense. J Chemother 3 Suppl 1: 93-7.
Vermeer et al. (2003). Segregation of receptor and ligand regulates activation of epithelial growth factor receptor. Nature 422(6929): 322-6.
Volinia et al. A microRNA expression signature of human solid tumors defines cancer gene targets. Proc Natl Acad Sci USA. Feb. 14, 2006;103(7):2257-61. Epub Feb. 3, 2006.
Wachsman et al. Noninvasiave genomic detection of melanoma, British Journal of Dermatology (2011) 164:797-806.
Wang et al., Melanoma-restricted Genes, J. of Translational Medicine 2: 34 pp. 1-14 (2004).
Wang et al., MGSA/GRO-mediated melanocyte transformation involves induction of Ras expression. Oncogene 19: 4647-4659 (2000).
Washington Report: Skin Tape Stripping Method for Generic Dermatologic Drug Approval Remains in Question, http://www.aadassociation.org/old/washReports/dec99_washrep.html (1999).
Wassem et al., Keratin 15 expression in stratified epithelia: down regulation in activated keratincytes. Journal of Investigative Dermatology 113: 362-269 (1999).
Weigand, D.A., M.D. et al., Removal of Stratum Corneum in Vivo: An Improvement of the Cellophane Tape Strapping Technique, The Journal of Investigative Dermatology (1973) vol. 60, No. 2, pp. 84-87.
Weinstock, "Early detection of melanoma," *JAMA* 284:886-889, 2000.
Welss et al. (2003). Hurpin is a selective inhibitor of lysosomal cathepsin L and protects keratinocytes from ultraviolet-induced apoptosis. Biochemistry 42(24): 7381-9.
Werfel et al., Cytokines as Mediators of Allergic Tissue Response, Allergelogie Dustrie Verlag Muenchen-Deisenhofen, DE, vol. 20, No. 11, 1997, pp. 546-550.
Werfel, T. et al., High IL-4 Secretion from Skin-Derived Nickel Specific T-lymphocytes is Associated with Atopy and Acute Eczema are associated with in Allergic Contact Dermatitis, Journal of Allergy and Clinical Immunology, vol. 101, No. 1, Part 2, Jan. 1998, p. S129.
Whipple et al. (2002). DNA microarrays in otolaryngology—head and neck surgery. Otolaryngol Head Neck Surg 127(3): 196-204.
Wolyn et al. Light-response quantitative trait loci identified with composite interval and extreme array mapping in *Arabidopsis thaliana*. Genetics 2004, 167(2):907-917.
Wong et al. Use of RT-PCR and DNA microarrays to characterize RNA recovered by non invasive tape harvesting of normal and inflamed skin. J Invest Dermato. 2004, 123(1):159-167.
Wu et al. Preprocessing of oligonucleotide array data. Nat Biotechnol 2004, 22(6):656-658; author reply 658.
Wu et al. Stochastic models inspired by hybridization theory for short oligonucleotide arrays. J Comput Bio. 2005, 12(6):882-893.
Xu et al. RT-PCR Analysis of in Vivo Cytokine Profiles in Murine Allergic Contact Dermatitis to DNCB. 1996. Toxicology Methods. 6:23-31.
Xu et al. Expression of Cytokine mRNAs in the Draining Lymph Nodes Following Contact Sensitivity in Mice. Apr. 1997. Toxicology Methods. 7:137-148.
Yanaihara et al. Unique microRNA molecular profiles in lung cancer diagnosis and prognosis. Cancer Cell. Mar. 2006;9(3):189-98.
Yawalkar and Pichler, Pathogenesis of Drug-Induced Exanthema, Int Arch Allergy immunol, vol. 124,2001. pp. 336-338.
Yi et al., Morphogenesis in skin is governed by discrete sets of differentially expressed microRNAs, Nature Genetics (2006) 38(3):356-62.
AU2009246180 Examination Report dated Sep. 10, 2014.
AU2009285645 Examination Report dated Oct. 20, 2014.
D-SQUAME from Cu-DEM (2003).
Gerami et al. Development of a novel noninvasive adhesive patch test for the evaluation of pigmented lesions of the skin. J Am Acad Dermatol 71(2):237-244 (2014).
Livak et al. Analysis of Relative Gene Expression Data Using RealTime Quantitative PCR and the 2-delta delta Ct Method. Methods 25:402 (2001).
NCBI GEO Profiles Database, DataSet Record GDS1989, excerpts (2 pages), Apr. 2006.
PCT/US2014/044588 International Search Report and Written Opinion dated Oct. 20, 2014.
Rittie et al. UV-light-induced signal cascades and skin aging. Ageing Research Reviews 1:705-720 (2002).
Takashi et al. Novel melanoma antigen, FCRL/FREB, identified by cDNA profile comparison using DNA chip Are immunogenic in multiple melanoma patients. International Journal of Cancer 114(2):283-290 (2005).
U.S. Appl. No. 12/114,669 Office Action dated Oct. 27, 2014.
U.S. Appl. No. 13/847,434 Office Action dated Nov. 18, 2014.
U.S. Appl. No. 14/208,155 Office Action dated Nov. 20, 2014.
User Bulletin #2 from Applied Biosystems (Oct. 2001).
Vandesompele et al. Accurate normalization of real-time quantitative RT-PCR data by geometric averaging of multiple internal control genes. Genome Biology 3(7):12 (Jun. 2002).

\* cited by examiner

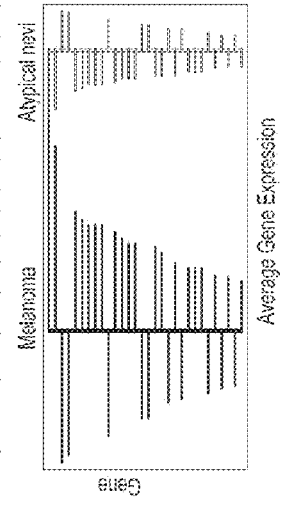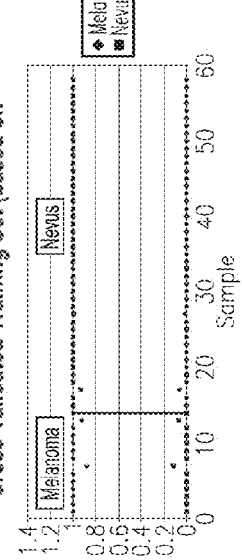
FIG. 4D

- Prediction Analysis of Microarrays (PAM)
  - Training set: 18 Melanomas and 18 atypical nevi
    - 350 differentially expressed genes selected
      - T-test, P <0.001; FDR <0.05; Multi-testing correction
    - Run PAM with 350 genes
    - Repeat PAM using top 20 ranked genes
  - Testing set: 13 Melanomas and 53 nevi Training Set

| Observed | Predicted Class Diagnosis | |  |
|---|---|---|---|
| | Melanoma | Atypical Nevi | |
| Melanoma | 18 | 0 | |
| Atypical Nevi | 1 | 17 | |
| Total | 19 | 17 | |

Testing Set

| Observed | Predicted Class Diagnosis | |  |
|---|---|---|---|
| | Melanoma | Atypical Nevi | |
| Melanoma | 13 | 0 | |
| Atypical Nevi | 5 | 48 | |
| Total | 18 | 48 | |

FIG. 6D

| Training Confusion Matrix (Threshold=0.5) | | | |
|---|---|---|---|
| True\Predicted | M | N | Class Error rate |
| M | # | 0 | 0 |
| N | 1 | # | 0.055555556 |

| CV Confusion Matrix (Threshold=0.53344) | | | |
|---|---|---|---|
| True\Predicted | M | N | Class Error rate |
| M | # | 0 | 0 |
| N | 1 | # | 0.055555556 |

| Settings Name: Settings1 | | | | | | |
|---|---|---|---|---|---|---|
| Offset Quantile | 50 | | Offset Value | 758.4297 | | |
| | both | | RNG Seed | 420473 | | |
| Prior Distribution (Sample Prior) | | | | | | |
| | Class | M | N | | | |
| | Prob. | 0.5 | 0.5 | | | |

| Settings Name: Settings3 | | | | | | |
|---|---|---|---|---|---|---|
| Offset Quantile | 50 | | Offset Value | 758.4297 | | |
| | both | | RNG Seed | 420473 | | |
| Prior Distribution (Sample Prior) | | | | | | |
| | Class | M | N | | | |
| | Prob. | 0.5 | 0.5 | | | |

FIG. 6E

A 20-Gene Classifier Discriminates Melanoma From Atypical Nevi

- Top 20 of 73 genes selected from TreeNet®
- Perform TreeNet® analysis using only these 20 genes
  - 6 of the 20 genes have known relevance to melanoma

Training Set

| Observed | Predicted Class | |  |
|---|---|---|---|
| | Diagnosis | | |
| | Melanoma | Atypical Nevi | |
| Melanoma | 37 | 0 | |
| Atypical Nevi | 2 | 35 | |
| Total | 39 | 35 | |
| Sensitivity | 37/37 = 100% | | |
| Specificity | 35/37 = 95% | | |

Testing Set

| Observed | Predicted Class | |
|---|---|---|
| | Diagnosis | |
| | Melanoma | Atypical Nevi |
| Melanoma | 25 | 0 |
| Atypical Nevi | 9 | 47 |
| Total | 34 | 47 |
| Sensitivity | 25/25 = 100% | |
| Specificity | 47/56 = 84% | |
| PPV | 74% | |
| NPV | 100% | |

FIG. 9

Development of a Classifier to Discriminate Melanoma from Atypical Nevi by a Non-invasive Tape Strip-based Genomic Profiling

Introduction

The incidence of melanoma is increasing at the fastest rate of all cancers in the United States. It is already the seventh most common serious cancer in the United States with a lifetime risk of 1 in 41 in men and 1 in 61 in women. Although melanoma accounts for more than 70% of skin cancer deaths, when detected early it is considered highly curable. In current clinical practice, the detection of melanoma is based upon visual cues, including the "ABCDE" criteria for pigmented nevi and results of optical imaging techniques, such as dermoscopy and confocal microscopy. However, only 1 to 10% of lesions biopsied for suspicion of melanoma are positive for this disease upon histopathologic examination. Thus, there is a need for a test that improves the ease and accuracy of melanoma detection in clinical practice.

Epidermal Genetic Information Retrieval (EGIR™) (DermTech International, Inc.) uses a custom adhesive film to harvest RNA from stratum corneum. Developed by Morhenn and Rheins (*J Am Acad Dermatol* 4: 687 [1999]). EGIR™ was shown to harvest sufficient cellular RNA for accurate assessment of gene expression by both quantitative RT-PCR and microarray assay (Wong et al. *J Invest Derm* 123: 159 [2004]).

The EGIR™ methodology uses four 20 mm tapes (pictured below) to sample stratum corneum. RNA so harvested has been found to be stable for assay, when kept at ambient temperature for 72 hours. This makes it ideal for use in the office setting.

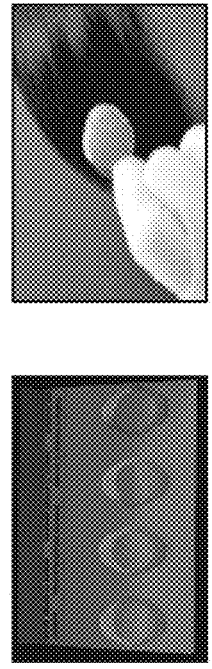

Preliminary Work

Recent work showed that EGIR™, non-invasive tape stripping of stratum corneum can be used to differentiate melanoma from atypical nevi and normal skin (Wachsman et al. *J Invest Derm* 127: S145 [2007]). Additional work, in which 31 melanomas, 71 atypical nevi, and 15 normal skin controls were analyzed by GeneChip assay, identified 264 differentially expressed genes (p<0.001, false discovery rate q<0.05). Hierarchical cluster analysis of these genes (see Figure below) showed that melanomas can be distinguished from atypical nevi and normal skin, and, suggested the existence of different classes of atypical nevi. Several of the genes were found by Ingenuity Pathways analysis to play a role in melanocyte development and function, as well as, skin development, cellular proliferation, and cancer. These findings further demonstrated that the presence of melanoma, directly or indirectly, alters the gene expression profile of stratum corneum.

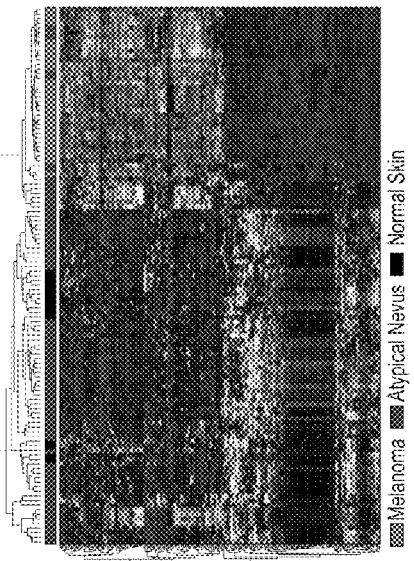

Summary

- The results demonstrate that EGIR™-harvested stratum corneum RNA can be used for the detection of both in situ and invasive melanoma.

- Class prediction modeling shows that the TreeNet® algorithm outperforms both PAM and Random Forests.

- A 20-gene classifier, developed by TreeNet® analysis, discriminates in situ and invasive superficial spreading melanoma and lentigo maligna from atypical nevi.

- Testing of this 20-gene classifier, using an independent set of sample data, shows it to be 100% sensitive and 84% specific for detection of both melanoma and lentigo maligna.

- In addition, this 20-gene melanoma classifier has a positive predictive value (PPV) of 74% and a negative predictive value (NPV) of 100%.

- The 20-gene classifier provides the basis for the development of a non-invasive genomic assay for the clinical detection of melanoma.

A 20-Gene Classifier Discriminates Melanoma From Atypical Nevi

- Top 20 of 73 genes selected from TreeNet®
- Perform TreeNet® analysis using only these 20 genes
  - 6 of the 20 genes have known relevance to melanoma

Training Set

| | Predicted Class | |
|---|---|---|
| | Diagnosis | |
| Observed | Melanoma | Atypical Nevi |
| Melanoma | 37 | 0 |
| Atypical Nevi | 2 | 35 |
| Total | 39 | 35 |
| Sensitivity | 37/37 = 100% | |
| Specificity | 35/37 = 95% | |

Testing Set

| | Predicted Class | |
|---|---|---|
| | Diagnosis | |
| Observed | Melanoma | Atypical Nevi |
| Melanoma | 25 | 0 |
| Atypical Nevi | 9 | 47 |
| Total | 34 | 47 |
| Sensitivity | 25/25 = 100% | |
| Specificity | 47/56 = 84% | |
| PPV | 74% | |
| NPV | 100% | |

FIG. 10 cont.

Development of a 19-Gene Classifier Accurately Discriminates
Melanoma from Atypical Nevi

- Supervised analysis of GeneChip data
    - Training set: 37 melanomas and 37 atypical nevi
        - t-test with multi-testing correction identified 7,199 differentially expressed genes (p < 0.05; FDR < 0.05)
        - TreeNet analyses of differentially expressed genes identified a 19-gene classifier
        - Sensitivity: 100%, specificity 95%
    - Testing set: 39 melanomas and 89 atypical nevi
        - PPV: 39/50 = 78%, NPV: 78/78 = 100%
        - Sensitivity 100%, specificity 88%

| Training Set | | | Test Set | | |
|---|---|---|---|---|---|
| | Predicted Class | | | Predicted Class | |
| | Diagnosis | | | Diagnosis | |
| Observed | Melanoma | Atypical Nevi | Observed | Melanoma | Atypical Nevi |
| Melanoma | 37 | 0 | Melanoma | 39 | 0 |
| Atypical Nevi | 2 | 35 | Atypical Nevi | 11 | 78 |
| (Total) | 39 | 35 | (Total) | 50 | 78 |

FIG. 11

Discovery of a Multi-Gene Classifier to Differentiate Solar Lentigo from Normal Skin

- Training set: 8 solar lentigines and 8 normal skin controls
  - 1600 differentially expressed genes selected
    - T-test, P <0.05
  - Discover a 100-gene classifier
- Testing set: 3 solar lentigines and 3 normal skin controls
  - Sensitivity: 100%
  - Specificity: 100%

| Training Set | | | Testing Set | | |
|---|---|---|---|---|---|
| Observed | Predicted Class | | Observed | Predicted Class | |
| | Diagnosis | | | Diagnosis | |
| | Solar Lentigo | Normal Skin | | Solar Lentigo | Normal Skin |
| Solar Lentigo | 8 | 0 | Solar Lentigo | 3 | 0 |
| Normal Skin | 0 | 8 | Normal Skin | 0 | 3 |
| Total | 8 | 8 | Total | 3 | 3 |

FIG. 14

DIAGNOSIS OF MELANOMA AND SOLAR LENTIGO BY NUCLEIC ACID ANALYSIS

CROSS REFERENCE TO RELATED APPLICATIONS

This application is a continuation of U.S. application Ser. No. 14/172,784, filed Feb. 4, 2014, which is a continuation of U.S. application Ser. No. 12/991,685 filed Mar. 14, 2011, which is a U.S. National Stage application of International Application No. PCT/US2009/044035 filed May 14, 2009, which claims the benefit under 35 USC §119(e) to U.S. Application Ser. No. 61/058,149 filed Jun. 2, 2008, U.S. Application Ser. No. 61/053,998 filed May 16, 2008 and U.S. Application Ser. No. 61/127,731 filed May 14, 2008. The disclosure of each of the prior applications is considered part of and is incorporated by reference in the disclosure of this application.

FIELD OF THE INVENTION

The invention relates generally to methods of characterizing pigmented skin lesions suspected of being melanomas using primarily non-invasive skin sampling.

BACKGROUND INFORMATION

Melanoma is a serious form of skin cancer in humans. It arises from the pigment cells (melanocytes), usually in the skin. The incidence of melanoma is increasing at the fastest rate of all cancers in the United States with a lifetime risk of 1 in 68. Although melanoma accounts for only 4% of all dermatologic cancers, it is responsible for 80% of all deaths from skin cancers. It has long been realized that recognition and diagnosis of melanoma, when it is early stage disease, is key to its cure.

Given this, it is imperative that research be carried out not only on therapeutics for melanoma, but also on all aspects of melanoma including prevention and detection. Most of these deaths from melanoma could have been prevented if the melanomas, initially located on the skin, could have been detected in their early stages. The ability to cure melanoma in its earliest skin stage, in situ, is virtually 100% if the melanoma is adequately surgically excised. If the melanoma is caught in a later stage, where it has invaded to a depth of 4 mm or more, the ten-year survival rate is less than 50%. If the melanoma is not detected until it has spread to distant parts of the body (Stage IV), the prognosis is dismal, with only 7-9% of patients surviving 5 years, with the median survival time being 8-9 months. The long-term "cure" rate for Stage IV melanoma is only 1-2%.

To advance early detection of melanoma, several things must be improved. People need to be better educated with regards to the risks of melanoma and how to prevent and detect it on their own skin. Also physicians need to be more alert to the possibility of melanoma and be better trained in detection. But even if these two areas are improved, the diagnosis of melanoma on the skin is still difficult. Studies have shown that even expert clinicians working in pigmented lesion clinics where melanoma is their specialty are only able to determine whether a suspicious pigmented lesion is melanoma or not with 60-80% sensitivity. This leads to the need for surgical biopsy of large numbers of pigmented lesions for every melanoma that is detected, and, doubtless, to the missing of some melanomas in their early stages.

In current practice melanoma is diagnosed by biopsy and histopathological examination; approximately 20 to 30 biopsies must be performed to find one melanoma and even then some melanomas are missed in the earliest stage. The limitations of visual detection are apparent to dermatologists who are constantly searching for ways to better determine whether suspicious lesions are melanoma or not without having to cut them out first. To this end, epiluminescence microscopy (ELM) has come into use. This is a method whereby lesions are looked at using a device that simultaneously magnifies the lesion while reducing visual interference from refractive index differences at the skin-air interface. While ELM does give a different view, it is of limited improvement. Studies have shown that until one becomes fairly skilled in utilizing the instrument, sensitivity in detection of melanoma actually decreases. Even very skilled users of ELM improve their ability to detect melanomas only by 5-10%. This still leads to an unacceptable sensitivity in detection and the need to biopsy large numbers of benign lesions to detect a few melanomas. And again, some melanomas will be missed completely in their early stages.

Clearly there is a need for further development of technology that will enable physicians to determine the nature and extent of suspicious lesions of the skin. Such technology would ideally directly assay the physiology of the suspect lesion to enable a sensitive diagnosis.

SUMMARY OF THE INVENTION

The present invention is based, in part, on the discovery that analysis of nucleic acid molecules or of protein expression products of nucleic acid molecules from specific genes can be used to characterize skin lesions in a subject. The method provides valuable genetic information based on DNA, messenger RNA, or protein expression products obtained therefrom, for example.

In one embodiment, the method involves use of a non-invasive approach for recovering nucleic acids such as DNA or messenger RNA or proteins from the surface of skin via a tape stripping procedure that permits a direct quantitative and qualitative assessment of biomarkers. Although tape-harvested nucleic acid and protein expression products are shown to be comparable in quality and utility to recovering such molecules by biopsy, the non-invasive method provides information regarding cells of the outermost layers of the skin that may not be obtained using biopsy samples. Finally, the non-invasive method is far less traumatic than a biopsy.

Thus, the non-invasive method is used to capture cells on pigmented skin lesions that are suspected of being melanomas. Nucleic acid molecules obtained from skin cells captured by the non-invasive method are analyzed in order to diagnose the nature of the lesion (e.g., malignant melanoma). In one embodiment, a nucleic acid molecule is amplified prior to analysis. Secondary outcomes could include tests for diagnosis and prognosis of a variety of pigmented skin lesions and even to predict a therapeutic regimen. In another embodiment, the skin cells are lysed to extract one or more proteins, which are then quantitated to diagnose the nature of the lesion. It should be understood that the methods of the invention are not limited to non-invasive techniques for obtaining skin samples. For example, but not by limitation, one of skill in the art would know other techniques for obtaining a skin sample such as scraping of the skin, biopsy, suction, blowing and other techniques. As described herein, non-invasive tape stripping is an illustrative example for obtaining a skin sample.

In another embodiment, the methods involve detection of one or more mutations in the nucleic acid sequence of the nucleic acid molecule obtained from the skin. Such mutations may be a substitution, a deletion, and/or an insertion of the nucleic acid sequence that results in a diseased state in the subject from which the skin sample is obtained.

In one embodiment, the nucleic acid molecule analyzed is listed in Tables 10-12 and 15. In another embodiment, the method further includes analyzing one or more nucleic acid molecules listed Tables 1-8. For example, in one embodiment, the gene analyzed is any one or more of interferon regulatory factor 6, claudin 23, melan-A, osteopetrosis associated transmembrane protein 1, RAS-like family 11 member B, actinin alpha 4, transmembrane protein 68, Glycine-rich protein (GRP3S), Transcription factor 4, hypothetical protein FLJ20489, cytochrome c somatic, transcription factor 4, Forkhead box P1, transducer of ERBB2-2, glutaminyl-peptide cyclotransferase (glutaminyl cyclase), hypothetical protein FLJ10770, selenophosphate synthetase 2, embryonal Fyn-associated substrate, Kruppel-like factor 8, Discs large homolog 5 (Drosophila), regulator of G-protein signalling 10, ADP-ribosylation factor related protein 2, TIMP metallopeptidase inhibitor 2, 5-aminoimidazole-4-carboxamide ribonucleotide formyltransferase/IMP cyclohydrolase, similar to RIKEN cDNA 5730421E18 gene, Regulator of G-protein signalling 10, Nuclear RNA-binding protein putative, tyrosinase-related protein 1, TIMP metallopeptidase inhibitor 2, Claudin 1, transcription factor 4, solute carrier family 16 (monocarboxylic acid transporters) member 6 (similar to solute carrier family 16 member 6; monocarboxylate transporter 6), or any combination thereof. In another embodiment, the nucleic acid molecule is from one or more genes listed in Tables 10-12 and 15.

Accordingly, provided herein is a method for characterizing and/or diagnosing melanoma in a subject, including obtaining a nucleic acid molecule or protein by biopsy of a skin lesion on the subject, and analyzing the nucleic acid molecule to distinguish melanoma from dysplastic nevi and/or normal pigmented skin in the subject. In this method, at least one nucleic acid molecule whose expression is informative of melanoma is detected in the epidermal sample. In one example, expression of one or more of the genes listed in Tables 1-8, 10-12, 15, or a combination thereof, is detected in the epidermal sample to characterize the melanoma. In one embodiment, the gene is any one or more of interferon regulatory factor 6, claudin 23, melan-A, osteopetrosis associated transmembrane protein 1, RAS-like family 11 member B, actinin alpha 4, transmembrane protein 68, Glycine-rich protein (GRP3S), Transcription factor 4, hypothetical protein FLJ20489, cytochrome c somatic, transcription factor 4, Forkhead box P1, transducer of ERBB2-2, glutaminyl-peptide cyclotransferase (glutaminyl cyclase), hypothetical protein FLJ10770, selenophosphate synthetase 2, embryonal Fyn-associated substrate, Kruppel-like factor 8, Discs large homolog 5 (Drosophila), regulator of G-protein signalling 10, ADP-ribosylation factor related protein 2, TIMP metallopeptidase inhibitor 2, 5-aminoimidazole-4-carboxamide ribonucleotide formyltransferase/IMP cyclohydrolase, similar to RIKEN cDNA 5730421E18 gene, Regulator of G-protein signalling 10, Nuclear RNA-binding protein putative, tyrosinase-related protein 1, TIMP metallopeptidase inhibitor 2, Claudin 1, transcription factor 4, solute carrier family 16 (monocarboxylic acid transporters) member 6 (similar to solute carrier family 16 member 6; monocarboxylate transporter 6), or any combination thereof.

The non-invasive methods of the invention involve applying an adhesive tape to a target area of skin in a manner sufficient to isolate a sample adhering to the adhesive tape, wherein the sample includes nucleic acid molecules or proteins. Typically, at least one nucleic acid molecule or protein whose expression is informative of melanoma is detected in the sample. The method of characterizing skin using tape stripping has a number of applications, such as the following: (i) disease classification/subclassification; (ii) monitoring disease severity and progression; (iii) monitoring treatment efficacy; and (iv) prediction of a particular treatment regimen. All of these applications, which themselves represent embodiments disclosed herein, preferably use non-invasive sampling to recover information that is otherwise difficult or impractical to recover (e.g., through the use of biopsies). The information may be contained in the DNA, protein, or RNA of skin cells close to the surface of the skin. In one embodiment, expression of one or more of the genes listed in Tables 1-8, 10-12, 15, or a combination thereof, is detected in the sample to characterize the sample. This exemplary method is particularly useful for distinguishing melanoma from dysplastic nevi and/or normal pigmented skin. In one embodiment, expression of one or more of the genes listed in Table 12 or 15 is detected in the sample to characterize the sample.

As such, also provided herein is a method for distinguishing solar lentigines from dysplastic nevi and/or basal cell carcinoma and/or normal pigmented skin in a subject, including applying an adhesive tape to a target area of skin in a manner sufficient to isolate a sample adhering to the adhesive tape, wherein the sample includes nucleic acid molecules. At least one nucleic acid molecule whose expression is informative of solar lentigo is detected in the sample. In one embodiment, expression of one or more of the genes listed in Tables 10-12, 15, or a combination thereof, is detected in the sample to characterize the melanoma. In another embodiment, expression of one or more of the genes listed in Table 12 or 15 is detected in the sample to characterize the solar lentigo.

Other embodiments are based in part on the discovery that for tape stripping of the skin, non-polar, pliable, adhesive tapes, especially pliable tapes with rubber adhesive, are more effective than other types of adhesive tapes. In some embodiments, the tape comprises a rubber adhesive on a polyurethane film. Using pliable tapes with rubber adhesives, as few as 10 or less tape strippings and in certain examples as few as 4 or even 1 tape stripping can be used to isolate and/or detect nucleic acid molecules from the epidermal layer of the skin.

In another embodiment, the methods of the invention provide for characterization of a skin lesion in situ, including application of a detectably labeled probe directly to a skin lesion for visual analysis. At least one nucleic acid molecule whose expression is informative of melanoma or dysplastic nevi or normal skin is detected on the skin lesion or surrounding margin or tissue using a specific probe. In one example, expression of one or more of the genes listed in Tables 1-8, 10-12, 15, or a combination thereof, is detected on the skin lesion or surrounding margin or tissue to characterize the melanoma. In one embodiment, expression of one or more of the genes listed in Tables 10-12 or 15 is detected in the sample to characterize the melanoma.

Also provided herein is a method for diagnosing a disease state by establishing a gene expression pattern of a target area suspected of being melanoma on the skin of a subject and comparing the subject's gene expression profile to a reference gene expression profile obtained from a corresponding normal skin sample. In one embodiment, the target area of the skin simultaneously expresses a plurality of genes at the protein level that are markers for melanoma. In another embodiment, the genes are listed in Tables 1-8, 10-12, 15, or any combination thereof. In another embodiment, the genes are listed in Tables 8 or 12.

In one embodiment, the method of diagnosing a disease state involves detection of one or more mutations in the nucleic acid sequence of the gene. Such mutations may be a substitution, a deletion, and/or an insertion of the nucleic acid sequence that results in a diseased state in the subject from which the skin sample is obtained. In one embodiment, the genes are listed in Tables 1-8, 10-12, 15, or any combination thereof. In another embodiment, the genes are listed in Tables 8 or 12.

In another aspect, the invention provides kits for characterizing a skin lesion in a subject. In one embodiment, the kit includes a skin sample collection device, such as a biopsy needle or an adhesive tape for non-invasive tape stripping, and one or more probes or primers that selectively bind to one or more nucleic acid molecules in any of Tables 1-8 and 10-12, 15, or to a nucleic acid or protein expression product of a nucleic acid molecule in any of Tables 1-8, 10-12, and 15. For example, in one embodiment, the gene analyzed is any one or more of interferon regulatory factor 6, claudin 23, melan-A, osteopetrosis associated transmembrane protein 1, RAS-like family 11 member B, actinin alpha 4, transmembrane protein 68, Glycine-rich protein (GRP3S), Transcription factor 4, hypothetical protein FLJ20489, cytochrome c somatic, transcription factor 4, Forkhead box P1, transducer of ERBB2-2, glutaminyl-peptide cyclotransferase (glutaminyl cyclase), hypothetical protein FLJ10770, selenophosphate synthetase 2, embryonal Fyn-associated substrate, Kruppel-like factor 8, Discs large homolog 5 (Drosophila), regulator of G-protein signalling 10, ADP-ribosylation factor related protein 2, TIMP metallopeptidase inhibitor 2, 5-aminoimidazole-4-carboxamide ribonucleotide formyltransferase/IMP cyclohydrolase, similar to RIKEN cDNA 5730421E18 gene, Regulator of G-protein signalling 10, Nuclear RNA-binding protein putative, tyrosinase-related protein 1, TIMP metallopeptidase inhibitor 2, Claudin 1, transcription factor 4, solute carrier family 16 (monocarboxylic acid transporters) member 6 (similar to solute carrier family 16 member 6; monocarboxylate transporter 6), or any combination thereof. In another embodiment, the kit includes a microarray containing at least a fragment of a gene or a nucleic acid or protein product of a gene identified in any of Tables 1-8, 10-12, 15, or any combination thereof.

In another embodiment, the kit for characterizing a skin lesion in a subject includes an applicator and one or more probes or primers that selectively bind to one or more nucleic acid molecules in any of Tables 1-8 and 10-12, 15, or to a nucleic acid or protein expression product of a nucleic acid molecule in any of Tables 1-8, 10-12, and 15. In one embodiment, the probes are detectably labeled for visual identification of expression of RNA.

BRIEF DESCRIPTION OF THE DRAWINGS

FIGS. 4A to 4D are pictorial and graphical diagrams showing the development of a gene classifier for distinguishing melanoma from atypical nevi and normal pigmented skin.

FIGS. 6A to 6E are graphical diagrams showing data from prediction analysis of the developed classifiers for distinguishing melanoma from atypical nevi and normal pigmented skin.

FIG. 9 is a graphical diagram showing data of a developed classifier for distinguishing melanoma from atypical nevi and normal pigmented skin.

FIG. 11 is a pictorial diagram describing the development of a 19-gene classifier that discriminates melanoma from atypical nevi.

FIG. 14 is a graphical diagram showing data of a developed classifier for distinguishing solar lentigines from normal pigmented skin.

DETAILED DESCRIPTION OF THE INVENTION

Figure 1A:
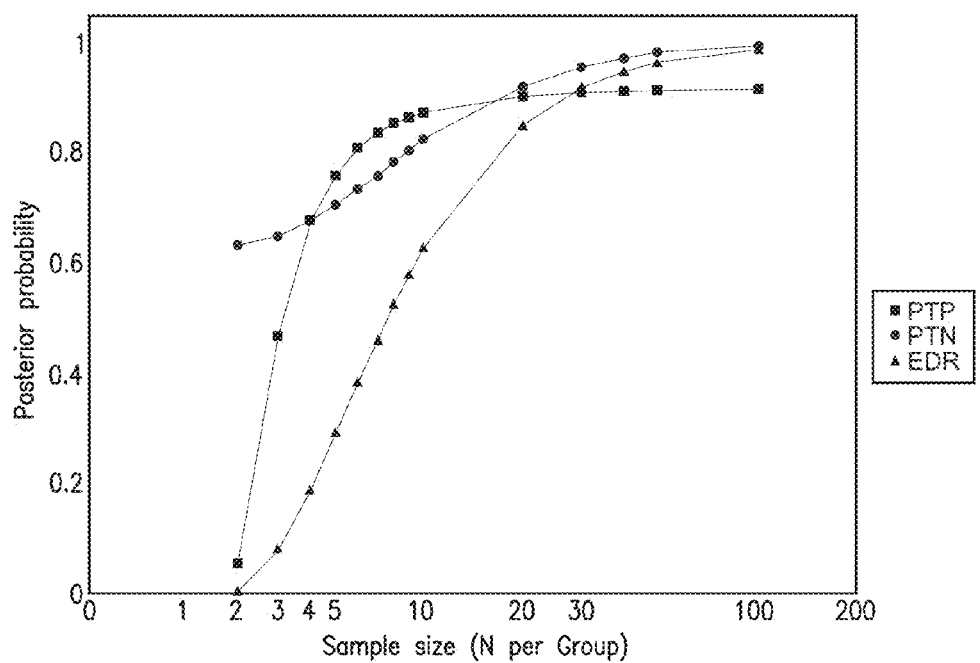
FIGS. 1A and 1B are graphical diagrams showing data from the EDR, PTP, and PTN as a function of sample size, assuming a threshold for declaring the significance of a probe/gene expression difference between nevi and primary melanoma of $p<0.05$.

The present invention is based, in part, on the discovery that analysis of nucleic acid molecules or of protein expression products of nucleic acid molecules from specific genes can be used to characterize skin lesions in a subject. Accordingly, the present invention provides methods and kits useful for detecting cancer, especially melanoma, by determining the expression profiles of one or more specific genes of interest. In addition, the present invention provides methods and kits useful for distinguishing solar lentigines from cancer by determining the expression profiles of one or more specific genes of interest.

There are two main motivations for conducting genome wide expression profiling studies in melanoma. First, melanoma is one of the best characterized carcinogenesis models for gradual progression of benign lesions to cancer: normal pigmented cells to nevi to atypical nevi to primary melanoma in situ to invasive primary melanoma to aggressive metastatic melanoma. This progression is known to correlate with distinctive chromosomal changes, and is thought to be mediated by stepwise progressive changes in gene expression, suggesting that expression profiling may identify genes responsible for tumorigenesis in melanoma. Indeed, candidate tumor genes have been identified with microarray analyses of melanoma cell lines. The second reason is that molecular characterization of tumors may allow a better staging classification of tumors and prognosis prediction. While histological characteristics such as the thickness and ulceration of tumors have some value as predictors of prognosis, there is lack of informative markers that help determine which patients will do well and which patients will have progressive disease and metastasis. Molecular markers identified in microarray experiments of tumors are already being introduced into clinical practice in the management of breast cancer. Gene expression profiling experiments in melanoma and melanoma cell lines suggest that the classification of melanoma can be improved, but studies are lacking with sufficient power to define molecular criteria for diagnosis or identify prognostic markers; the establishments of such markers would represent a major advance in melanoma care. A major reason for the lack of powerful microarray studies in melanoma is that, unlike most solid tumors, it is necessary to paraffin embed and section the whole lesion for histology, leaving no sample for RNA isolation. Although this situation is now changing, the ability to avoid biopsy until a definitive diagnosis is made would be powerful for subjects that would not normally be eligible for one or more biopsies.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

As used herein, the terms "sample" and "biological sample" refer to any sample suitable for the methods provided by the present invention. A sample of cells can be any sample, including, for example, a skin sample obtained by non-invasive tape stripping or biopsy of a subject, or a sample of the subject's bodily fluid. Thus, in one embodiment, the biological sample of the present invention is a tissue sample, e.g., a biopsy specimen such as samples from needle biopsy. In one embodiment, the term "sample" refers to any preparation derived from skin of a subject. For example, a sample of cells obtained using the non-invasive method described herein can be used to isolate nucleic acid molecules or proteins for the methods of the present invention. Samples for the present invention typically are taken from a skin lesion, which is suspected of being the result of a disease or a pathological or physiological state, such as psoriasis or dermatitis, or the surrounding margin or tissue. As used herein, "surrounding margin" or "surrounding tissue" refers to tissue of the subject that is adjacent to the skin lesion, but otherwise appears to be normal or free from lesion.

As used herein "corresponding normal cells" or "corresponding normal sample" refers to cells or a sample from a subject that is from the same organ and of the same type as the cells being examined. In one aspect, the corresponding normal cells comprise a sample of cells obtained from a healthy individual that does not have a skin lesion or skin cancer. Such corresponding normal cells can, but need not be, from an individual that is age-matched and/or of the same sex as the individual providing the cells being examined. Thus, the term "normal sample" or "control sample" refers to any sample taken from a subject of similar species that is considered healthy or otherwise not suffering from the particular disease, pathological or physiological state, or from the same subject in an area free from skin lesions. As such, a normal/standard level of RNA denotes the level of RNA present in a sample from the normal sample. A normal level of RNA can be established by combining skin samples or cell extracts taken from normal healthy subjects and determining the level of one or more RNAs present. In addition, a normal level of RNA also can be determined as an average value taken from a population of subjects that is considered to be healthy, or is at least free of a particular disease, pathological or physiological state. Accordingly, levels of RNA in subject, control, and disease samples can be compared with the standard values. Deviation between standard and subject values establishes the parameters for diagnosing or characterizing disease.

The term "skin" refers to the outer protective covering of the body, consisting of the epidermis (including the stratum corneum) and the underlying dermis, and is understood to include sweat and sebaceous glands, as well as hair follicle structures. Throughout the present application, the adjective "cutaneous" can be used, and should be understood to refer generally to attributes of the skin, as appropriate to the context in which they are used. The epidermis of the human skin comprises several distinct layers of skin tissue. The deepest layer is the stratum basalis layer, which consists of columnar cells. The overlying layer is the stratum spinosum, which is composed of polyhedral cells. Cells pushed up from the stratum spinosum are flattened and synthesize keratohyalin granules to form the stratum granulosum layer. As these cells move outward, they lose their nuclei, and the keratohyalin granules fuse and mingle with tonofibrils. This forms a clear layer called the stratum lucidum. The cells of the stratum lucidum are closely packed. As the cells move up from the stratum lucidum, they become compressed into many layers of opaque squamae. These cells are all flattened remnants of cells that have become completely filled with keratin and have lost all other internal structure, including nuclei. These squamae constitute the outer layer of the epidermis, the stratum corneum. At the bottom of the stratum corneum, the cells are closely compacted and adhere to each other strongly, but higher in the stratum they become loosely packed, and eventually flake away at the surface.

As used herein, the term "skin lesion" refers to a change in the color or texture in an area of skin. As such, "skin lesions suspected of being melanoma" are skin lesions with characteristics of malignant melanoma, which are well known to those of skill in the art, such as dermatologists and oncologists. Such lesions are sometimes raised and can have a color that is different from the color of normal skin of an individual (e.g., brown, black, red, or blue). Lesions suspected of being melanoma sometimes include a mixture of colors, are often asymmetrical, can change in appearance over time, and may bleed. A skin lesion suspected of being melanoma may be a mole or nevus. Melanoma lesions are usually, but not always, larger than 6 mm in diameter. Melanoma includes superficial spreading melanoma, nodular melanoma, acral lentiginous melanoma, and lentigo maligna melanoma. The term "lentigo maligna" refers to a precancerous lesion on the skin, especially in areas exposed to the sun, that is flat, mottled, and brownish with an irregular outline and grows slowly over a period of years. Melanoma can occur on skin that has been overexposed to the sun. Therefore, in one embodiment the skin sample is taken from an area of skin that has been overexposed to the sun.

The term "dysplastic nevus" refers to an atypical mole or a mole whose appearance is different from that of common moles. Dysplastic nevi are generally larger than ordinary moles and have irregular and indistinct borders. Their color frequently is not uniform and ranges from pink to dark brown; they usually are flat, but parts may be raised above the skin surface. Dysplastic naevus can be found anywhere, but are most common on the trunk of a subject.

The term "cancer" as used herein, includes any malignant tumor including, but not limited to, carcinoma and sarcoma. Cancer arises from the uncontrolled and/or abnormal division of cells that then invade and destroy the surrounding tissues. As used herein, "proliferating" and "proliferation" refer to cells undergoing mitosis. As used herein, "metastasis" refers to the distant spread of a malignant tumor from its sight of origin. Cancer cells may metastasize through the bloodstream, through the lymphatic system, across body cavities, or any combination thereof. The term "cancerous cell" as provided herein, includes a cell afflicted by any one of the cancerous conditions provided herein. The term "carcinoma" refers to a malignant new growth made up of epithelial cells tending to infiltrate surrounding tissues, and to give rise to metastases. The term "melanoma" refers to a malignant tumor of melanocytes which are found predominantly in skin but also in bowel and the eye. "Melanocytes" refer to cells located in the bottom layer, the basal lamina, of the skin's epidermis and in the middle layer of the eye. Thus, "melanoma metastasis" refers to the spread of melanoma cells to regional lymph nodes and/or distant organs (e.g., liver, brain, breast, prostate, etc.).

The term "basal cell carcinoma" or "BCC" refers to a slow-growing neoplasm that is locally invasive but rarely metastasizes. It is derived from basal cells, the deepest layer of epithelial cells of the epidermis or hair follicles. BCC is a common skin cancer that is often associated with overexposure to sunlight.

The term "solar lentigo" or "solar lentigines," also known as a sun-induced freckle or senile lentigo, is a dark (hyperpigmented) lesion caused by natural or artificial ultraviolet (UV) light. Solar lentigines may be single or multiple. Solar lentigines are benign, but they do indicate excessive sun exposure, a risk factor for the development of skin cancer. The lesions tend to increase in number with age, making them common among the middle age and older population. They can vary in size from about 0.2 to 2.0 cm. These flat lesions usually have discrete borders, are dark in color, and have an irregular shape.

As used herein, the term "gene" refers to a linear sequence of nucleotides along a segment of DNA that provides the coded instructions for synthesis of RNA, which, when translated into protein, leads to the expression of hereditary character. As such, the term "skin marker" or "biomarker" refers to a gene whose expression level is different between skin surface samples at the site of malignant melanoma and skin surface samples of normal skin or a lesion, which is benign, such as a benign nevus. Therefore, expression of a melanoma skin marker of the invention is related to, or indicative of, melanoma. Many statistical techniques are known in the art, which can be used to determine whether a statistically significant difference in expression is observed at a high (e.g., 90% or 95%) confidence level. As such, an increase or decrease in expression of these genes is related to and can characterize malignant melanoma. In one embodiment, there is at least a two-fold difference in levels between skin sample near the site of malignant melanoma and skin samples from normal skin.

As used herein, the term "nucleic acid molecule" means DNA, RNA, single-stranded, double-stranded or triple stranded and any chemical modifications thereof. Virtually any modification of the nucleic acid is contemplated. A "nucleic acid molecule" can be of almost any length, from 10, 20, 30, 40, 50, 60, 75, 100, 125, 150, 175, 200, 225, 250, 275, 300, 400, 500, 600, 700, 800, 900, 1000, 1500, 2000, 2500, 3000, 3500, 4000, 4500, 5000, 6000, 7000, 8000, 9000, 10,000, 15,000, 20,000, 30,000, 40,000, 50,000, 75,000, 100,000, 150,000, 200,000, 500,000, 1,000,000, 1,500,000, 2,000,000, 5,000,000 or even more bases in length, up to a full-length chromosomal DNA molecule. For methods that analyze expression of a gene, the nucleic acid isolated from a sample is typically RNA.

Micro-RNAs (miRNA) are small single stranded RNA molecules an average of 22 nucleotides long that are involved in regulating mRNA expression in diverse species including humans (reviewed in Bartel 2004). The first report of miRNA was that of the lin-4 gene, discovered in the worm *C. elegans* (Lee, Feinbaum et al. 1993). Since then hundreds of miRNAs have been discovered in flies, plants and mammals. miRNAs regulate gene expression by binding to the 3'-untranslated regions of mRNA and catalyze either i) cleavage of the mRNA; or 2) repression of translation. The regulation of gene expression by miRNAs is central to many biological processes such as cell development, differentiation, communication, and apoptosis (Reinhart, Slack et al. 2000; Baehrecke 2003; Brennecke, Hipfner et al. 2003; Chen, Li et al. 2004). Recently it has been shown that miRNA are active during embryogenesis of the mouse epithelium and play a significant role in skin morphogenesis (Yi, O'Carroll et al. 2006).

Given the role of miRNA in gene expression it is clear that miRNAs will influence, if not completely specify the relative amounts of mRNA in particular cell types and thus determine a particular gene expression profile (i.e., a population of specific mRNAs) in different cell types. In addition, it is likely that the particular distribution of specific miRNAs in a cell will also be distinctive in different cell types. Thus, determination of the miRNA profile of a tissue may be used as a tool for expression profiling of the actual mRNA population in that tissue. Accordingly, miRNA levels and/or detection of miRNA mutations are useful for the purposes of disease detection, diagnosis, prognosis, or treatment-related decisions (i.e., indicate response either before or after a treatment regimen has commenced) or characterization of a particular disease in the subject.

As used herein, the term "protein" refers to at least two covalently attached amino acids, which includes proteins, polypeptides, oligopeptides and peptides. A protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration.

A "probe" or "probe nucleic acid molecule" is a nucleic acid molecule that is at least partially single-stranded, and that is at least partially complementary, or at least partially substantially complementary, to a sequence of interest. A probe can be RNA, DNA, or a combination of both RNA and DNA. It is also within the scope of the present invention to have probe nucleic acid molecules comprising nucleic acids in which the backbone sugar is other that ribose or deoxyribose. Probe nucleic acids can also be peptide nucleic acids. A probe can comprise nucleolytic-activity resistant linkages or detectable labels, and can be operably linked to other moieties, for example a peptide.

A single-stranded nucleic acid molecule is "complementary" to another single-stranded nucleic acid molecule when it can base-pair (hybridize) with all or a portion of the other nucleic acid molecule to form a double helix (double-stranded nucleic acid molecule), based on the ability of guanine (G) to base pair with cytosine (C) and adenine (A) to base pair with thymine (T) or uridine (U). For example, the nucleotide sequence 5'-TATAC-3' is complementary to the nucleotide sequence 5'-GTATA-3'.

The term "antibody" as used in this invention is meant to include intact molecules of polyclonal or monoclonal antibodies, as well as fragments thereof, such as Fab and F(ab')$_2$, Fv and SCA fragments which are capable of binding an epitopic determinant. The term "specifically binds" or "specifically interacts," when used in reference to an antibody means that an interaction of the antibody and a particular epitope has a dissociation constant of at least about $1\times10^{-6}$, generally at least about $1\times10^{-7}$, usually at least about $1\times10^{-8}$, and particularly at least about $1\times10^{-9}$ or $1\times10^{-10}$ or less.

As used herein "hybridization" refers to the process by which a nucleic acid strand joins with a complementary strand through base pairing. Hybridization reactions can be sensitive and selective so that a particular sequence of interest can be identified even in samples in which it is present at low concentrations. In an in vitro situation, suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature. For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 mg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

As used herein, the term "mutation" refers to a change in the genome with respect to the standard wild-type sequence. Mutations can be deletions, insertions, or rearrangements of nucleic acid sequences at a position in the genome, or they can be single base changes at a position in the genome, referred to as "point mutations." Mutations can be inherited, or they can occur in one or more cells during the lifespan of an individual.

As used herein, the term "kit" or "research kit" refers to a collection of products that are used to perform a biological research reaction, procedure, or synthesis, such as, for example, a detection, assay, separation, purification, etc., which are typically shipped together, usually within a common packaging, to an end user.

As used herein, the term "ameliorating" or "treating" means that the clinical signs and/or the symptoms associated with the cancer or melanoma are lessened as a result of the actions performed. The signs or symptoms to be monitored will be characteristic of a particular cancer or melanoma and will be well known to the skilled clinician, as will the methods for monitoring the signs and conditions. Thus, a "treatment regimen" refers to any systematic plan or course for treating a disease or cancer in a subject.

Samples from a tissue can be isolated by any number of means well known in the art. Invasive methods for isolating a sample include, but are not limited to the use of needles or scalpels, for example during biopsies of various tissues. Non-invasive methods for isolating a sample include, but are not limited to tape-stripping and skin scraping.

Accordingly, in one embodiment, the present invention employs a non-invasive tape stripping technology to obtain samples of suspicious lesions. As such, DNA microarray assays are used to create a non-invasive diagnostic for melanoma and/or distinguishing melanoma from solar lentigo. Tape-stripping removes superficial cells from the surface of the skin as well as adnexal cells. Small amounts of nucleic acid molecules isolated from tape-stripped cells can be amplified and used for microarray analyses and quantitative PCR. In addition, proteins obtained from the lysed cells may be quantitated for diagnosis of disease. Consequently, tape-stripping is a non-invasive diagnostic method, which does not interfere with subsequent histological analyses, thereby bypassing a major limitation to current expression profiling studies on melanoma. While tape stripping will primarily sample superficial cells from the epidermis, this method holds great promise in the diagnoses and prognosis prediction in pigmented lesions for the following reasons: First, in contrast to benign nevi, in many melanomas the pigmented cells migrate into the epidermis and/or adnexa. Consequently, this feature may help differentiate benign pigmented lesions from melanomas based on tape stripping. Second, there are changes in the dermis and epidermis adjacent to melanoma. The epidermal hyperplasia overlying melanoma seems to correlate with both angiogenesis and metastatic potential; these changes are expected to be sampled with the tape stripping method. Finally, some advanced melanomas do reach the surface of the skin and melanoma cancer cells would be sampled directly by the tape stripping. In addition tape stripping is useful in the care of patients with multiple pigmented lesions where it is unpractical to biopsy each and every lesion. Accordingly, the present invention demonstrates that stratum corneum RNA, harvested by tape stripping with Epidermal Genetic Information Retrieval (EGIR) (see U.S. Pat. No. 6,949,338, incorporated herein by reference), can be used to distinguish melanoma from dysplastic nevi in suspicious pigmented lesions.

As indicated, the tape stripping methods provided herein typically involve applying an adhesive tape to the skin of a subject and removing the adhesive tape from the skin of the subject one or more times. In certain examples, the adhesive tape is applied to the skin and removed from the skin about one to ten times. Alternatively, about ten adhesive tapes can be sequentially applied to the skin and removed from the skin.

These adhesive tapes are then combined for further analysis. Accordingly, an adhesive tape can be applied to and removed from a target site 10, 9, 8, 7, 6, 5, 4, 3, 2, or 1 time, and/or 10, 9, 8, 7, 6, 5, 4, 3, 2, or 1 adhesive tape can be applied to and removed from the target site. In one illustrative example, the adhesive tape is applied to the skin between about one and eight times, in another example, between one and five times, and in another illustrative example the tape is applied and removed from the skin four times.

The rubber based adhesive can be, for example, a synthetic rubber-based adhesive. The rubber based adhesive in illustrative examples, has high peel, high shear, and high tack. For example, the rubber based adhesive can have a peak force tack that is at least 25%, 50%, or 100% greater than the peak force tack of an acrylic-based tape such as D-SQUAME™. D-SQUAME™ has been found to have a peak force of 2 Newtons, wherein peak force of the rubber based adhesive used for methods provided herein, can be 4 Newtons or greater. Furthermore, the rubber based adhesive can have adhesion that is greater than 2 times, 5 times, or 10 times that of acrylic based tape. For example, D-SQUAME™ has been found to have adhesion of 0.0006 Newton meters, whereas the rubber based tape provided herein can have an adhesion of about 0.01 Newton meters using a texture analyzer. Furthermore, in certain illustrative examples, the adhesive used in the methods provided herein has higher peel, shear and tack than other rubber adhesives, especially those used for medical application and Duct tape.

Virtually any size and/or shape of adhesive tape and target skin site size and shape can be used and analyzed, respectively, by the methods of the present invention. For example, adhesive tape can be fabricated into circular discs of diameter between 10 millimeters and 100 millimeters, for example between 15 and 25 millimeters in diameter. The adhesive tape can have a surface area of between about 50 $mm^2$ and 1000 $mm^2$, between about 100 $mm^2$ to 500 $mm^2$ or about 250 $mm^2$ In another embodiment, the sample is obtained by means of an invasive procedure, such as biopsy. Biopsies may be taken instead of or after tape stripping and are subjected to standard histopathologic analysis. Analysis of biopsy samples taken simultaneously with tape stripping samples may then be correlated with the data generated from one or more of analysis of selected lesion RNA samples by DNA microarray, correlation of gene expression data with histopathology, and creation of a candidate expression classifier for diagnosis of melanoma.

As used herein, "biopsy" refers to the removal of cells or tissues for analysis. There are many different types of biopsy procedures known in the art. The most common types include: (1) incisional biopsy, in which only a sample of tissue is removed; (2) excisional biopsy, in which an entire lump or suspicious area is removed; and (3) needle biopsy, in which a sample of tissue or fluid is removed with a needle. When a wide needle is used, the procedure is called a core biopsy. When a thin needle is used, the procedure is called a fine-needle aspiration biopsy. Other types of biopsy procedures include, but are not limited to, shave biopsy, punch biopsy, curettage biopsy, and in situ biopsy. In another embodiment, the skin sample is obtained by scraping the skin with an instrument to remove one or more nucleic acid molecules from the skin.

The skin sample obtained using the tape stripping method includes, epidermal cells including cells comprising adnexal structures. In certain illustrative examples, the sample includes predominantly epidermal cells, or even exclusively epidermal cells. The epidermis consists predominantly of keratinocytes (>90%), which differentiate from the basal layer, moving outward through various layers having decreasing levels of cellular organization, to become the cornified cells of the stratum corneum layer. Renewal of the epidermis occurs every 20-30 days in uninvolved skin. Other cell types present in the epidermis include melanocytes, Langerhans cells, and Merkel cells. As illustrated in the Examples herein, the tape stripping method of the present invention is particularly effective at isolating epidermal samples.

Nucleic acid molecules can also be isolated by lysing the cells and cellular material collected from the skin sample by any number of means well known to those skilled in the art. For example, a number of commercial products available for isolating polynucleotides, including but not limited to, RNeasy™ (Qiagen, Valencia, Calif.) and TriReagent™ (Molecular Research Center, Inc, Cincinnati, Ohio) can be used. The isolated polynucleotides can then be tested or assayed for particular nucleic acid sequences, including a polynucleotide encoding a cytokine. Methods of recovering a target nucleic acid molecule within a nucleic acid sample are well known in the art, and can include microarray analysis.

Nucleic acid molecules may be analyzed in any number of ways known in the art. For example, the presence of nucleic acid molecules can be detected by DNA-DNA or DNA-RNA hybridization or amplification using probes or fragments of the specific nucleic acid molecule. Nucleic acid amplification based assays involve the use of oligonucleotides or oligomers based on the nucleic acid sequences to detect transformants containing the specific DNA or RNA.

In one embodiment, analysis of the nucleic acid molecules includes genetic analysis is to determine the nucleotide sequence of a gene. Since a difference in length or sequence between DNA fragments isolated from a sample and those of known sequences are due to an insertion, deletion, or substitution of one or more nucleotides, the determination of nucleic acid sequences provides information concerning mutations which have absolute influence on the physiology of the disease state in the subject. These mutations may also include transposition or inversion and are difficult to detect by other techniques than direct sequencing. For example, it has recently been shown that the presence of the c-kit-activating mutation, L576P, is indicative of malignant melanomas (see Table 1). Accordingly, the methods of the present invention may be used to detect genetic mutations in one or more genes listed in Tables 1-8 and 10-12 for diagnosis and/or characterization of a skin lesion in a subject.

A variety of protocols for detecting and measuring the expression of nucleic acid molecules, using either polyclonal or monoclonal antibodies specific for the protein expression product are known in the art. Examples include enzyme-linked immunosorbent assay (ELISA), radioimmunoassay (RIA), and fluorescence activated cell sorting (FACS). These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211-1216).

In another embodiment, antibodies that specifically bind the expression products of the nucleic acid molecules of the invention may be used to characterize the skin lesion of the subject. The antibodies may be used with or without modification, and may be labeled by joining them, either covalently or non-covalently, with a reporter molecule.

A wide variety of labels and conjugation techniques are known by those skilled in the art and may be used in various nucleic acid and amino acid assays. Means for producing labeled hybridization or PCR probes for detecting sequences related to the nucleic acid molecules of Tables 1-8, 10-12, and 15 include oligolabeling, nick translation, end-labeling or PCR amplification using a labeled nucleotide. Alternatively, the nucleic acid molecules, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

PCR systems usually use two amplification primers and an additional amplicon-specific, fluorogenic hybridization probe that specifically binds to a site within the amplicon. The probe can include one or more fluorescence label moieties. For example, the probe can be labeled with two fluorescent dyes: 1) a 6-carboxy-fluorescein (FAM), located at the 5'-end, which serves as reporter, and 2) a 6-carboxy-tetramethyl-rhodamine (TAMRA), located at the 3'-end, which serves as a quencher. When amplification occurs, the 5'-3' exonuclease activity of the Taq DNA polymerase cleaves the reporter from the probe during the extension phase, thus releasing it from the quencher. The resulting increase in fluorescence emission of the reporter dye is monitored during the PCR process and represents the number of DNA fragments generated. In situ PCR may be utilized for the direct localization and visualization of target nucleic acid molecules and may be further useful in correlating expression with histopathological finding.

Means for producing specific hybridization probes for nucleic acid molecules of the invention include the cloning of the nucleic acid sequences into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as $^{32}P$ or $^{35}S$, or enzymatic labels, such as alkaline phosphatase coupled to the probe via avidin/biotin coupling systems, and the like.

In order to provide a basis for the diagnosis or characterization of disease associated with expression of the nucleic acid molecules of the invention, a normal or standard profile for expression is established. Standard hybridization may be quantified by comparing the values obtained from subjects of known skin characterization (e.g., from subjects either having melanoma, having dysplastic nevi, and/or having solar lentigines). Standard values obtained from such samples may be compared with values obtained from samples from subjects having skin lesions that are suspected of being melanoma. Deviation between standard and subject values is used to establish the presence of disease.

Accordingly, in one aspect of the invention, a non-invasive sampling method is provided for the characterization of skin lesion on the skin. In one embodiment, a sample set of pigmented skin lesions is created. Each sample consists of nucleic acid molecules recovered by tape stripping or biopsy sample of the superficial epidermis overlying the lesion. In addition to tape striping, a standard biopsy of the same lesion may also be performed, along with accompanying histology and diagnosis. Nucleic acid molecules recovered by tape stripping the superficial epidermis of normal skin will serve as a negative control.

In another aspect, the invention provides a method of distinguishing melanoma from solar lentigo and/or dysplastic nevi and/or normal pigmented skin in a subject. In one embodiment, the method includes analyzing a nucleic acid molecule from one or more genes listed in any of Tables 1-8, 10-12, 15, or any combination thereof. A target area of the skin of a subject that suspected of being melanoma is assayed for expression of a large number of genes. Analyzing expression includes any qualitative or quantitative method for detecting expression of a gene, many of which are known in the art. The method can include analyzing expression of specific markers by measuring expression of the markers using a quantitative method, or by using a qualitative method. Non-limiting methods for analyzing polynucleotides and polypeptides are discussed below.

In another aspect, the invention provides a method of distinguishing solar lentigines from dysplastic nevi and/or basal cell carcinoma and/or normal pigmented skin in a subject. In one embodiment, the method includes analyzing a nucleic acid molecule from one or more genes listed in any of Tables 1-8, 10-12, 15, or any combination thereof. A target area of the skin of a subject that suspected of being melanoma is assayed for expression of a large number of genes. Analyzing expression includes any qualitative or quantitative method for detecting expression of a gene, many of which are known in the art. The method can include analyzing expression of specific markers by measuring expression of the markers using a quantitative method, or by using a qualitative method. Non-limiting methods for analyzing polynucleotides and polypeptides are discussed below Methods of analyzing expression of a gene of the present invention can utilize a microarray, or other miniature high-throughput technology, for detecting expression of one or more gene products. Quantitative measurement of expression levels using such microarrays is also known in the art, and typically involves a modified version of a traditional method for measuring expression as described herein. For example, such quantitation can be performed by measuring a phosphor image of a radioactive-labeled probe binding to a spot of a microarray, using a phosphor imager and imaging software.

In a related aspect, the invention provides a method for diagnosing various disease states in a subject by identifying new diagnostic markers, specifically the classification and diagnosis of melanoma. In addition, the invention provides a method for distinguishing solar lentigines from dysplastic nevi and/or lentigo maligna and/or normal skin. Thus, the invention provides a method for diagnosing various disease states in a subject by identifying new diagnostic markers, specifically the classification and diagnosis of melanoma. By identifying gene sets that are unique to a given state, these differences in the genetic expression can be utilized for diagnostic purposes. In one embodiment, the nucleic acid molecule is RNA, including messenger RNA (mRNA) that is isolated from a sample from the subject. Up-regulated and down-regulated gene sets for a given disease state may be subsequently combined. The combination enables those of skill in the art to identify gene sets or panels that are unique to a given disease state. Such gene sets are of immense diagnostic value as they can be routinely used in assays that are simpler than microarray analysis (for example "real-time" quantitative PCR). Such gene sets also provide insights into pathogenesis and targets for the design of new drugs.

A reference database containing a number of reference projected profiles is also created from skin samples of subjects with known states, such as normal (i.e., non-melanoma) and various skin cancer disease states and/or pigmented non-cancer states. The projected profile is then compared with the reference database containing the reference projected profiles. If the projected profile of the subject matches best with the profile of a particular disease state in the database, the subject is diagnosed as having such disease state. Various computer systems and software can be utilized for implementing the analytical methods of this invention and are apparent to one of skill in the art. Exemplary software programs include, but are not limited to, Cluster & TreeView (Stanford, URLs: rana.lbl.gov or microarray.org), GeneCluster (MIT/Whitehead Institute, URL: MPR/GeneCluster/GeneCluster.html), Array Explorer (SpotFire Inc, URL: spotfire.com/products/scicomp.asp#SAE) and GeneSpring (Silicon Genetics Inc, URL: sigenetics.com/Products/GeneSpring/index.html) (for computer systems and software, see also U.S. Pat. No. 6,203,987, incorporated herein by reference).

In another aspect, the methods of the present invention involve in situ analysis of the skin lesion for characterization thereof. For in situ methods, nucleic acid molecules do not need to be isolated from the subject prior to analysis. In one embodiment, detectably labeled probes are contacted with a cell or tissue of a subject for visual detection of expressed RNA to characterize the skin lesion.

In another aspect, the methods of the present invention can also be useful for monitoring the progression of diseases and the effectiveness of treatments. For example, by comparing the projected profile prior to treatment with the profile after treatment. In one embodiment, the method characterizes a cancer as melanoma metastasis based on analysis of one or more nucleic acid molecules from Tables 1-8. In another embodiment, the method characterizes a solar lentigo based on analysis of one or more nucleic acid molecules from Tables 10-12 and 15. It is known that in many cases, by the time a diagnosis of melanoma is established in a subject, metastasis has already occurred since melanomas contain multiple cell populations characterized by diverse growth rates, karyotypes, cell-surface properties, antigenicity, immunogenicity, invasion, metastasis, and sensitivity to cytotoxic drugs or biologic agents. Thus, the present invention may be used to characterize cancer of an organ as having metastasized from melanoma.

In a related aspect, the methods of the present invention can also be useful for determining an appropriate treatment regimen for a subject having a specific cancer or melanoma. In another related aspect, the methods of the present invention can also be useful for determining an appropriate treatment regimen for a subject having solar lentigo. Thus, the methods of the invention are useful for providing a means for practicing personalized medicine, wherein treatment is tailored to a subject based on the particular characteristics of the cancer or skin lesion in the subject. The method can be practiced, for example, by first determining whether the skin lesion is melanoma or solar lentigo, as described above.

The sample of cells examined according to the present method can be obtained from the subject to be treated, or can be cells of an established cancer cell line of the same type as that of the subject. In one aspect, the established cell line can be one of a panel of such cell lines, wherein the panel can include different cell lines of the same type of disease and/or different cell lines of different diseases associated with expression of the genes of interest. Such a panel of cell lines can be useful, for example, to practice the present method when only a small number of cells can be obtained from the subject to be treated, thus providing a surrogate sample of the subject's cells, and also can be useful to include as control samples in practicing the present methods.

Once disease and/or skin lesion characterization is established and a treatment protocol is initiated, the methods of the invention may be repeated on a regular basis to monitor the expression profiles of the genes of interest in the subject. The results obtained from successive assays may be used to show the efficacy of treatment over a period ranging from several days to months. Accordingly, another aspect of the invention is directed to methods for monitoring a therapeutic regimen for treating a subject having skin cancer. A comparison of the expression profile or mutations in the nucleic acid sequence of the nucleic acid molecule prior to and during therapy will be indicative of the efficacy of the therapy. Therefore, one skilled in the art will be able to recognize and adjust the therapeutic approach as needed.

The efficacy of a therapeutic regimen for treating a cancer over time can be identified by an absence of symptoms or clinical signs of the particular cancer in a subject at the time of onset of therapy. In subjects diagnosed as having the particular cancer, the efficacy of a method of the invention can be evaluated by measuring a lessening in the severity of the signs or symptoms in the subject or by the occurrence of a surrogate end-point for the disorder.

In addition, such methods may help identify an individual as having a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

When performed in a high throughput (or ultra-high throughput) format, the methods of the invention can be performed on a solid support (e.g., a microtiter plate, a silicon wafer, or a glass slide), wherein cell samples and/or genes of interest are positioned such that each is delineated from each other (e.g., in wells). Any number of samples or genes (e.g., 96, 1024, 10,000, 100,000, or more) can be examined in parallel using such a method, depending on the particular support used. Where samples are positioned in an array (i.e., a defined pattern), each sample in the array can be defined by its position (e.g., using an x-y axis), thus providing an "address" for each sample. An advantage of using an addressable array format is that the method can be automated, in whole or in part, such that cell samples, reagents, genes of interest, and the like, can be dispensed to (or removed from) specified positions at desired times, and samples (or aliquots) can be monitored, for example, for expression products and/or mutations in the nucleic acid sequence of the nucleic acid molecules from any one of the genes listed in Tables 1-8, 10-12, and 15.

Thus, the microarray can be used to monitor the expression level of large numbers of genes simultaneously (to produce a transcript image), and to identify genetic variants, mutations and polymorphisms. Polynucleotides used in the microarray may be oligonucleotides that are specific to a gene or genes of interest in which at least a fragment of the sequence is known or that are specific to one or more unidentified cDNAs which are common to a particular cell type, developmental or disease state. In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

According to another aspect of the present invention, a kit is provided that is useful for detecting cancer in a cell or tissue, e.g., using the methods provided by the present invention for characterizing a skin lesion in a subject. In one embodiment, a kit of the invention includes a skin sample collection device and one or more probes or primers that selectively bind to one or more of the nucleic acid molecules in any of Tables 1-8, 10-12, and 15. In another embodiment, the kit includes one or more applicators in addition to or instead of the skin sample collection device. Such applicators are useful for in situ analysis of gene expression on the skin of a subject. For example, an applicator may be used to apply detectably labeled probes for visual detection of expressed RNA to characterize the skin lesion.

In another embodiment, a kit of the invention includes a probe that binds to a portion of a nucleic acid molecule in any of Tables 1-8, 10-12, and 15. In another embodiment, the kit further includes a microarray that contains at least a fragment of a gene or a nucleic acid molecule or a protein product of any one of the genes listed in Tables 1-8, 10-12, and 15. In some embodiments, many reagents may be provided in a kit of the invention, only some of which should be used together in a particular reaction or procedure. For example, multiple primers may be provided, only two of which are needed for a particular application.

In another embodiment, the kit of the invention provides a compartmentalized carrier including a first container containing a pair of primers. The primers are typically a forward primer that selectively binds upstream of a gene on one strand, and a reverse primer that selectively binds upstream of a gene on a complementary strand. Optionally the kits of the present invention can further include an instruction insert, e.g., disclosing methods for sample collection using the sample collection device and/or exemplary gene expression profiles for comparison with the expression profile of the sample taken from the subject.

The following examples are provided to further illustrate the advantages and features of the present invention, but are not intended to limit the scope of the invention. While they are typical of those that might be used, other procedures, methodologies, or techniques known to those skilled in the art may alternatively be used.

Example 1

RNA Quantitation and Profiling

The core hypothesis of this study is that epidermal cells overlying in situ or invasive melanoma, including but not limited to the stratum corneum, stratum lucidum, and stratum granulosum, can be recovered by adhesive means and that the quality and quantity of gene expression in the form of RNA contained within this sample is differently expressed from from a nearby epidermal sample, i.e. that the sampled RNA is diagnostic because of the underlying melanoma. It has been previously shown that changes in gene expression of specific genes are detectable in epidermal hyperplasia overlying cutaneous human melanoma samples obtained from surgical specimens of the epidermis (McCarty et al., 2003).

The present study is divided into two separate phases, a sample collection and characterization phase (phase 1) and an RNA profiling phase (phase 2). In phase 1 the tape stripped specimens and biopsied sample collections were performed by the principal investigator or trained individuals delegated by the principal investigator to obtain the biopsy sample at various sites. All biopsies are subject to standard histopathologic analysis. The RNA profiling phase (Phase 2), includes, but is not limited to RNA purification and hybridization to DNA microarrays for gene expression profiling.

Materials and Reagents.

Adhesive tape was purchased from Adhesives Research (Glen Rock, Pa.) in bulk rolls. These rolls were custom fabricated into small circular discs, 17 millimeters in diameter, by Diagnostic Laminations Engineering (Oceanside, Calif.). Human spleen total RNA was purchased from Ambion (catalogue #7970; Austin, Tex.). RNeasy RNA extraction kit was purchased from Qiagen (Valencia, Calif.). Reverse transcriptase, PCR primers and probes, and TaqMan Universal Master Mix, which included all buffers and enzymes necessary for the amplification and fluorescent detection of specific cDNAs, were purchased from Applied Biosystems (Foster City, Calif.). MELT total nucleic acid isolation system was purchased from Ambion (Austin, Tex.).

RNA Isolation.

RNA was extracted from tapes using either pressure cycling technology (PCT; Garrett, Tao et al. 2002; Schumacher, Manak et al. 2002) or MELT total nucleic acid system. Tapes were extracted in pairs by insertion into a PULSE™ tube (Pressure Biosciences, Gaithersburg, Md.) with 1.2 mls of buffer RLT (supplied in the Qiagen RNeasy kit). PULSE™ tubes were inserted into the PCT-NEP2017 pressure cycler and the sample was extracted using the following parameters: room temperature; 5 pressure cycles of 35 Kpsi with pressure held for 20 seconds at the top and bottom of each cycle. After pressure extraction the buffer was removed and used to process the remaining tapes used to strip that site; the buffer was then processed according to the standard Qiagen RNeasy protocol for the collection of larger RNAs (>200 nucleotides) by application to a purification column to which large RNA molecules (i.e. mRNAs) bind, while the column flow-through is saved for microRNA purification. The column flow-through, which contains miRNA separated from mRNA, is processed according to the Qiagen miRNA purification procedure (on the world wide web at qiagen.com/literature/protocols/pdf/RY20.pdf) to purify the microRNA. RNA from the 2 sites stripped on each subject was pooled to create a single sample from each subject.

RNA Isolation Using MELT Total Nucleic Acid Protocol.

Tapes were extracted in a 2 ml eppendorf tube with 192 ml MELT buffer plus 8 ml of MELT cocktail and vortexed for 10 minutes at room temperature. The MELT lysates were transferred to the dispensed binding bead master mix after spinning down for 3 minutes at >10,000×g and washed with 300 ml of Wash Solution 1 and 2. RNAs were eluted in 100 ml of elution solution.

Quantitation of mRNA.

Experimental data is reported as the number of PCR cycles required to achieve a threshold fluorescence for a specific cDNA and is described as the "$C_t$" value (Gibson, Heid et al. 1996; Heid, Stevens et al. 1996; AppliedBiosystems 2001). Quantitation of total RNA mass was performed as previously described (Wong, Tran et al. 2004). Briefly, RNA mass recovered from tapes is determined by using quantitative RT-PCR with reference to a standard curve ($C_{t,\ actin}$ vs. log [RNA];

AppliedBiosystems 2001) created from commercially purchased human spleen total RNA. The average of 6 replicate $C_{t, actin}$ values was used to calculate the concentration of RNA in a sample with reference to the standard curve.

RNA Amplification and Array Hybridization.

RNA was isolated by the Multi-Enzymatic Liquefaction of Tissue method (Ambion, Austin, Tex.) and amplified using the WT-Ovation pico amplification system (NuGen, San Carlos, Calif.). The amplified RNA was hybridized to Affymetrix U133 plus 2.0 microarray and data were processed and analyzed using R from Bioconductor.

Sample Size.

Sample size calculations are presented in Example 2. This analysis predicts that in order to find 25-40 genes with high predictive value (p<0.001) for discriminating benign nevi from melanoma then approximately 30 melanomas and 30 non-melanoma lesions are needed.

Preprocessing GeneChip Data.

The image files from scanning the Affymetrix GeneChips with the Affymetrix series 3000 scanner will be converted using GCOS software (Affymetrix) to "CEL" format files. Normalization of CEL files will be carried out using software from the Bioconductor suite (on the world wide web at bioconductor.org). In particular, a robust multiarray analysis with adjustments for optical noise and binding affinities of oligonucleotide probes (Wu et al., 2006; and Wu et al., 2004) as implemented by the function "just.gcrma" in the "gcrma" package will be used to normalize the GeneChip Data.

Statistical Approach for Microarray Data Analysis.

Two generic statistical problems are addressed in this proposal: (i) identifying genes that are differentially expressed in different classes of lesions (i.e. melanoma versus non-melanoma lesions) and (ii) forming (and evaluating) rules for classification of melanoma and non-melanoma lesions into groups based on gene expression data.

The most important grouping divides melanoma from non-melanoma on the basis of biopsy results. The methods that will be used to address the problems identified above are now standard in the statistical evaluation of microarray data (for reviews see Smyth et al., 2003; and Lee, 2004)). These methods have been applied by others to data from Affymetrix arrays to study gene expression in prostate cancer (Stuart et al., 2004), to characterize changes in gene expression subsequent to HIV infection (Mitchell et al., 2003), and to develop a high throughput genotyping platform (Wolyn et al., 2004; and Borevitz et al., 2003). For identifying differentially expressed genes, permutation based estimates of false discovery rates (reviewed in Efron et al., 2002) are preferred. Scripts for the R quantitative programming environment were developed to implement these methods in our previous work, but will likely use or adapt the "siggenes" package from the Bioconductor suite in this project. The development of classification rules will rely on resampling methods (k-fold cross-validation, the 632 plus bootstrap, and/or bagging (Hastie et al., 2001) applied to the naive Bayes classifier and the nearest shrunken centroid classifier (Tibshirani et al., 2002) and the support vector machine (SVM) which both performed well in classifying prostate tissues as malignant or benign, used in our previous work. The implementation likely to be used is to perform k-fold cross-validation. Within each of the k train/test cycles an initial screen of the training data for differentially expressed genes is performed and genes are ordered according to their posterior probability of differential expression. Naive Bayes and nearest shrunken centroid classifiers based on the r genes with the highest posterior probability of differential expression are formed choosing enough values of r between 1 and 1024 to allow accurate interpolation of the classification error rate. The "one se rule" (Brieman et al., 1984) is applied to the error rates for the test sets to choose the classifier that minimizes the error rate. For SVM, an internal 632+ bootstrap is applied to each training sample to select the number of genes to be used in forming the classifier. The "1 se rule" error rates from the k test sets are used to characterize the classification accuracy.

In addition to the use of univariate and multivariate statistical analysis tools, sophisticated bioinformatic analysis approaches will help make sense of possible biological links between the genes found to be differentially expressed between, e.g., melanoma and non-melanoma samples. These approaches will focus on the analysis of genetic networks and pathways (Edelman et al., 2006; Kong et al., 2006; and Pang et al., 2006) and have been implemented in software packages such as Ingenuity (on the world wide web at ingenuity.com) and MetaCore (on the world wide web at genego.com). The identification of the biological links between genes that emerge from a gene expression microarray analysis can help put into context the biological meaningfulness of their expression patterns as well as help reduce the set of differentially expressed genes to be represented on a diagnostic panel based on their biology. The end result of this analysis will be to define a candidate expression classifier that will be validated in future, larger clinical trials.

QC Metrics for RNA, Amplified cDNA and Microarray Data.

Following informed consent, the suspicious pigmented lesion was tape stripped using EGIR and then biopsied as per standard of care. The resulting RNA isolated from the EGIR tape was amplified and profiled on the Affymetrix U133 plus 2.0 GeneChip. Microarray data were normalized by the GCRMA algorithm. To assure high quality of microarray data are generated, QC metrics were established for RNA, amplified cDNA and microarray data. The quality of RNA was assessed by capillary electrophoresis using the Experion system (Biorad, Hercule, Calif.) and RNA with at least one visible 18S rRNA was further processed for RNA amplification. The amplified cDNA was quantified by the Nanodrop system and quality of the amplified cDNA was also assessed by the Experion system. The yield of the amplified cDNAs greater than 5 mg and the average size distribution of the cDNAs greater than 750 nt were carried forward for microarray hybridization. Quality of the array data was further assessed using simpleaffy program in R and the array data with scaling factor less than 5.0 and % present call greater than 30% were used for further data analysis.

Class Modeling—PAM.

After passing the array data QC, 14 melanomas, 40 dysplastic nevi and 12 normal skin specimens were further analyzed. First, gene expression values less than 50 across all samples were filtered out and 16716 probesets were tested. These 16716 probesets were subjected to a statistical analysis for differentially expressed genes among melanomas, dysplastic nevi and normal skin using ANOVA (p<0.05), multiple testing correction algorithm (Westafall and Young permutation) and false discover rate (FDR) of 0.05. As indicated above, of the original 117 genes, an 89 gene panel (Table 2) was found to be a potential melanoma classifier. Further testing identified a 5-gene classifier (Table 3), a 30-gene classifier (Table 4) that includes newly identified genes, a 20-gene classifier (Table 5) that includes newly identified genes, and a 19-gene classifier that includes newly identified genes, which may all be used to discriminate melanomas from atypical nevi. The genes and respective classifier panels were analyzed using the Prediction Analysis of Microarrays (PAM) software freely available from Stanford University (Stanford, Calif.).

The PAM software uses a modification of the nearest centroid method, which computes a standardized centroid for each class in a training set. This refers to the average gene expression for each gene in each class divided by the within-class standard deviation for that gene. Nearest centroid classification takes the gene expression profile of a new sample, and compares it to each of these class centroids. The class, whose centroid it is closest to, in squared distance, is the predicted class for that new sample.

These genes were all subjected to a hierarchical clustering analysis and the melanoma specimens grouped together and were clearly distinguished from dysplastic nevi and normal skin. In addition, there are three distinct classes of dysplastic nevi; one is grouped together with normal skin and the second one was in between normal skin and melanomas, while the third one was grouped together with melanomas. These data suggest stratum corneum RNA, harvested by tape stripping with EGIR, can be used to distinguish melanoma from dysplastic nevi in suspiciously pigmented lesions.

Figure 5A:
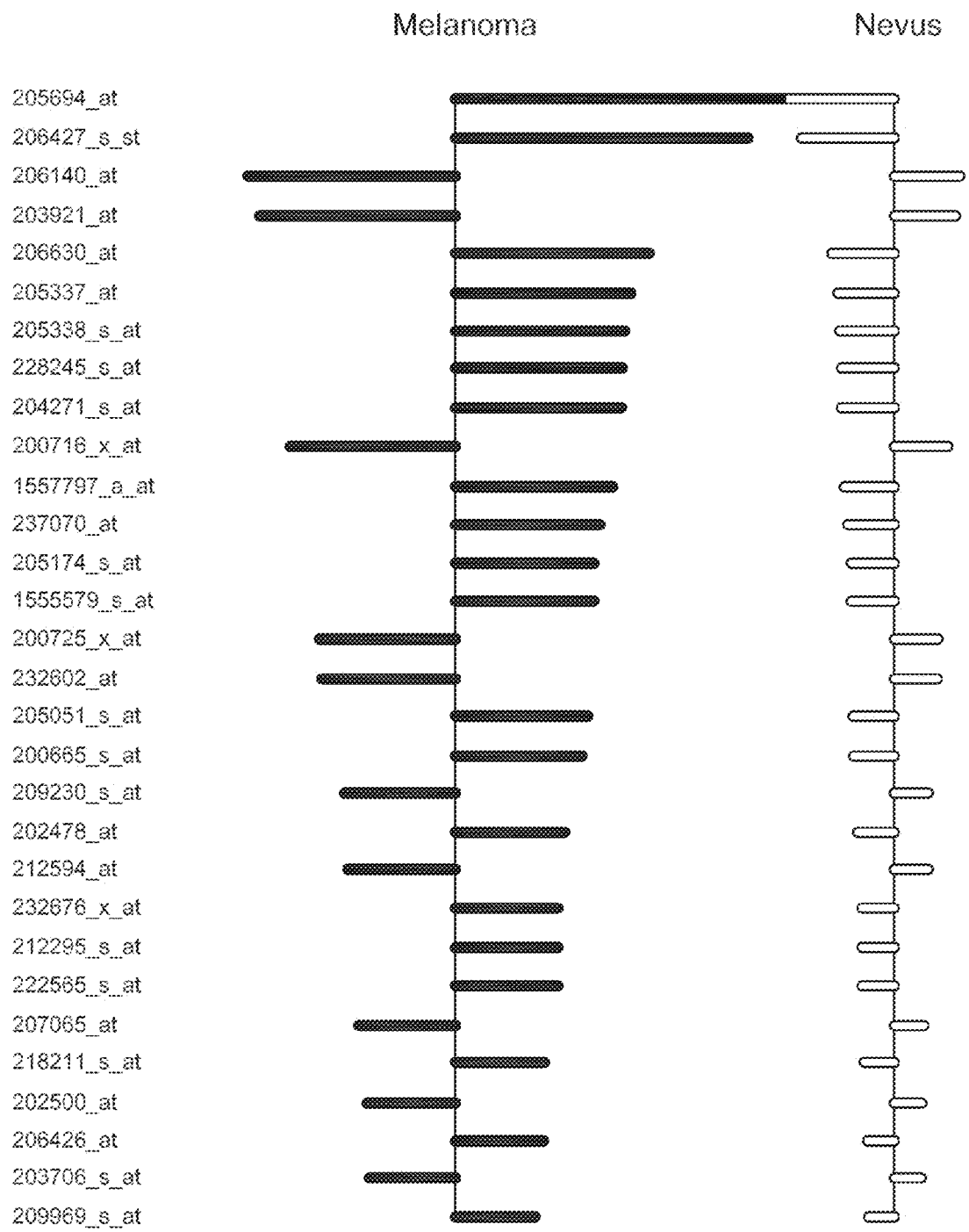
FIGS. 5A and 5B are graphical diagrams showing data from prediction analysis of the developed classifiers for distinguishing melanoma from atypical nevi and normal pigmented skin.
Figure 5B:
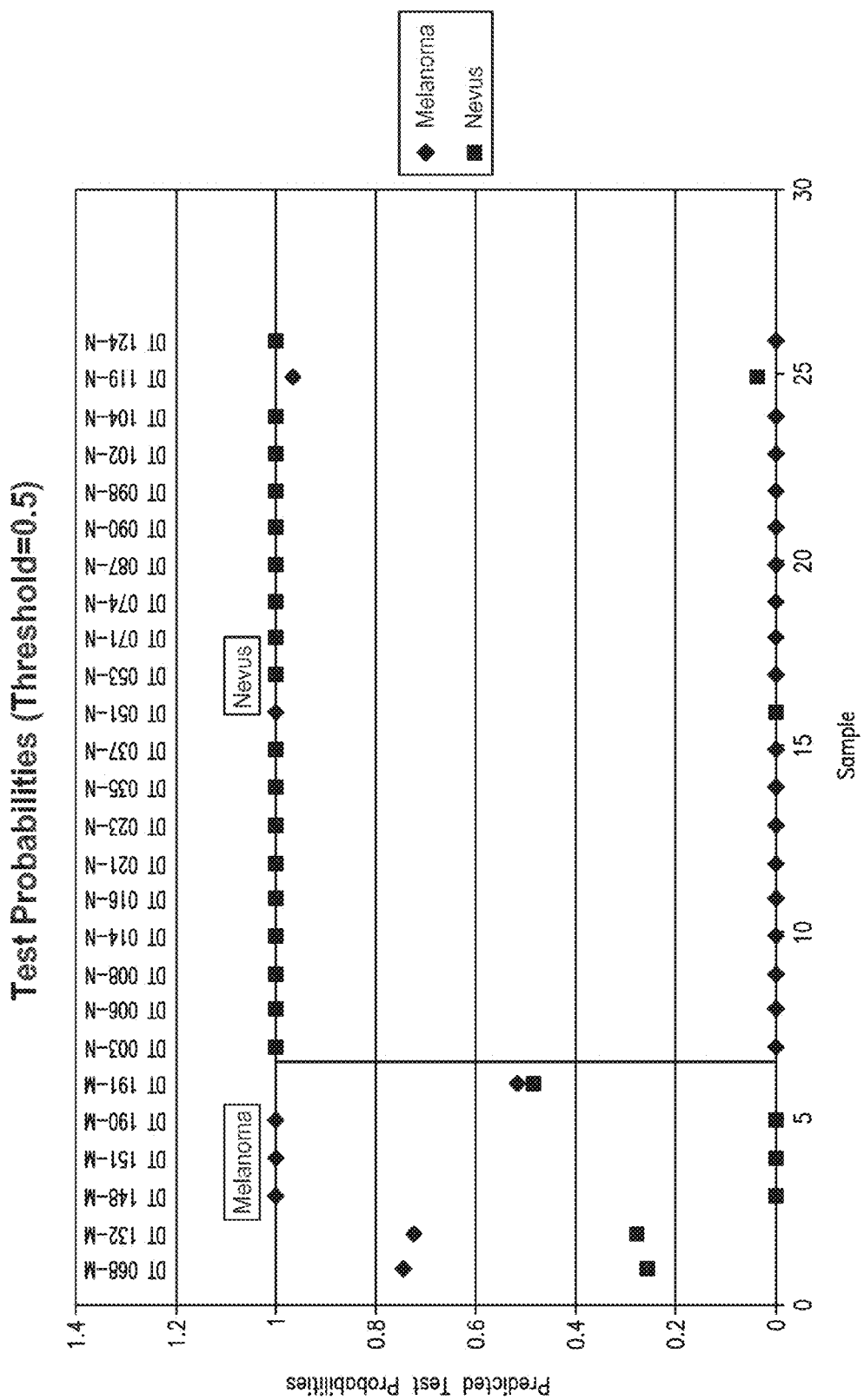
Figure 6A:
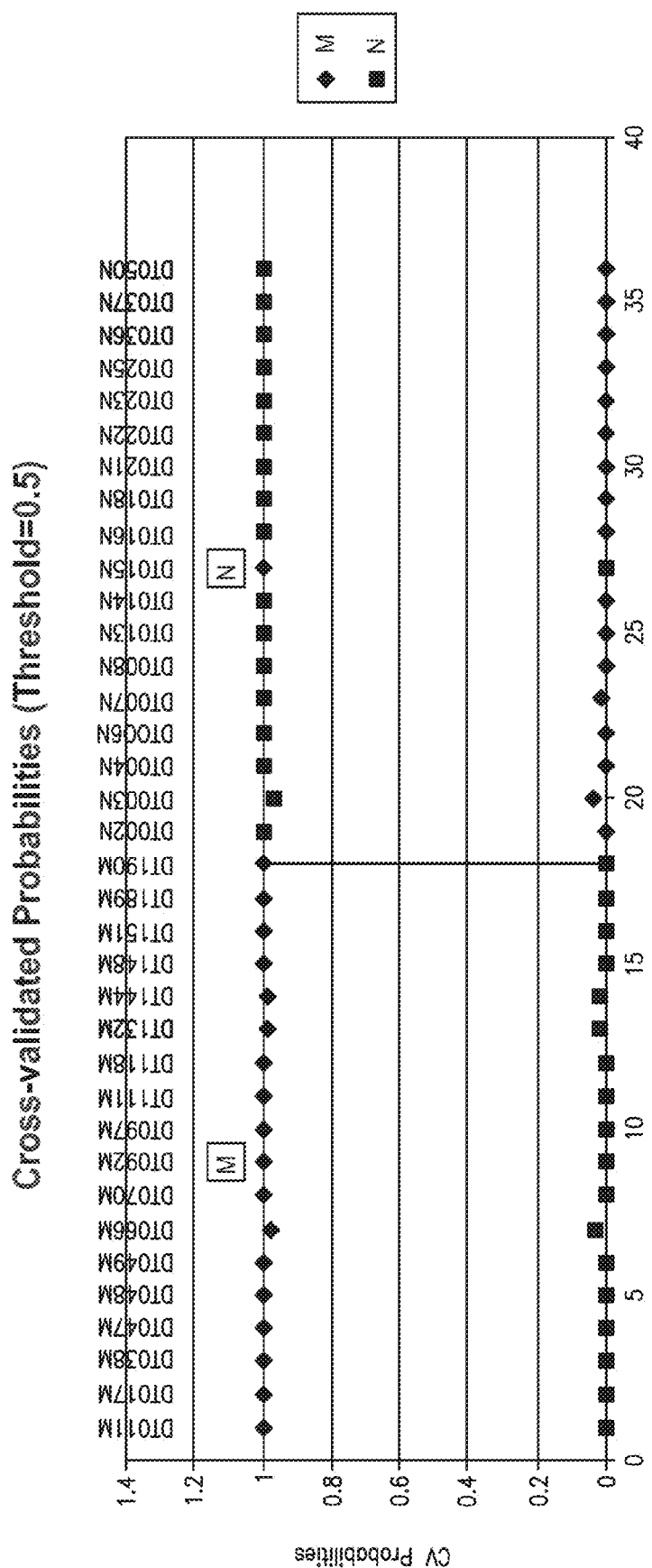
Figure 6B:
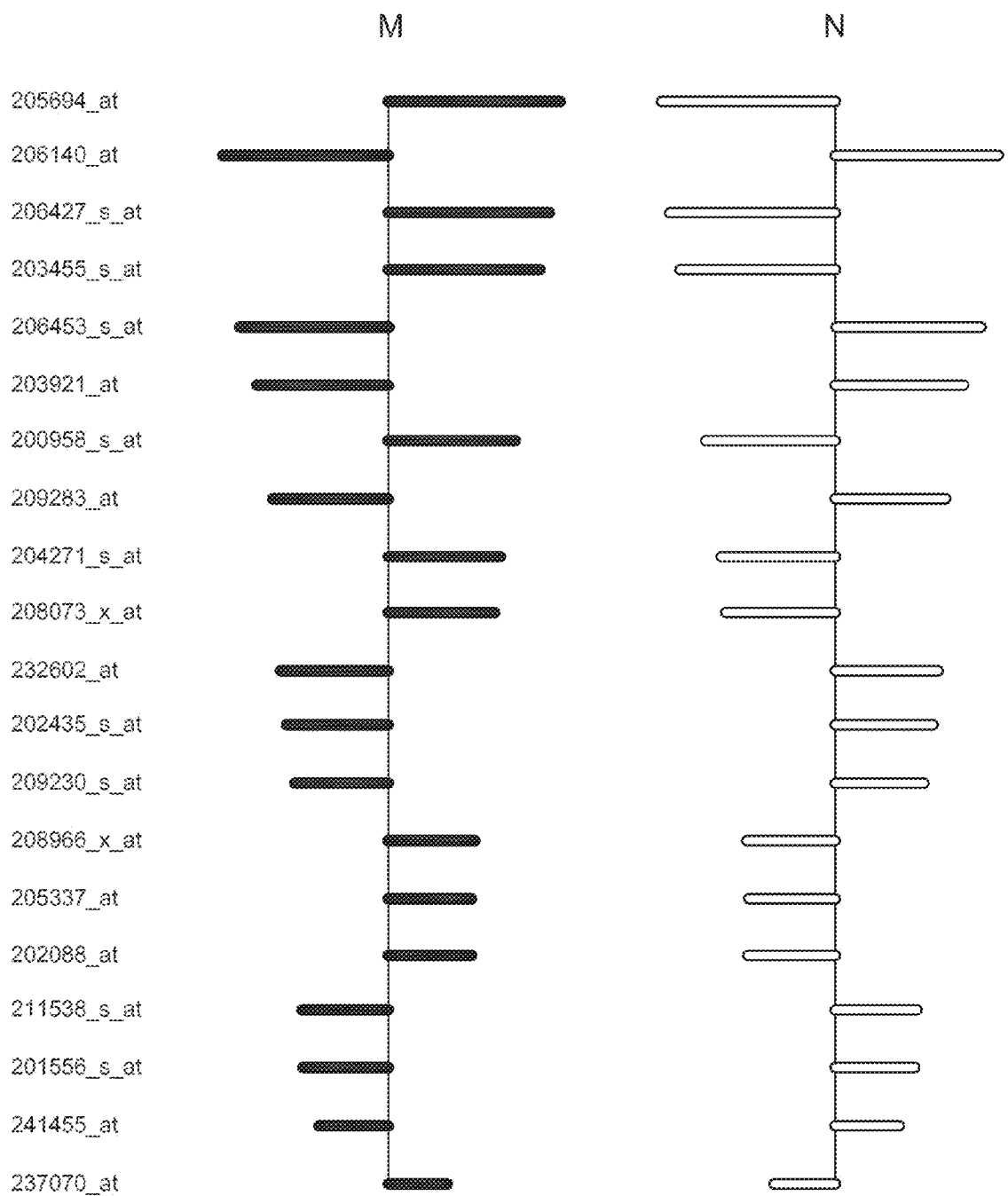
Figure 6C:
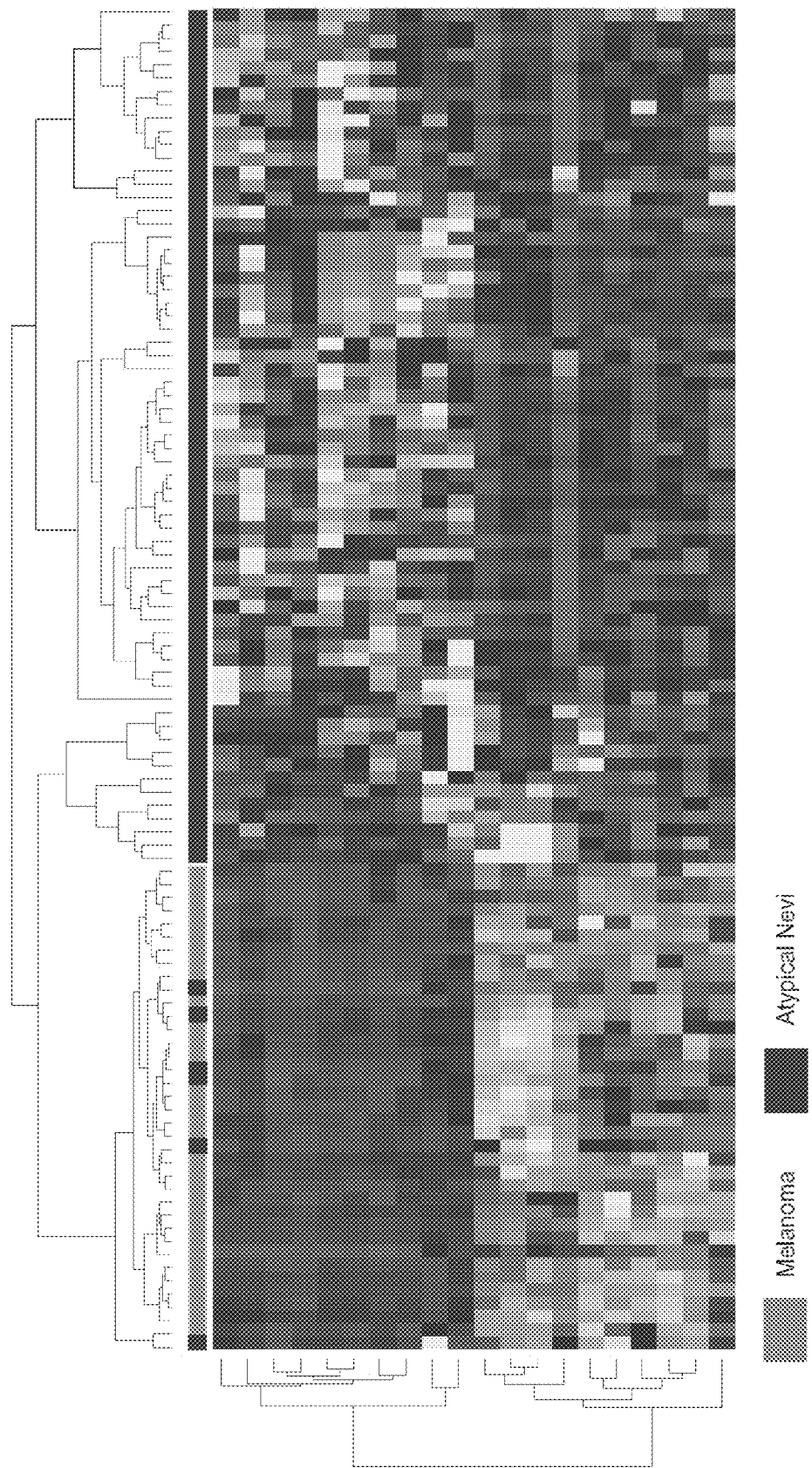

The analysis of the genes as potential melanoma classifiers to discriminate between melanomas and dysplastic nevi was performed using t-test (p<0.01), FDR (0.05) and 2-fold difference between melanomas and dysplastic nevi. Of the original 117 genes, an 89 gene panel (Table 2) was found to be a potential melanoma classifier and functions of these 89 genes were subjected to Ingenuity Pathway Analysis (IPA) (Ingenuity, Redwood City, Calif.). Among them, 15 genes are involved hair and skin development and function, 18 genes are involved in cellular development, 16 genes are involved in cellular growth and proliferation and 24 genes are related to cancer. Thus, differentially expressed genes are genes related to biological functions in melanocytes including melanin biosynthesis, melanocyte proliferation, differentiation and development. (See FIGS. 5 and 6).

Class Modeling—Random Forests.

Figure 7:
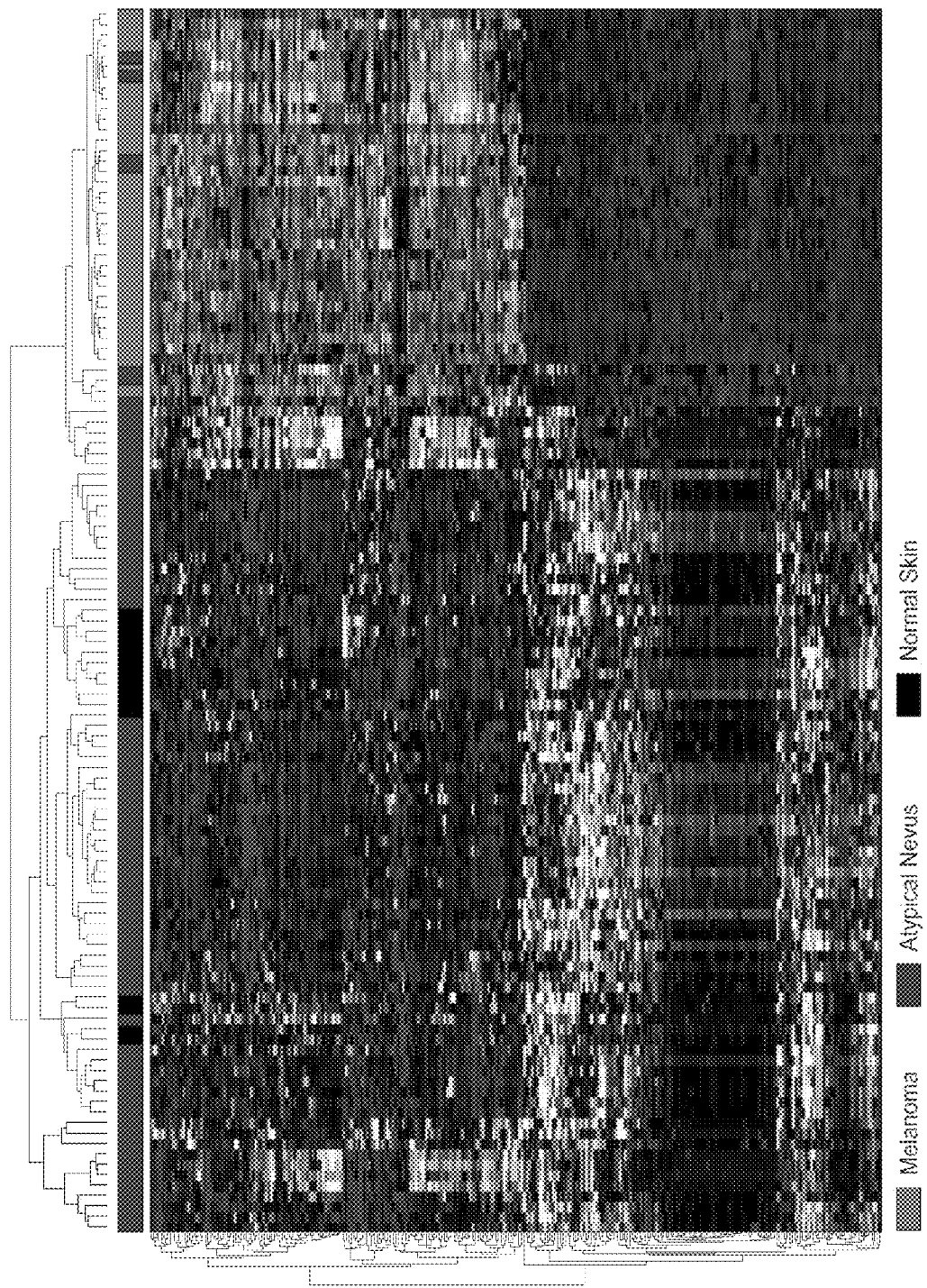
FIG. 7 is a hierarchial cluster analysis of the identified genes distinguishing melanoma from atypical nevi and normal pigmented skin.
Figure 8:
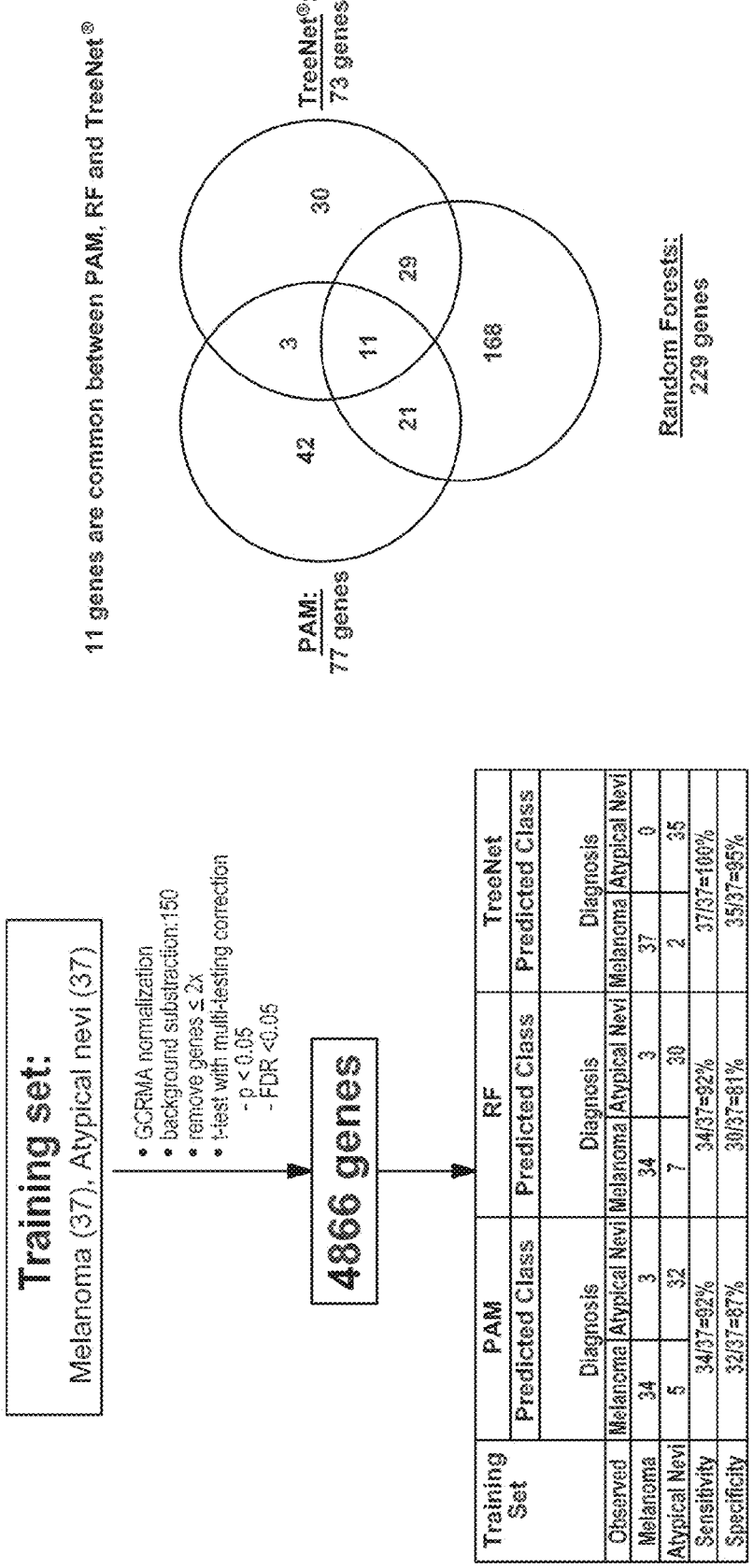
FIG. 8 is a graphical diagram showing results from classification modeling of the identified genes.
Figure 10:
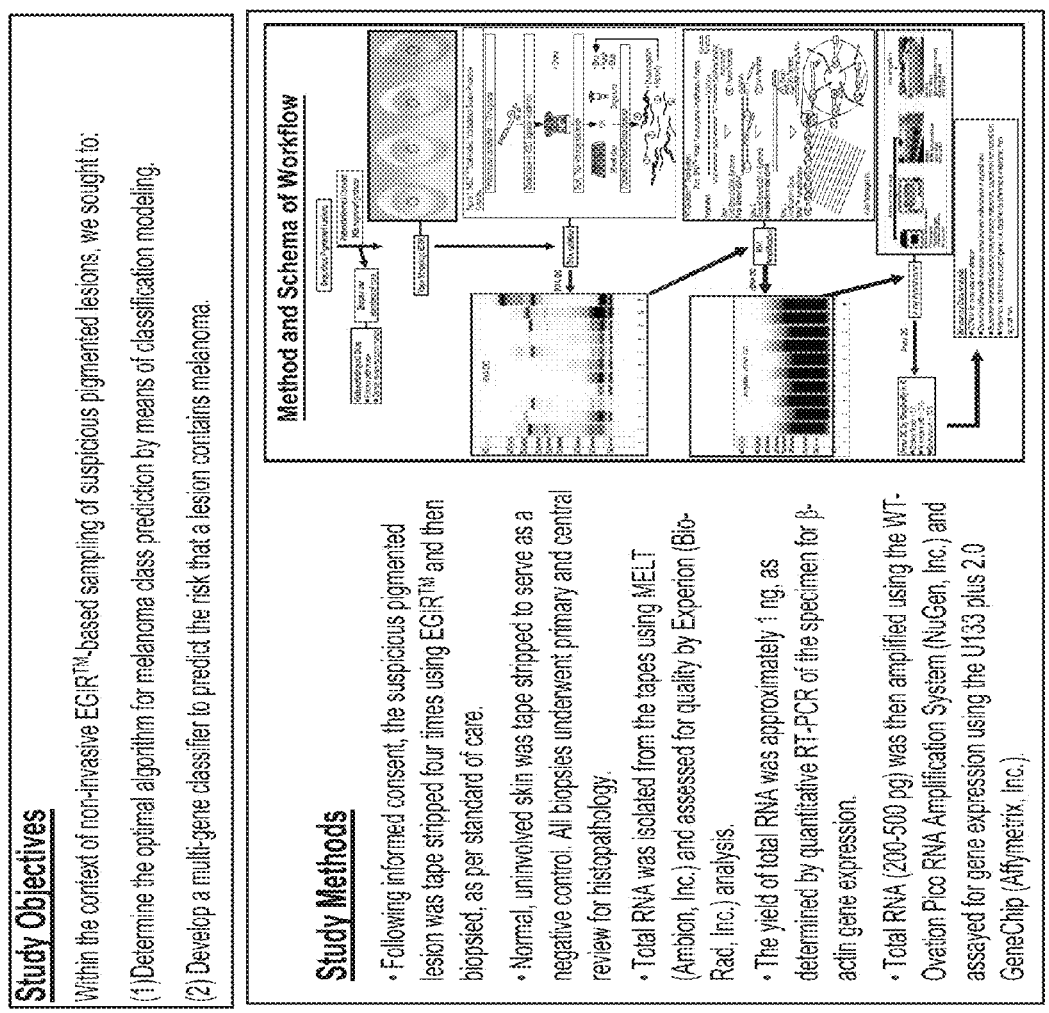
FIG. 10 is a pictorial diagram showing the development of a classifier to discriminate melanoma from atypical nevi using non-invasive tape strip-based genomic profiling.
Figure 10:
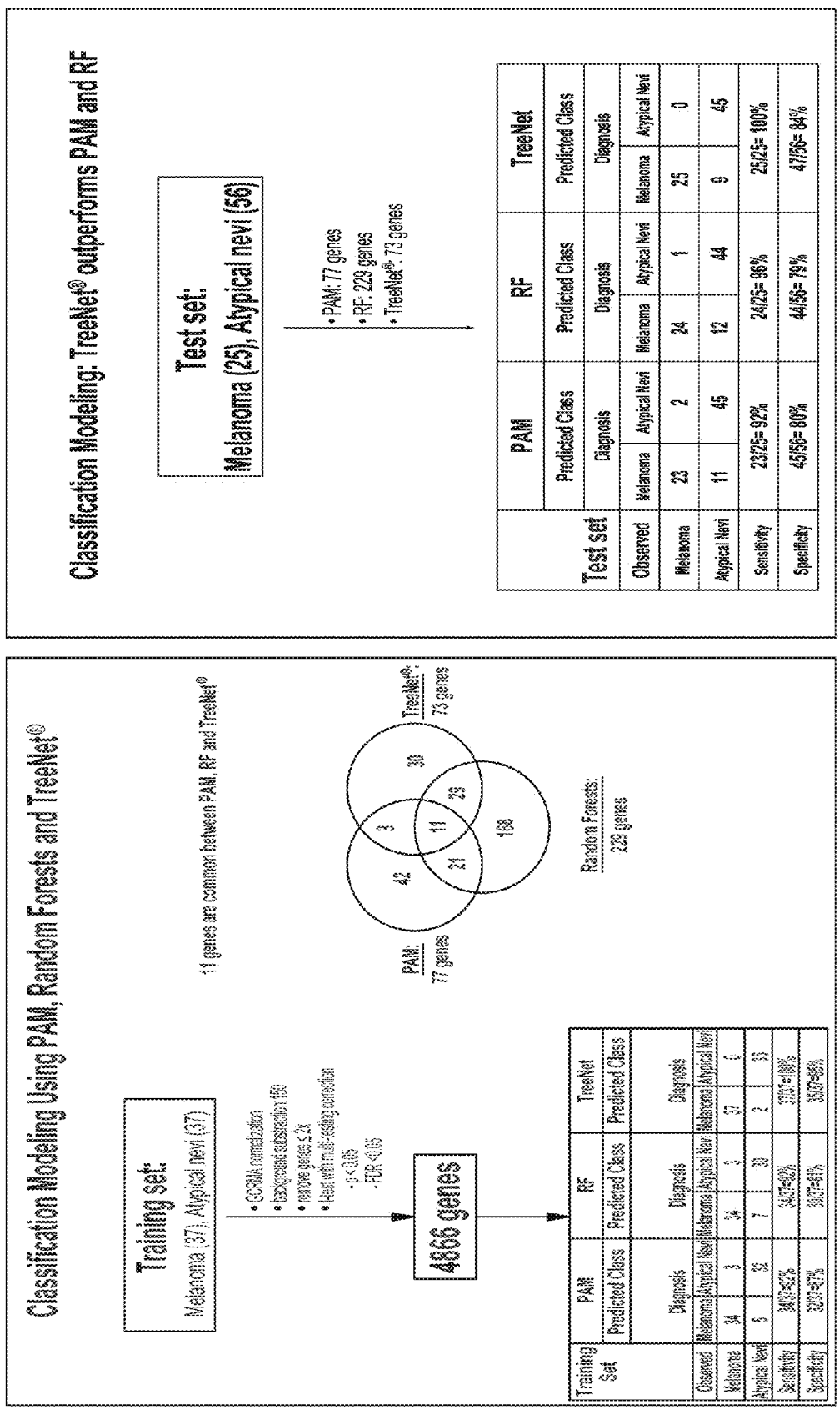

Additional work, in which 31 melanomas, 71 atypical nevi, and 15 normal skin controls were analyzed by GeneChip assay, identified 284 differentially expressed genes (p<0.001, false discovery rate q<0.05). Hierarchical cluster analysis of these genes showed that melanomas can be distinguished from atypical nevi and normal skin, and, suggested the existence of different classes of atypical nevi (FIG. 7). Several of the genes were found by Ingenuity Pathways analysis to play a role in melanocyte development and function, as well as, skin development, cellular proliferation, and cancer. These findings further demonstrated that the presence of melanoma, directly or indirectly, alters the gene expression profile of stratum corneum. 229 genes were subject to Random Forests analysis and 61 of those 229 genes were found to discriminate melanoma from atypical nevi (see FIG. 8).

Random Forests analysis is based on Bagging Predictors, which is a method for generating multiple versions of a predictor and using these to get an aggregated predictor. The aggregation averages over the versions when predicting a numerical outcome and does a plurality vote when predicting a class. The multiple versions are formed by making bootstrap replicates of the learning set and using these as new learning sets. Tests on real and simulated data sets using classification and regression trees and subset selection in linear regression show that bagging can give substantial gains in accuracy. If perturbing the learning set can cause significant changes in the predictor constructed, then bagging can improve accuracy.

Class Modeling—TREENET®.

Figure 12:
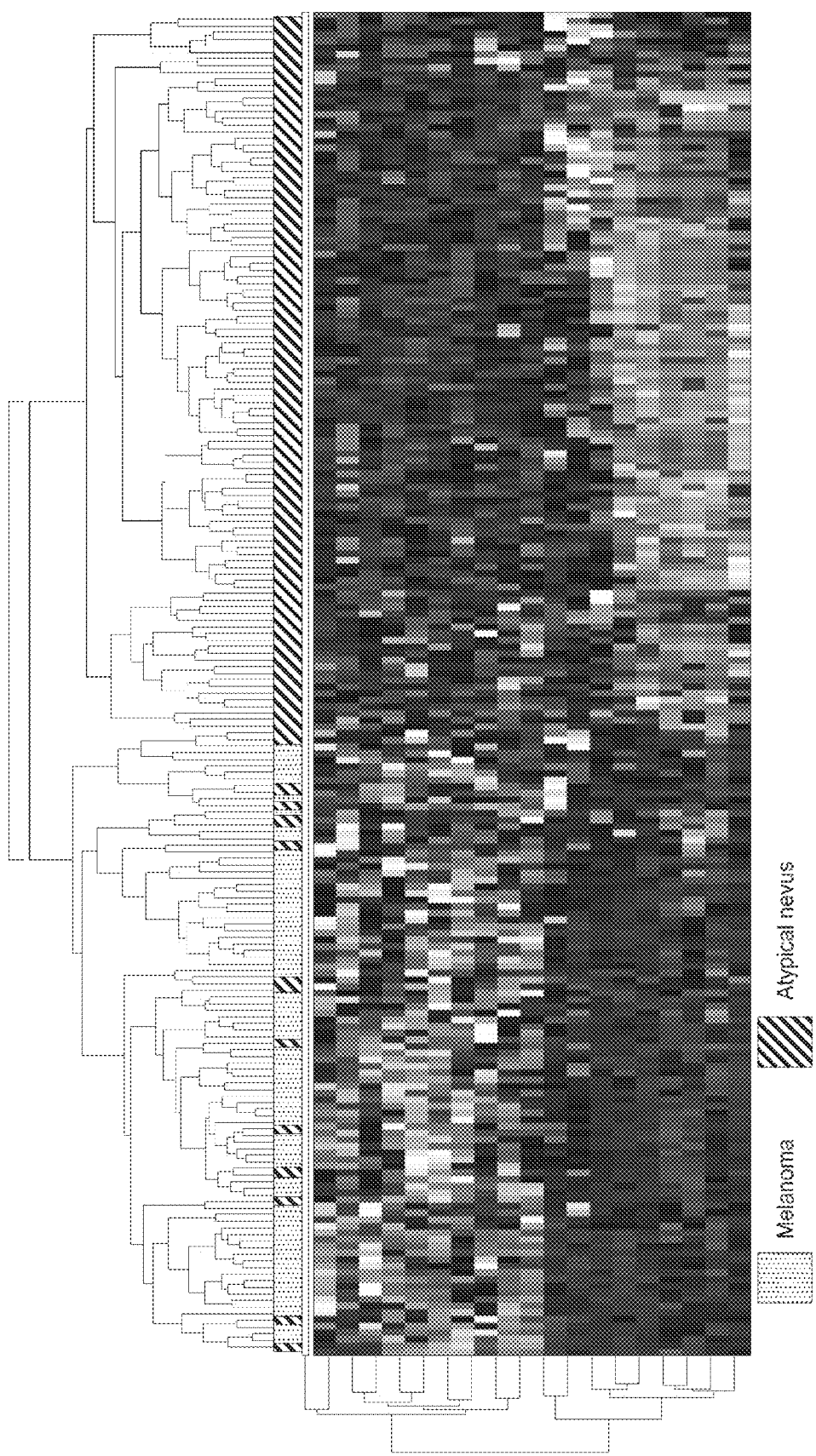
FIG. 12 is a pictorial diagram showing a hierarchial cluster analysis of the identified genes from the 19-gene classifier identified in FIG. 11.
Figure 13:
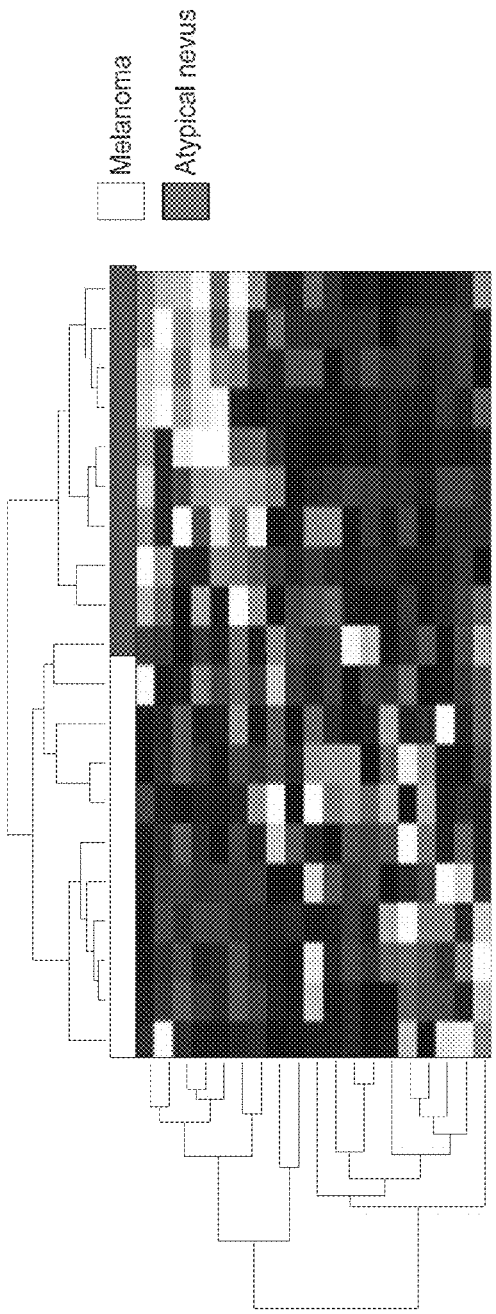
FIG. 13 is a pictorial diagram showing results from 10 melanoma and 10 nevi samples against the 19-gene classifier identified in FIG. 11.

82 additional genes were identified (Table 7). TREENET® software (Salford Systems, San Diego, Calif.) was used to identify a 20-gene panel (Table 8), which may all be used to discriminate melanomas from atypical nevi (see FIG. 9). An additional 19-gene classifier was identified from 7199 differentially expressed genes between melanoma and nevi (Table 6; see also FIGS. 11 and 12). The 19-gene classifier was tested against independent samples and shown to be 100% sensitive and 88% specific for detection of melanomas. In addition, results from 10 melanomas and 10 nevi indicated that qRT-PCR recapitulated the data obtained using the GeneChip microarray (FIG. 12 and see raw data in Tables 13 and 14).

TREENET® is a data mining tool that is based on boosted decision trees. TREENET® is a model building and function approximation system that also serves as an initial data exploration tool. It can extract relationships in data and calibrate how predictable the outcomes will be, and can handle both classification and regression problems.

Example 2

Preliminary Power and Sample Size Studies

Nevi vs. Primary Melanoma

The following sample size and power calculations are based exclusively on the large-scale cDNA study data provided in Haqq et al (2005). That data focused on normal skin (n=3 samples), nevi (n=9), primary melanomas (n=6) and metastatic melanomas (n=19). For purposes of the sample size calculations, the focus was on the comparison of nevi to primary melanomas. Power and sample size assessments were calculated based on the bootstrap strategy outlined by Page et al. Using the raw data available from the Haqq et al (2005) study, gene expression differences—based on all 14,772 probes used in their cDNA assay—between nevi and primary melanomas were computed using simple t-tests for each probe/gene. Note that multiple probes can be used interrogate individual genes. In addition, normal skin, nevi, and primary melanoma gene expression differences were also assessed in a three group analysis of variance (ANOVA), with the specific contrast between nevi and primary melanoma computed from this ANOVA. In the figures that follow, three main parameters are used to assess power and sample size. Table 9 (adapted from Page, et al.) shows the number of genes truly or not truly differentially expressed, and provides a simple way of describing these parameters, which are defined as follows (with the color of the curves corresponding to each parameter provided in parentheses for FIGS. 1A and 2A, although FIGS. 1B and 2B focus exclusively on the EDR as defined below.

EDR:

Expected Discovery Rate (from Table 9, D/(B+D)). This reflects the expected proportion of probes/genes that will be declared significantly differentially expressed at the defined threshold (here taken to be, for the most part, p<0.05) that are, in fact, differentially expressed between nevi and primary melanomas.

PTP:

Expected Proportion of probes/genes that are True Positives (Table 9, D/(C+D)). This proportion reflects the number of probes/genes showing expression differences that are likely to be truly differential expressed out of the total number of genes whose expression values result in test statistics less than the threshold (e.g., 0.05).

PTN:

Probability of a True Negative result (Table 9, A/(A+B)). This probability concerns probes/genes that are not significantly different at the assumed threshold (e.g., 0.05) that are, in fact, not differentially expressed between skin and melanoma.

TABLE 9

Parameters of Relevance for Assessing the Power of Microarray Studies

| Result based on array analysis | Not differentially expressed | Truly differentially expressed |
|---|---|---|
| Genes not significant | A | B |
| Genes significant | C | D |

These columns represent the number of genes found to satisfy the given constraint;
A = genes found not to be differentially expressed in an array experiment and that are truly not differentially expressed;
B = genes that are differentially expressed but are not found to be differentially expressed in the array experiment (false negative);
C = genes that are found to be differentially expressed in the array experiment but are not truly differentially expressed (false positives);
D = gene found to be differentially expressed in an array experiment and that are truly differentially expressed.

Nevi Versus Primary Data.

Figure 1B:
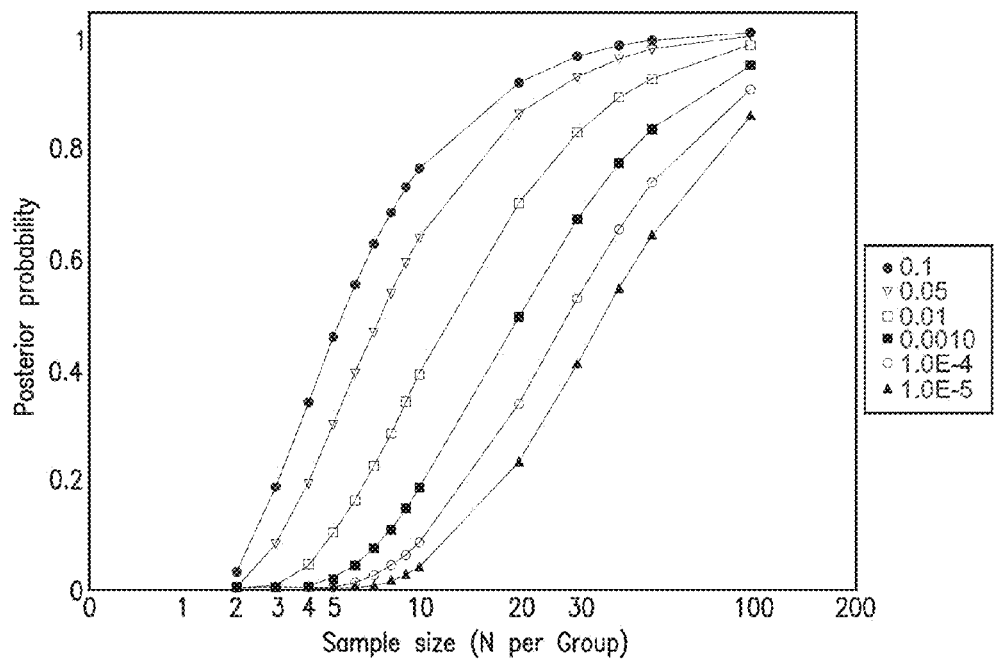

The sample size analysis considered the number of samples necessary to "discover" or identify a probe or gene or set of probes/genes that could differentiate nevi from primary melanomas based on the probe/gene expression differences obtained by Haqq et al. (2005). FIG. 1a provides a plot of the EDR, PTP, and PTN as a function of sample size, assuming a threshold for declaring the significance of a probe/gene expression difference between nevi and primary melanoma of $p<0.05$. Thus, from the plot, it appears that in order to "discover," or identify, 80% of all genes that have been interrogated on a chip that exhibit a probe/gene expression difference producing a test statistic p-value $<0.05$ that will actually reflect a true probe/gene expression difference, a sample size of roughly 20 per nevi and primary melanoma group will be needed. Note that if all 14,772 probes are considered, one is likely to have $14,772 \times 0.05 = 738$ exhibit p-values $<0.05$ by chance alone, of which $1,727 \times 0.80 = 1,381$ will likely reflect true gene expression differences at that significance (i.e., p-value) level. If one is interested in identifying a smaller set of genes that have a greater probability of being detected as truly differentially expressed, a more stringent threshold for statistical significance (e.g., 0.001) can be used. This would generate $14,772 \times 0.001 = 15$ genes with p-values $<0.001$ by chance of which ~45% (i.e., $34 \times 0.45 = 7$ would likely be truly differentially expressed at that level; see FIG. 1b; note curves in FIG. 1b only correspond to the EDR with different assumed type I error rates).

Figure 2A:
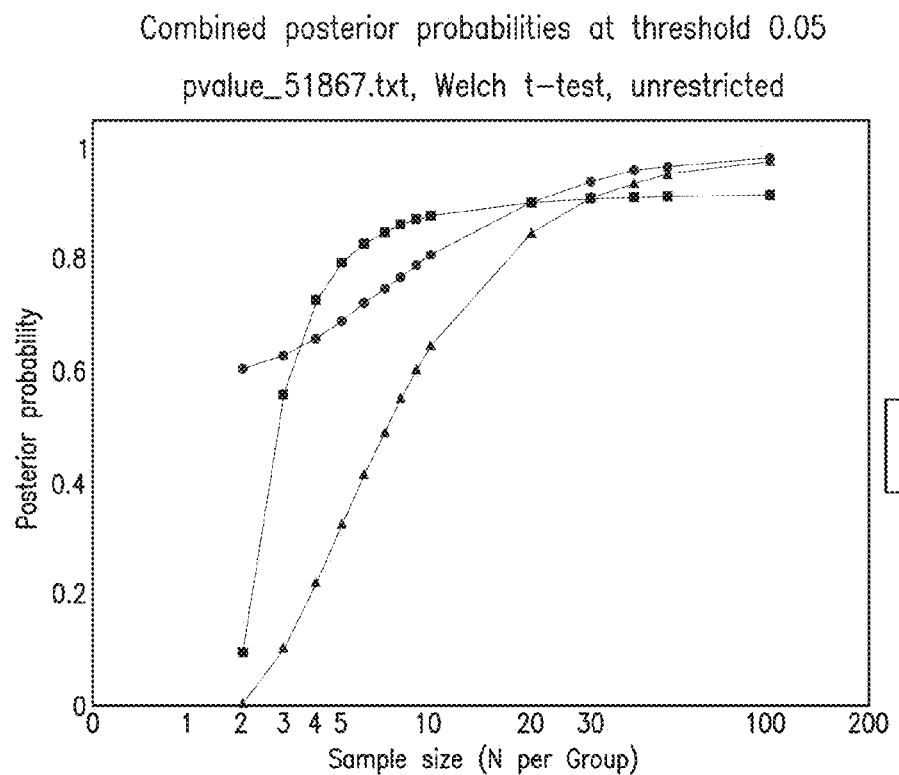
FIGS. 2A and 2B are graphical diagrams showing data from a sample size analysis that considered the contrast results for nevi vs. primary melanoma in the context of an analysis of variance (ANOVA) comparing normal skin, nevi, and primary melanoma
Figure 2B:
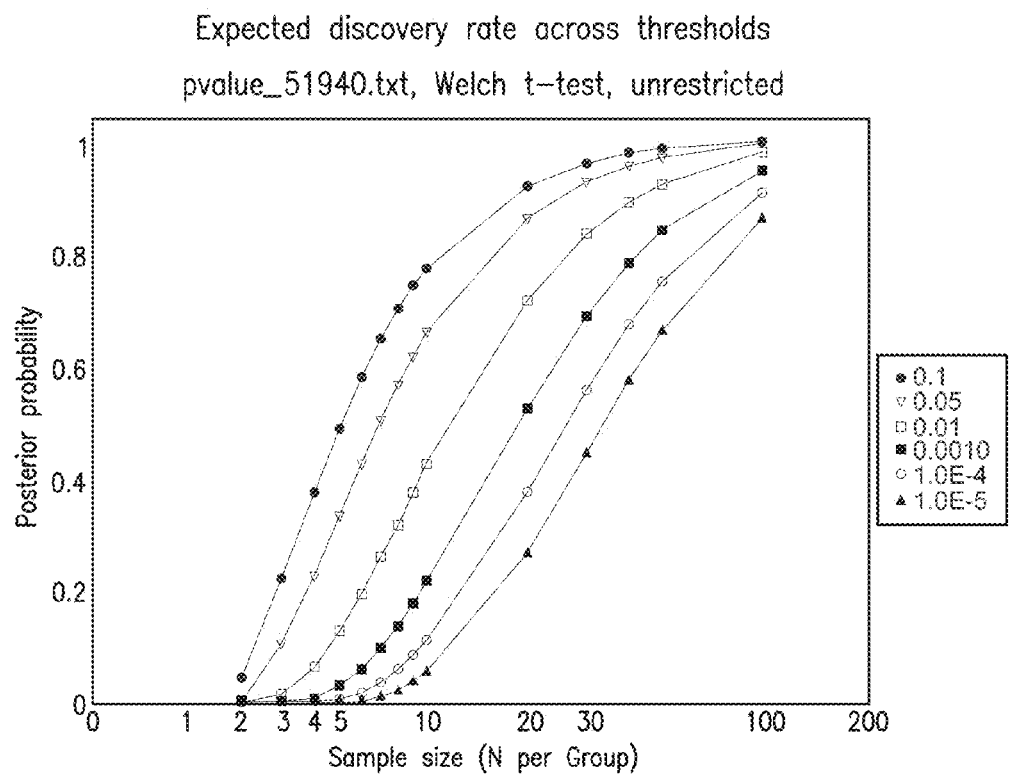

A sample size analysis that considered the contrast results for nevi vs. primary melanoma in the context of an analysis of variance (ANOVA) comparing normal skin, nevi, and primary melanoma was also pursued. The rationale for this is that there are more differences between normal skin and either nevi or primary melanoma than there are between nevi and primary melanoma (based on an analysis of the Haqq et al (2005) data), and an analysis that considers normal skin gene expression variation may help reduce the noise in the assessment of nevi vs. primary melanoma gene expression differences. FIGS. 2a and 2b display the results of these analyses and provide similar sample size guidelines to those reflected in FIGS. 1a and 1b.

Figure 3A:
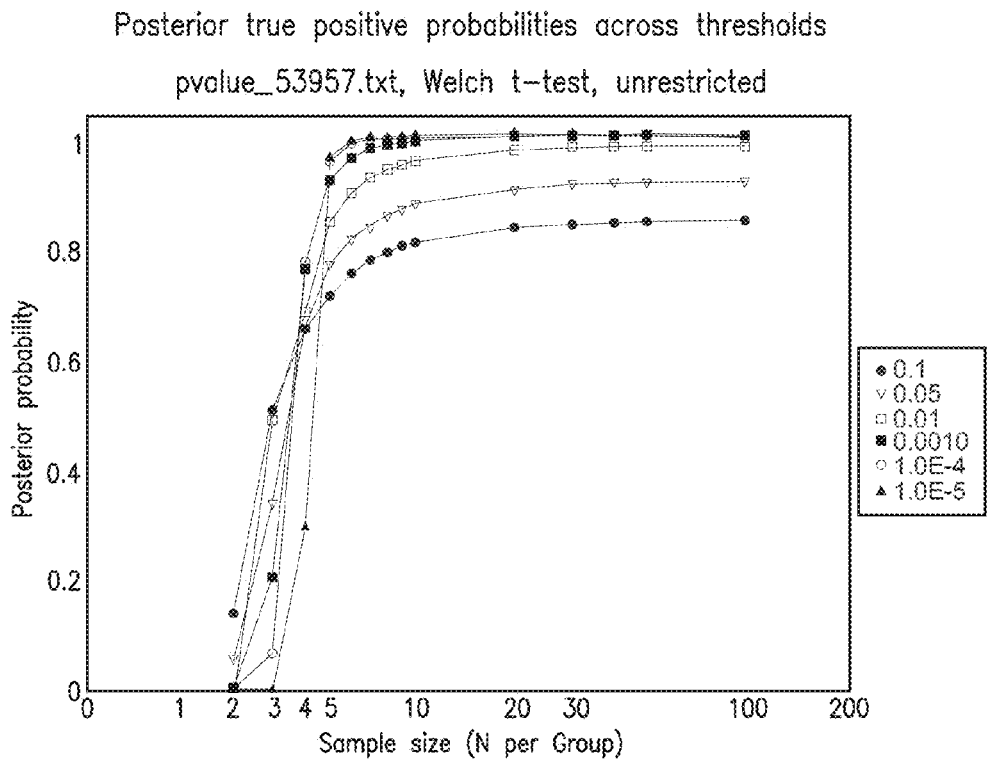
FIGS. 3A and 3B are graphical diagrams showing data from an analysis focusing exclusively on the posterior true probability (PTP) for different assumed significance levels.
Figure 3B:
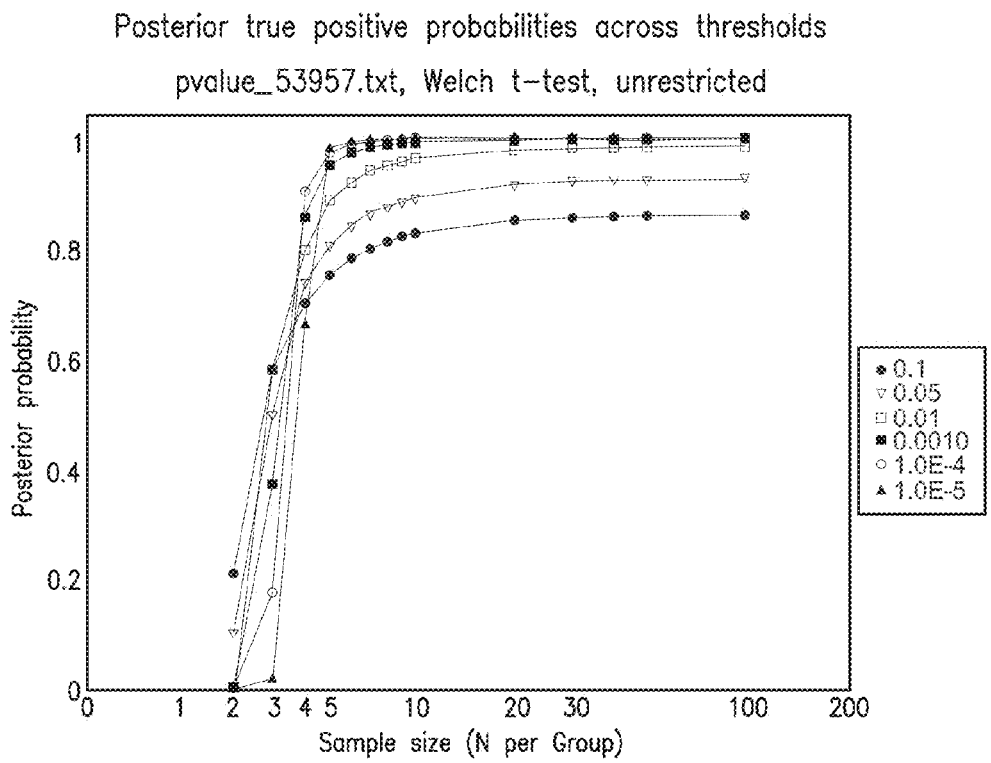

An analysis focusing exclusively on the posterior true probability (PTP) was also considered since, as discussed, there may be many probes/genes that exhibit differences between nevi and primary melanomas at a certain probability level purely by chance (given the large number of probes/genes interrogated). Thus, the likely fraction of these probes/genes that are truly differentially expressed is important to assess. FIGS. 3a and 3b reflect the results for different assumed significance levels.

Thus, an argument can be made that a study with approximately 20 samples per nevi and primary melanoma groups would have sufficient power to detect 80% of all genes that are likely to exhibit differential expression at a p-value level of 0.05 because they are, in fact, differentially expressed at this level. However, the number of genes (or probes) contributing to this set of differentially expressed genes is likely to number in the hundreds, if 10,000-30,000 probes are used or 5,000-10,000 genes are studied. If interest is in identifying a smaller number of probes or genes (~25-40) that have a greater probability of being differentially expressed, say, at a p-value of 0.001, then ~30 nevi and 30 primary melanoma samples would be needed (see FIGS. 1, 2, and 3).

Example 3

Tape Stripping to Recover Nucleic Acids from Normal Skin

The following procedure was used to recover nucleic acids from normal skin (e.g., the mastoid or upper back areas) of a subject.

Tapes were handled with gloved hands at all times. Locate a particular site that is relatively blemish-free and healthy, unless otherwise specified by the protocol. Preferred normal skin sites are the mastoid process (the bony process behind the ear at the base of the skull) and the upper back, immediately superior to the scapular spine. Shave the site if necessary to remove non-vellus hairs. Cleanse the site with an alcohol wipe (70% isopropyl alcohol). Let the site air dry completely before application of the tape. It is recommended to wait approximately 2 minutes to ensure the site is completely dry before application of the tape.

Apply the tape to the skin site. If more than one tape is used, apply tapes in sequential order starting from the left side. Use a surgical skin marker and/or a water soluble marker to mark the location of the tape on the skin in order to align subsequent tapes.

Start the tape harvesting procedure by applying pressure (press on the tape firmly). Ensure that the skin is held taut to ensure that the tape does not move while applying pressure. Then remove the tape slowly in one direction. Place the edge of the tape onto the strip at the top of the packet with the adhesive surface of the tape facing down to protect the sample. Put a second tape on the same site; apply pressure firmly as above. Remove the tape slowly in an opposite direction to that used in the immediately previous application.

Continue tape stripping by putting additional tapes on the same site, following the steps provided above. The site may stripped with a total of at least four tapes, unless otherwise specified in the protocol. Place the strip into a storage bag and immediately place the samples on dry ice or into storage at $-20°$ C. or below until analysis.

Example 4

Tape Stripping to Recover Nucleic Acids from Pigmented Lesions

The following procedure was used to recover nucleic acids from pigmented lesions and/or skin suspected of melanoma of a subject. In contrast to normal skin, lesional skin should have a preoperative biopsy diameter of greater than or equal to about 6 mm, but less than that of the tape disc. Multiple lesions must be at least about 4 mm apart. The area of tape that touches the lesion should be generously demarcated on the tape with an insoluble ink pen so that this area may be cut away from the surrounding tape at the laboratory as part of the RNA extraction procedure.

As above, tapes were handled with gloved hands at all times. Shave the site if necessary to remove non-vellus hairs. Cleanse the site with an alcohol wipe (70% isopropyl alcohol). Let the site air dry completely before application of the tape. It is recommended to approximately 2 minutes to ensure the site is completely dry before application of the tape.

Apply the tape to the skin site. If more than one tape is used, apply tapes in sequential order starting from the left side. Use a surgical skin marker and/or a water soluble marker to mark the location of the tape on the skin in order to align subsequent tapes. Apply the tape to the suspect lesion, which should have a diameter that is greater than or equal to about 6 mm.

Start the tape harvesting procedure by applying pressure directly over the lesion and avoiding surrounding normal skin (press on the tape firmly). Ensure that the skin is held taut to ensure that the tape does not move while applying pressure. Using a marking pen, demarcate a zone around the lesion such that the area of the lesion is encompassed within the inked boundary and the boundary is approximately 1 mm from the lesion border.

Remove the tape slowly in one direction. Place the edge of the tape onto the adhesive strip with cells facing down to protect the sample. Put a second tape on the same site following directions provided above. Repeat until the lesion has been stripped a total of at least four times, unless otherwise specified in the protocol. Place the strip into a storage bag and immediately place the samples on dry ice or into storage at −20° C. or below until analysis.

Example 5

Gene Expression Profile to Distinguish Melanoma from Atypical Nevi

Figure 4A:
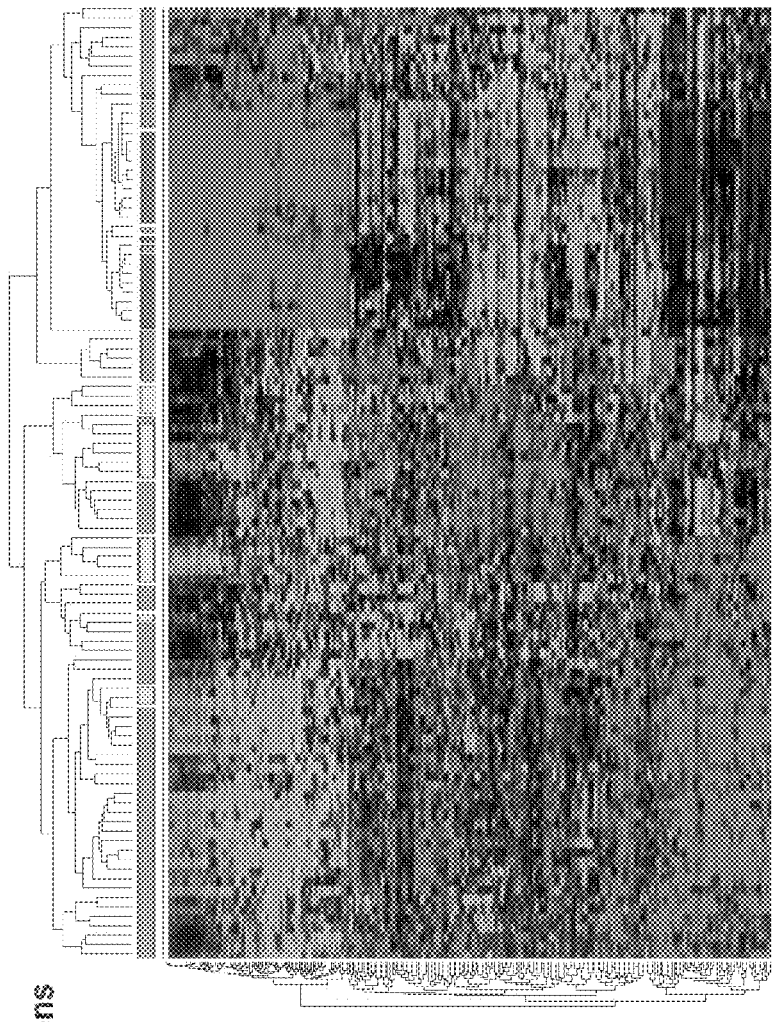

The purpose of this study is to determine whether stratum corneum RNA, harvested by tape stripping with EGIR can be used to distinguish melanoma from atypical nevi in suspicious pigmented lesions. See FIG. 4A.

Suspicious pigmented lesions were tape stripped four times using EGIR and then biopsied as per standard of care. Normal, uninvolved skin was tape stripped to serve as a negative control. All biopsies underwent primary and central review for histopathology. Total RNA was isolated from the tapes using MELT (Ambion, Inc.) and assessed for quality by Experion (Bio-Rad, Inc.) analysis. The yield of RNA was approximately 1 ng, as determined by quantitative RT-PCR of the specimen for β-actin gene expression. Total RNA (200-500 pg) was then amplified using the WT-Ovation Pico RNA Amplification System (NuGen, Inc.) and assayed for gene expression profile using the U133 plus 2.0 GeneChip (Affymetrix, Inc.).

Figure 4B:
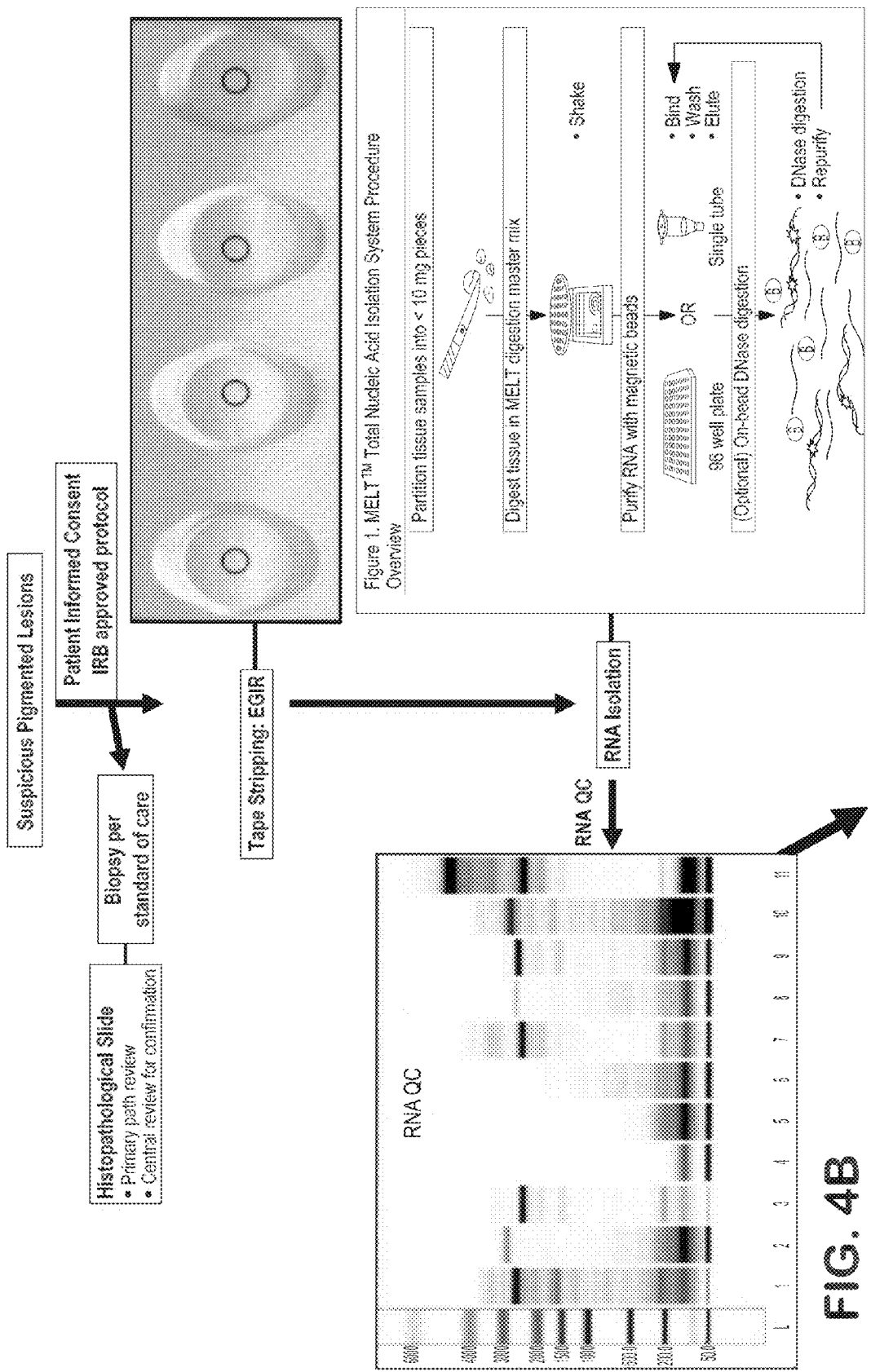
Figure 4B:
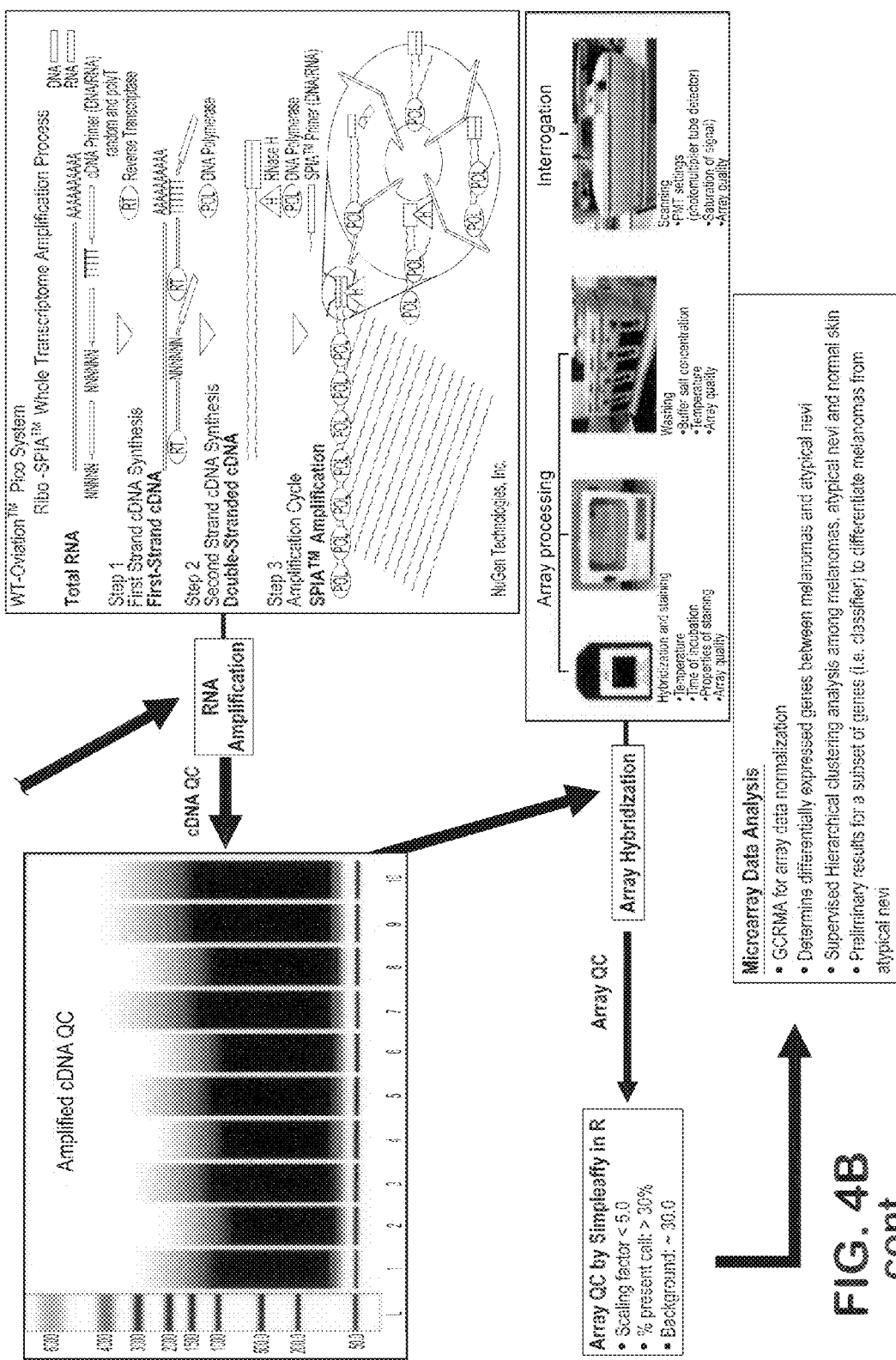
Figure 4C:
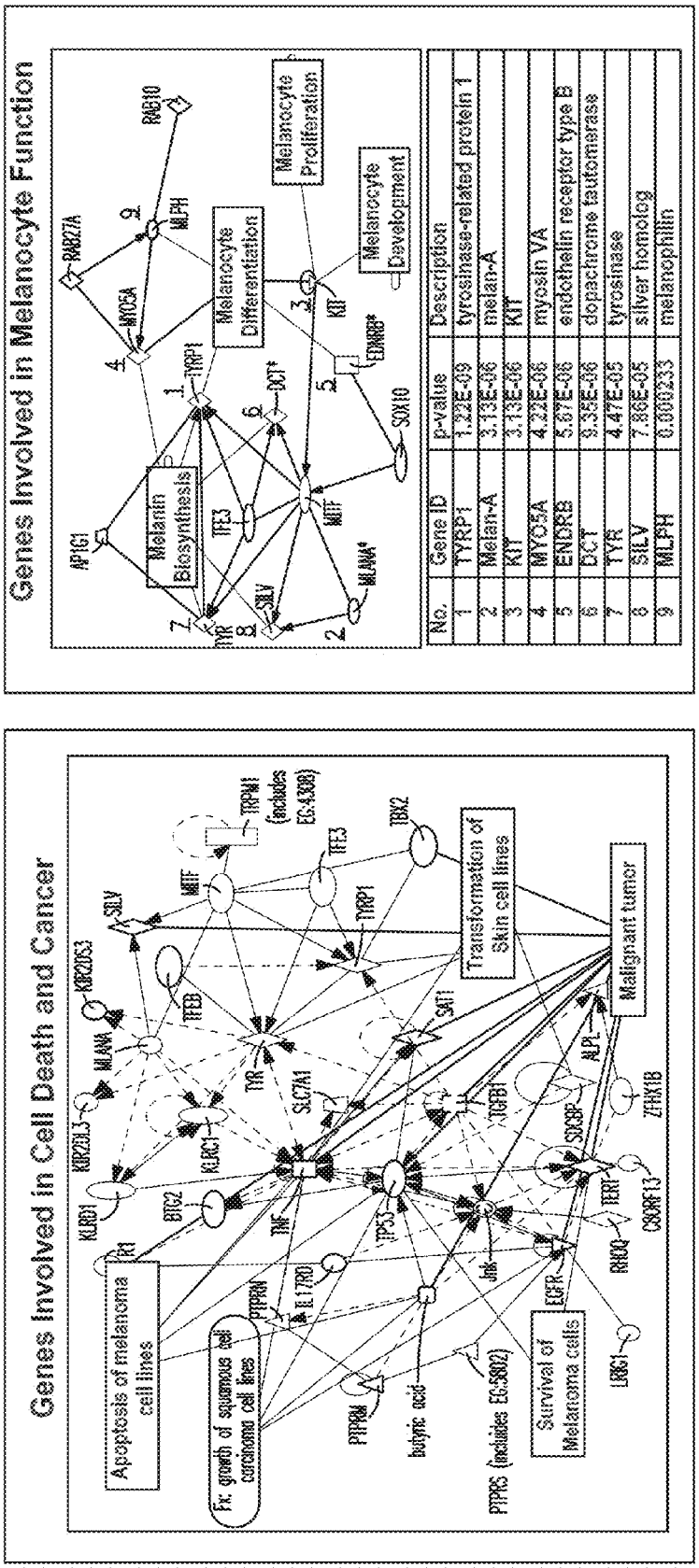

The resulting RNA isolated from the EGIR tape is then amplified and profiled on the Affymetrix U133 plus 2.0 GeneChip. Microarray data is normalized by the GCRMA algorithm. Further analyses by means of ANOVA analysis ($p<0.05$) with a false discovery rate of 0.05 and multiple correction testing using Westfall and Young permutation identified approximately 117 genes as differentially expressed between melanoma, dysplastic nevi and normal skin (Table 1). Hierarchical clustering of these genes showed that the melanoma specimens grouped together and were clearly distinguished from dysplastic nevi and normal skin (FIG. 4B). In addition, 89 of the 117 genes shown in Table 1 were further identified (Table 2) as potential discriminators between melanoma and dysplastic nevi ($p<0.01$, false discovery rate $q<0.05$). When these 89 genes were subjected to Ingenuity Pathways analysis many were found to play roles in melanoma, hair and skin development and function, cellular development, cellular growth and proliferation and cancer. These findings demonstrate that EGIR-harvested RNA from suspicious pigmented skin lesions can be used to differentiate melanoma from dysplastic nevi (FIG. 4C). Further, these results suggest that the gene expression profile of stratum corneum is altered, either directly or indirectly, by the presence of melanoma (FIG. 4D).

In subsequent studies that compared normal and inflamed skin, sequential application of four small tapes at the same skin site recovered enough intact RNA to perform quantitative reverse-transcription polymerase chain reaction (qPCR) assay and DNA microarray analysis for investigation of gene expression. The latter assay was performed using the Affymetrix HG-U133A GeneChip following two rounds of amplification of 10 ng of total RNA sample that produced 30-80 μg of anti-sense RNA. Comparison of results from two subjects, each sampled at three separate sites, showed 12% intra- and inter-subject variance in gene measurements, a result that is well within the Affymetrix specified coefficient of variation (CV) for GeneChip assay. Of note is that differential expression of Y-chromosome genes was observed, a result that accurately distinguished the different genders of the 2 subjects. GeneChip assay was then performed on RNA isolated from tape stripping each of 3 subjects from normal, water occluded, and sodium lauryl sulfate-irritated study groups. The majority of 100 genes, whose expression is most significantly altered between untreated and SLS-treated skin showed, were already known to be involved in tissue inflammation and injury functions. Thus, RNA harvested by EGIR technology is more than adequate for microarray-based gene expression profiling and appropriately reflects the pathologic state of skin.

Recent work by Benson et al (2006) demonstrates that RNA can be recovered from psoriatic lesions and that the general RNA expression profile of tape strip recovered RNA is consistent with biopsy RNA derived from lesions on the same patient. Further work (see U.S. Pat. No. 7,183,057, incorporated herein by reference) has shown that psoriatic lesions can be sampled with tape during treatment with Enbrel and that strong correlations could be made between gene expression in week one of treatment and clinical response at weeks 4 and 8. This work further establishes the credentials of tape stripping for the recovery of physiologically relevant RNA from the surface of the skin.

Example 6

Gene Expression Profile to Distinguish Solar Lintigenes from Melanoma, Atypical Nevi, and/or Normal Skin The purpose of this study is to determine whether stratum corneum RNA, can be used to distinguish solar lentigines from melanoma, atypical nevi, and/or normal skin in suspicious pigmented lesions.

Figure 15:
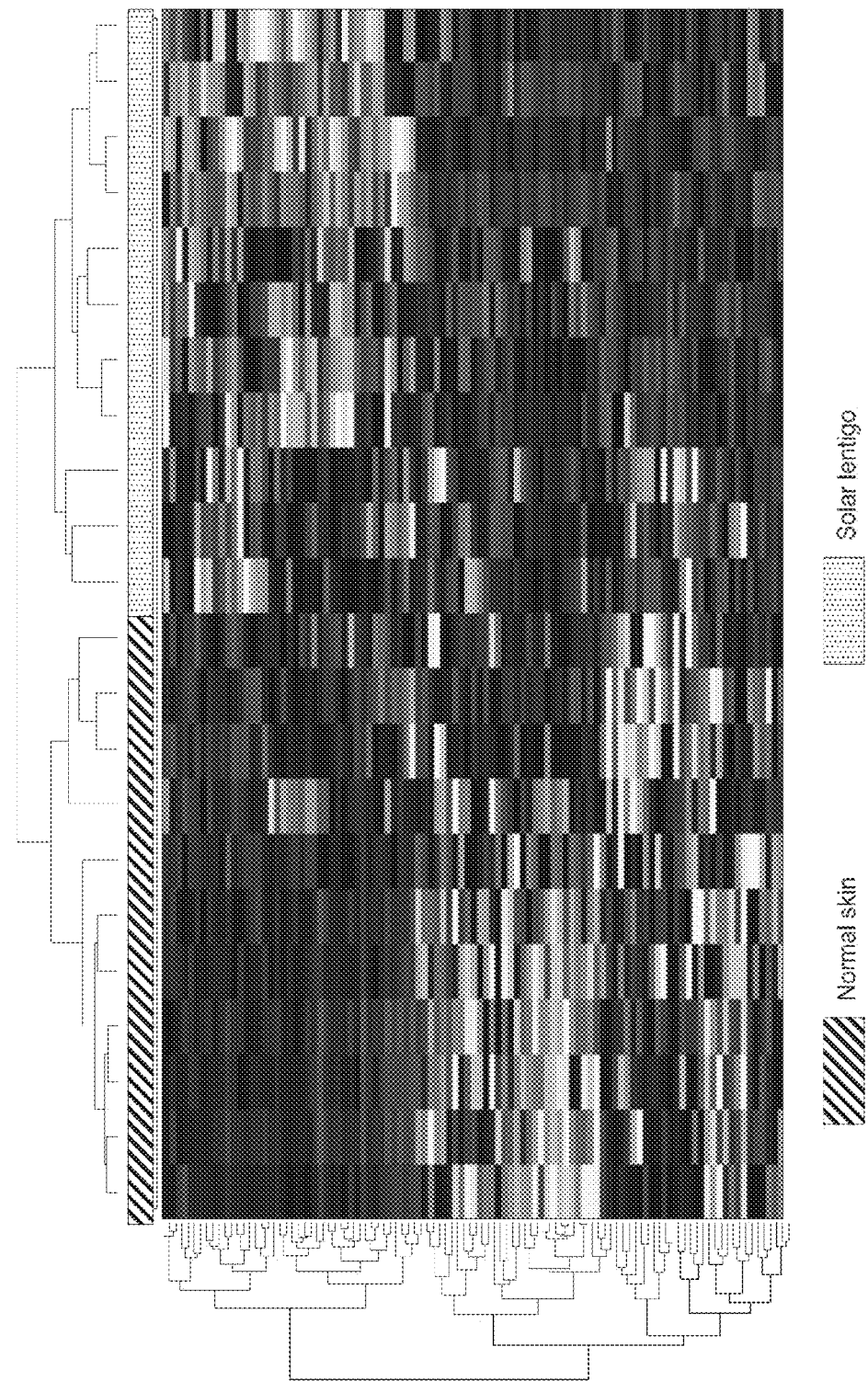
FIG. 15 is a hierarchial cluster analysis of the identified genes from FIG. 14 distinguishing solar lentigines from normal pigmented skin.
Figure 16:
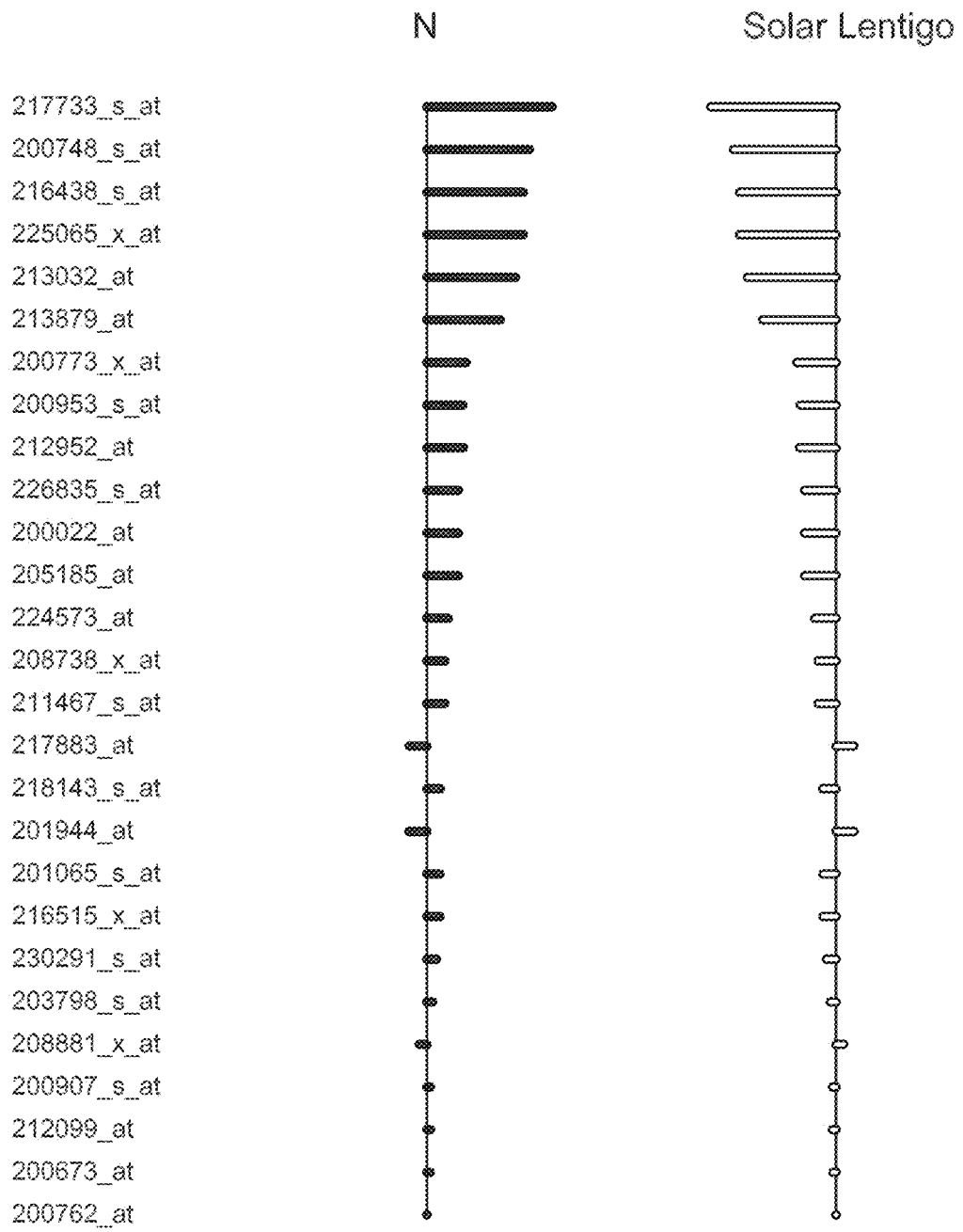
FIG. 16 is a graphical diagram showing data from prediction analysis of the developed classifiers for distinguishing solar lentigines from normal pigmented skin.

Suspicious pigmented lesions were tape stripped as above and then biopsied as per standard of care. Normal, uninvolved skin was tape stripped to serve as a negative control. All biopsies underwent primary and central review for histopathology. Total RNA was isolated provided above and then amplified and profiled, as provided above. 1600 genes that were differentially expressed among solar lentigines and normal skin controls were selected. Further testing identified a 103-gene classifier (Table 10), which may be used to discriminate solar lentigines from normal pigmented skin (FIGS. 14 to 16).

Figure 17:
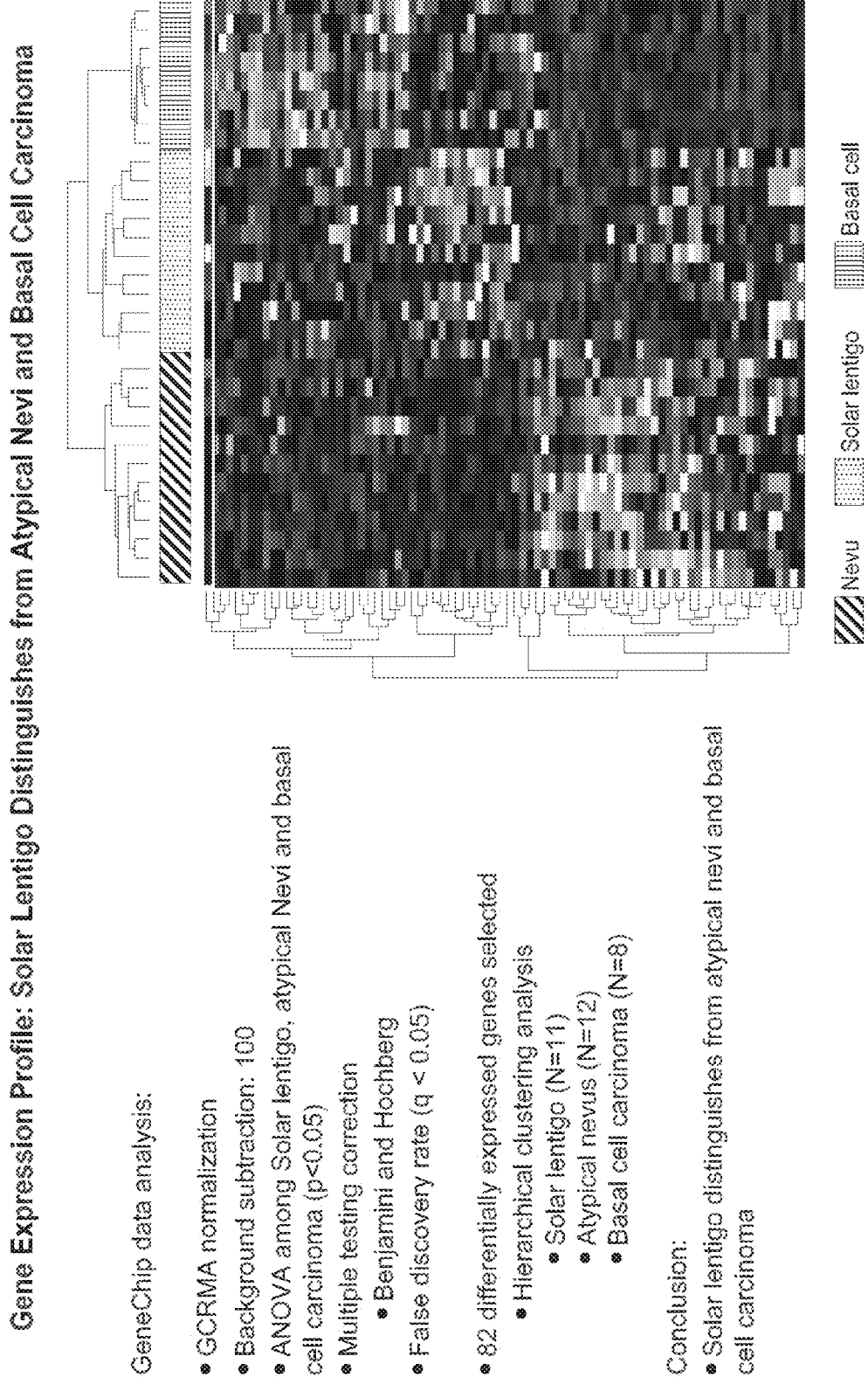
FIG. 17 is a hierarchial cluster analysis of a gene expression profile distinguishing solar lentigines from atypical nevi and basal cell carcinoma.
Figure 18:
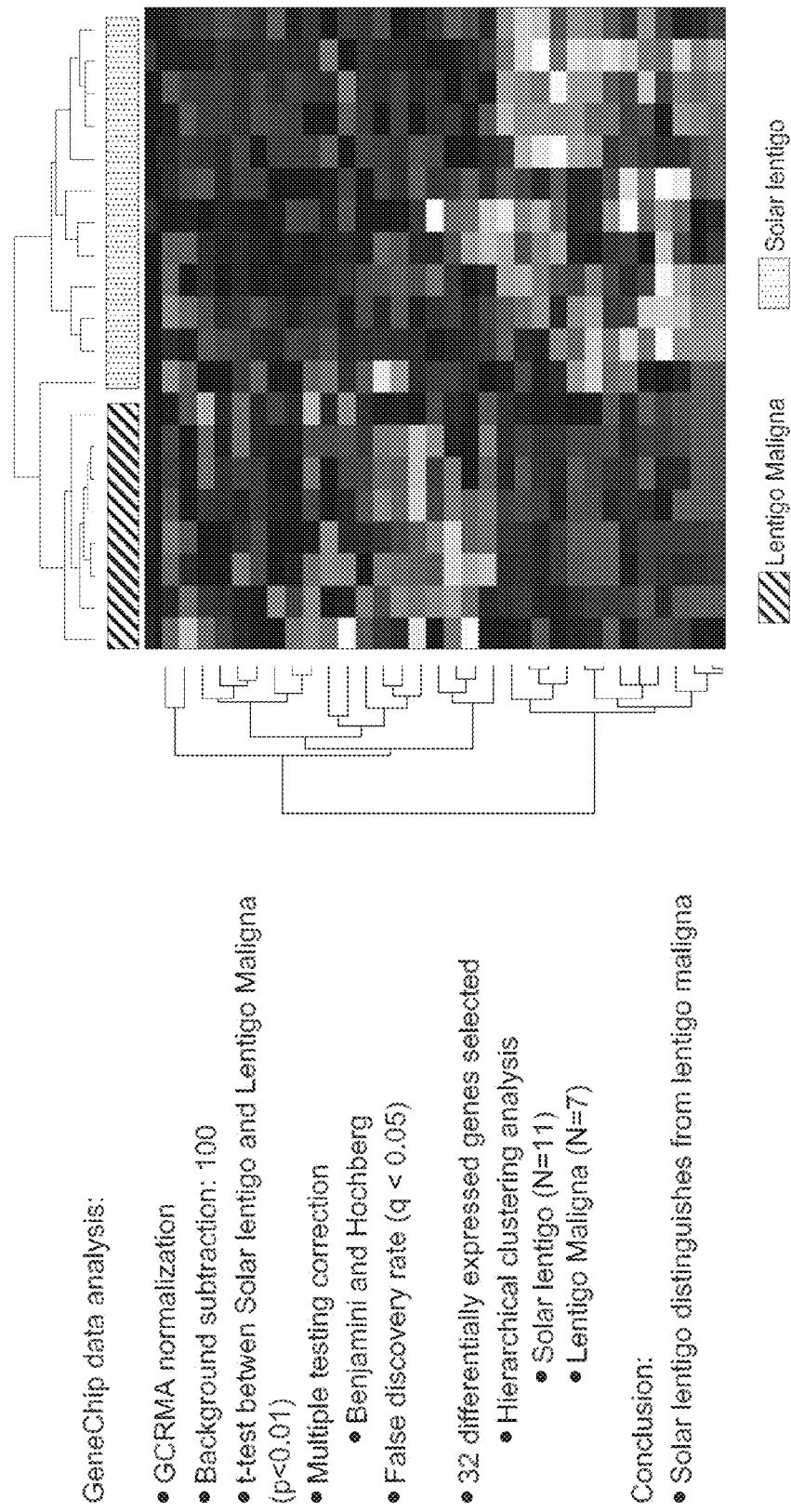
FIG. 18 is a hierarchial cluster analysis of a gene expression profile distinguishing solar lentigines from lentigo maligna.

Additional work, in which 11 solar lentigo samples, 12 atypical nevi samples, and 8 basal cell carcinoma (BCC) samples were analyzed using ANOVA (p<0.05), FDR (p<0.05) and multiple test correction to identify 82 differentially expressed genes (Table 11). Heirarchical analysis of the 82-gene classifier shows that it may be used to discriminate between solar lentigines and atypical nevi and/or basal cell carcinoma (BCC) (FIG. 17). Finally, a 32-gene classifier (Table 12) was identified, which may be used to discriminate between solar lentigines and lentigo maligna (FIG. 18). The genes and respective classifier panels were analyzed using the Prediction Analysis of Microarrays (PAM) software freely available from Stanford University (Stanford, Calif.).

Figure 19:
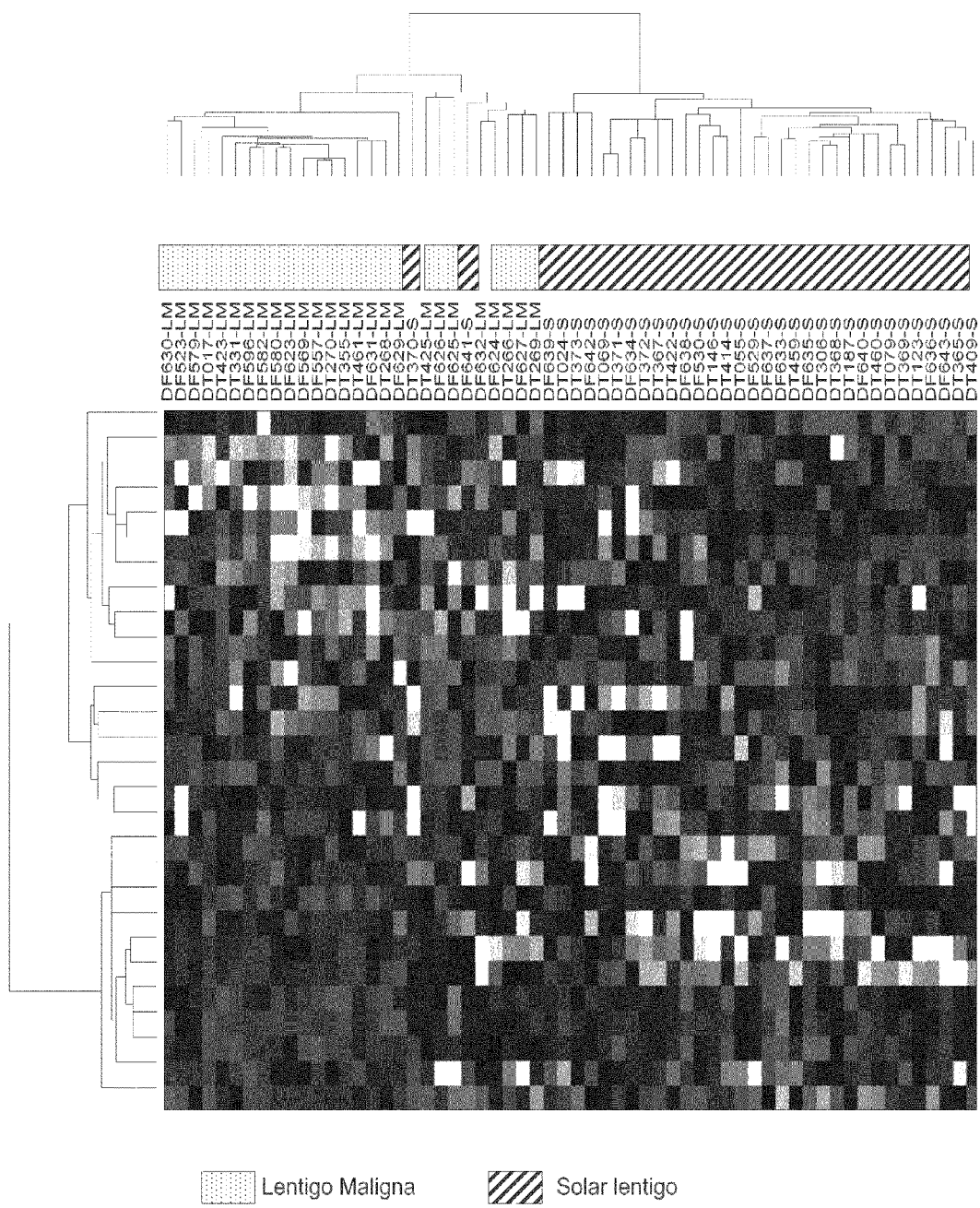
FIG. 19 is a hierarchial cluster analysis of a 28-gene classifier distinguishing solar lentigines from lentigo maligna.

An additional 28-gene classifier was identified from 2437 differentially expressed genes between lentigo maligna and solar lentigo was identified by TREENET® analysis (Table 15; see also FIG. 19). In addition, results from 26 lentigo maligna and 34 solar lentigo samples indicated that qRT-PCR recaptilated data obtained using the GeneChip microarray (see raw data in Tables 16-21).

REFERENCES

Jemal A, Murray T, Samuels A, Ghafoor A, Ward E, Thun M J: Cancer statistics, 2003. *CA Cancer J Clin* 2003, 53(1): 5-26.

Gloster H M, Jr., Brodland D G: The epidemiology of skin cancer. *Dermatol Surg* 1996, 22(3):217-226.

Albert V A, Koh H K, Geller A C, Miller D R, Prout M N, Lew R A: Years of potential life lost: another indicator of the impact of cutaneous malignant melanoma on society. *J Am Acad Dermatol* 1990, 23(2 Pt 1):308-310.

Morhenn V B, Chang E Y, Rheins L A: A noninvasive method for quantifying and distinguishing inflammatory skin reactions. *J Am Acad Dermatol* 1999, 41(5 Pt 1):687-692.

Wong R, Tran V, Morhenn V, Hung S P, Andersen B, Ito E, Wesley Hatfield G, Benson N R: Use of RT-PCR and DNA microarrays to characterize RNA recovered by non-invasive tape harvesting of normal and inflamed skin. *J Invest Dermatol* 2004, 123(1):159-167.

Benson N R, Papenfuss J, Wong R, Motaal A, Tran V, Panko J, Krueger G G: An analysis of select pathogenic messages in lesional and non-lesional skin using non-invasive tape harvesting. *Journal of Investigative Dermatology* 2006, 126(10):2234-2241.

Baldi A, Santini D, De Luca A, Paggi M G: cDNA array technology in melanoma: an overview. *J Cell Physiol* 2003, 196(2):219-223.

Carr K M, Bittner M, Trent J M: Gene-expression profiling in human cutaneous melanoma. *Oncogene* 2003, 22(20): 3076-3080.

Gershenwald J E, Bar-Eli M: Gene expression profiling of human cutaneous melanoma: are we there yet? *Cancer Biol Ther* 2004, 3(1):121-123.

Kim C J, Reintgen D S, Yeatman T J: The promise of microarray technology in melanoma care. *Cancer Control* 2002, 9(1):49-53.

Seftor R E, Seftor E A, Koshikawa N, Meltzer P S, Gardner L M, Bilban M, Stetler-Stevenson W G, Quaranta V, Hendrix M J: Cooperative interactions of laminin 5 gamma2 chain, matrix metalloproteinase-2, and membrane type-1-matrix/metalloproteinase are required for mimicry of embryonic vasculogenesis by aggressive melanoma. *Cancer Res* 2001, 61(17):6322-6327.

Su Y A, Bittner M L, Chen Y, Tao L, Jiang Y, Zhang Y, Stephan D A, Trent J M: Identification of tumor-suppressor genes using human melanoma cell lines UACC903, UACC903(+6), and SRS3 by comparison of expression profiles. *Mol Carcinog* 2000, 28(2): 119-127.

Haqq C, Nosrati M, Sudilovsky D, Crothers J, Khodabakhsh D, Pulliam B L, Federman S, Miller J R, 3rd, Allen R E, Singer M I et al: The gene expression signatures of melanoma progression. *Proc Natl Acad Sci USA* 2005, 102(17): 6092-6097.

Paik S, Shak S, Tang G, Kim C, Baker J, Cronin M, Baehner F L, Walker M G, Watson D, Park T et al: A multigene assay to predict recurrence of tamoxifen-treated, node-negative breast cancer. *N Engl J Med* 2004, 351(27):2817-2826.

Pavey S, Johansson P, Packer L, Taylor J, Stark M, Pollock P M, Walker G J, Boyle G M, Harper U, Cozzi S J et al: Microarray expression profiling in melanoma reveals a BRAF mutation signature. *Oncogene* 2004, 23(23):4060-4067.

McCarty M F, Bielenberg D R, Nilsson M B, Gershenwald J E, Barnhill R L, Ahearne P, Bucana C D, Fidler I J: Epidermal hyperplasia overlying human melanoma correlates with tumour depth and angiogenesis. *Melanoma Res* 2003, 13(4): 379-387.

Stolz W, Schmoeckel C, Welkovich B, Braun-Falco O: Semiquantitative analysis of histologic criteria in thin malignant melanomas. *J Am Acad Dermatol* 1989, 20(6): 1115-1120.

Wu Z, Irizarry R A: Stochastic models inspired by hybridization theory for short oligonucleotide arrays. *J Comput Biol* 2005, 12(6):882-893.

Wu Z, Irizarry R A: Preprocessing of oligonucleotide array data. *Nat Biotechnol* 2004, 22(6):656-658; author reply 658.

Smyth G K, Yang Y H, Speed T: Statistical issues in cDNA microarray data analysis. *Methods Mol Biol* 2003, 224: 111-136.

Lee M-LT: Analysis of microarray gene expression data. Boston: Kluwer Academic Publishers; 2004.

Stuart R O, Wachsman W, Berry C C, Wang-Rodriguez J, Wasserman L, Klacansky I, Masys D, Arden K, Goodison S, McClelland M et al: In silico dissection of cell-type-associated patterns of gene expression in prostate cancer. *Proc Natl Acad Sci USA* 2004, 101(2):615-620.

Mitchell R, Chiang C Y, Berry C, Bushman F: Global analysis of cellular transcription following infection with an HIV-based vector. *Mol Ther* 2003, 8(4):674-687.

Wolyn D J, Borevitz J O, Loudet O, Schwartz C, Maloof J, Ecker J R, Berry C C, Chory J: Light-response quantitative trait loci identified with composite interval and eXtreme array mapping in *Arabidopsis thaliana*. *Genetics* 2004, 167(2):907-917.

Borevitz J O, Liang D, Plouffe D, Chang H S, Zhu T, Weigel D, Berry C C, Winzeler E, Chory J: Large-scale identification of single-feature polymorphisms in complex genomes. *Genome Res* 2003, 13(3):513-523.

Efron B, Tibshirani R: Empirical bayes methods and false discovery rates for microarrays. *Genet Epidemiol* 2002, 23(1):70-86.

Hastie T, Tibshirani R, Friedman J: The elements of statistical learning: Date mining, inference, and prediction. New York: Springer-Verlag; 2001.

Tibshirani R, Hastie T, Narasimhan B, Chu G: Diagnosis of multiple cancer types by shrunken centroids of gene expression. *Proc Natl Acad Sci USA* 2002, 99(10):6567-6572.

Brieman L, Friedman J, Olshen R, Stone C: Classification and regression trees. Belmont, Calif.: Wadsworth International Group; 1984.

Edelman E, Porrello A, Guinney J, Balakumaran B, Bild A, Febbo P G, Mukherjee S: Analysis of sample set enrichment scores: assaying the enrichment of sets of genes for individual samples in genome-wide expression profiles. *Bioinformatics* 2006, 22(14):e108-116.

Kong S W, Pu W T, Park P J: A multivariate approach for integrating genome-wide expression data and biological knowledge. *Bioinformatics* 2006.

Pang H, Lin A, Holford M, Enerson B E, Lu B, Lawton M P, Floyd E, Zhao H: Pathway analysis using random forests classification and regression. *Bioinformatics* 2006, 22(16):2028-2036.

Page G P, Edwards J W, Gadbury G L, Yelisetti P, Wang J, Trivedi P, Allison D B: The PowerAtlas: a power and sample size atlas for microarray experimental design and research. *BMC Bioinformatics* 2006, 7:84.

TABLE 1

| name | matched term | synonym | description | Entrez Gene ID for Human | Entrez Gene ID for Mouse | Entrez Gene ID for Rat |
|---|---|---|---|---|---|---|
| ACTR1B (includes EG: 10120) | 202135_s_at | 2310066K23Rik, AA960180, ACTR1B, AI851923, ARP1B, CTRN2, MGC36526 | ARP1 actin-related protein 1 homolog B, centractin beta (yeast) | 10120 | 226977 | |
| ANGEL1 | 213099_at | 1110030H02Rik, KIAA0759, mKIAA0759, RGD1306238 | angel homolog 1 (*Drosophila*) | 23357 | 68737 | 362765 |
| ANKRD13B | 227720_at | AW124583, B930093C12Rik, FLJ20418, FLJ25555, RGD1564005 | ankyrin repeat domain 13B | 124930 | 268445 | 360575 |
| ANKRD44 | 228471_at | 4930444A19Rik, A130096K20, E130014H08Rik, LOC91526, MGC21968, MGC70444, RGD1561893 | ankyrin repeat domain 44 | 91526 | 329154 | 301415 |
| ARHGEF19 | 226857_at | 6030432F23, 6430573B13Rik, FLJ33962, RP4-733M16.1, WGEF | Rho guanine nucleotide exchange factor (GEF) 19 | 128272 | 213649 | 362648 |
| ATPBD4 | 238662_at | 5730421E18Rik, MGC14798, RGD1310006 | ATP binding domain 4 | 89978 | 66632 | 362191 |
| BARX2 | 210419_at | 2310006E12Rik, Barx2b, MGC133368, MGC133369 | BarH-like homeobox 2 | 8538 | 12023 | |
| BDNF | 206382_s_at | MGC105254, MGC34632 | brain-derived neurotrophic factor | 627 | 12064 | 24225 |
| BLOC1S1 | 202592_at | AI839753, BLOC-1 subunit 1, BLOS1, GCN5-like protein 1, GCN5L1, MGC87455, RT14 | biogenesis of lysosome-related organelles complex-1, subunit 1 | 2647 | 14533 | 288785 |
| BTG2 | 201236_s_at | AA959598, Agl, An, an-1, APRO1, MGC126063, MGC126064, PC3, TIS21 | BTG family, member 2 | 7832 | 12227 | 29619 |
| C16ORF48 | 223407_at | AI606951, DAKV6410, DKFZP434A1319, E130303B06Rik, RGD1307357 | chromosome 16 open reading frame 48 | 84080 | 102124 | 291975 |
| C6ORF218 | 244829_at | MGC40222 | chromosome 6 open reading frame 218 | 221718 | | |

TABLE 1-continued

| name | matched term | synonym | description | Entrez Gene ID for Human | Entrez Gene ID for Mouse | Entrez Gene ID for Rat |
|---|---|---|---|---|---|---|
| C8ORF13 | 233641_s_at | A030013D21, BC065085, D8S265, DKFZp761G151, MGC120649, MGC120650, MGC120651, RGD1561302 | chromosome 8 open reading frame 13 | 83648 | 219148 | 498533 |
| CCDC95 | 227286_at | AI225782, AI854876, Ccdc85, FLJ00079, FLJ90652, MGC31515 | coiled-coil domain containing 95 | 283899 | 233875 | |
| CCHCR1 | 37425_g_at | C6orf18, HCR, MGC126371, MGC126372, MGC28303, RGD: 1302992, SBP | coiled-coil alpha-helical rod protein 1 | 54535 | 240084 | 406196 |
| CIRBP | 230142_s_at | A18 HNRNP, CIRP, R74941 | cold inducible RNA binding protein | 1153 | 12696 | 81825 |
| CLSTN2 | 219414_at | 2900042C18Rik, AI448973, alcagamma, CS2, Cst-2, CSTN2, FLJ39113, FLJ39499, KIAA4134, MGC119560, mKIAA4134 | calsyntenin 2 | 64084 | 64085 | 171394 |
| COL7A1 | 217312_s_at | AW209154, EBD1, EBDCT, EBR1 | collagen, type VII, alpha 1 (epidermolysis bullosa, dystrophic, dominant and recessive) | 1294 | 12836 | 301012 |
| DACH1 | 205471_s_at, 205472_s_at, 228915_at | AI182278, Dac, DACH, E130112M23Rik, FLJ10138 | dachshund homolog 1 (*Drosophila*) | 1602 | 13134 | |
| DCT | 205337_at, 205338_s_at | DT, RGD1564975, slaty, slt, TRP-2, TYRP2 | dopachrome tautomerase (dopachrome delta-isomerase, tyrosine-related protein 2) | 1638 | 13190 | 290484 |
| DOCK10 | 219279_at | 9330153B10RIK, A630054M16Rik, DKFZp781A1532, DRIP2, Jr4, Jr5, mKIAA0694, Nbla10300, R75174, RGD1561963, ZIZ3, Zizimin3 | dedicator of cytokinesis 10 | 55619 | 210293 | 301556 |
| DRAP1 | 1556181_at | 2310074H19Rik, MGC156767, NC2-ALPHA, negative cofactor 2 alpha | DR1-associated protein 1 (negative cofactor 2 alpha) | 10589 | 66556 | 293674 |
| EDNRB | 204271_s_at, 206701_x_at | ABCDS, AU022549, Ednra, ET> B<, ET-B, ETB RECEPTOR, ETBR, ETRB, GUSB, HSCR, HSCR2, Sox10m1 | endothelin receptor type B | 1910 | 13618 | 50672 |
| EFNA4 | 205107_s_at | EFL-4, EPHRIN A4, Epl4, EPLG4, LERK-4, MGC125826 | ephrin-A4 | 1945 | 13639 | 310643 |

TABLE 1-continued

| name | matched term | synonym | description | Entrez Gene ID for Human | Entrez Gene ID for Mouse | Entrez Gene ID for Rat |
|---|---|---|---|---|---|---|
| EHD2 | 45297_at | BC027084, C130052H20Rik, MGC25606, MGC38650, MGEPS, PAST2 | EH-domain containing 2 | 30846 | 259300 | 361512 |
| ETS1 | 224833_at | AI196000, AI448617, C-ETS1, D230050P06, Etsoncb, EWSR2, FLJ10768, MGC124638, MGC130355, MGC18571, p42 ETS1, p51 ETS1, Tpl1 | v-ets erythroblastosis virus E26 oncogene homolog 1 (avian) | 2113 | 23871 | 24356 |
| FAM33A | 225684_at | 1110001A07Rik, C78640, EG625534, FLJ12758, MGC109093, MGC110975, MGC151378, RGD1307084 | family with sequence similarity 33, member A | 348235 | 66140\|625534 | 287598 |
| FGFR1 | 210973_s_at, 211535_s_at | AW208770, BFGFR, C-FGR, CD331, CEK, FGF1 RECEPTOR, FGFBR, FGFR1-IIIC, Fgfr1c, FLG, Flk2, FLT2, H5, HBGFR, KAL2, N-SAM | fibroblast growth factor receptor 1 (fms-related tyrosine kinase 2, Pfeiffer syndrome) | 2260 | 14182 | 79114 |
| FOXO1A | 202723_s_at | Afxh, AI876417, FKH1, FKHR, FKHR1, Forkhead, FOXO1 | forkhead box O1A (rhabdomyosarcoma) | 2308 | 56458 | 84482 |
| FOXP1 | 223936_s_at | 12CC4, 3110052D19Rik, 4932443N09Rik, AI461938, AW494214, FLJ23741, hFKH1B, HSPC215, MGC116362, MGC12942, MGC88572, MGC99551, QRF1 | forkhead box P1 | 27086 | 108655 | 297480 |
| FRAT2 | 209864_at | MGC10562, MGC37615 | frequently rearranged in advanced T-cell lymphomas 2 | 23401 | 212398 | |
| GCLM | 203925_at | Gamma gclm, Gamma glutamylcysteine synthase (regulatory), GAMMA GLUTAMYLCYSTEINE SYNTHETASE, Gcs Ls, Gcs, Regulatory, GCS-L, GCS1, Gcslc, GLCLR, glutamat-cystein ligase, regulatory subunit | glutamate-cysteine ligase, modifier subunit | 2730 | 14630 | 29739 |
| GGA3 | 209411_s_at | C230037M19Rik, KIAA0154, mKIAA0154 | golgi associated, gamma adaptin ear containing, ARF binding protein 3 | 23163 | 260302 | 360658 |

TABLE 1-continued

| name | matched term | synonym | description | Entrez Gene ID for Human | Entrez Gene ID for Mouse | Entrez Gene ID for Rat |
|---|---|---|---|---|---|---|
| GLUL | 200648_s_at | GLNS, Glutamine Synthase, GLUTAMINE SYNTHETASE, GS, MGC128403, PIG43 | glutamate-ammonia ligase (glutamine synthetase) | 2752 | 14645 | |
| GPR161 | 214104_at | FLJ33952, G-protein coupled receptor af091890, Gm208, Gm208Gpr, RE2, RGD1563245 | G protein-coupled receptor 161 | 23432 | 240888 | 289180 |
| HEY2 | 219743_at | CHF1, GRL, HERP1, HESR2, HRT2, MGC10720 | hairy/enhancer-of-split related with YRPW motif 2 | 23493 | 15214 | 155430 |
| HIST2H2AA3 | 214290_s_at | AI448581, H2A, H2a-615, H2A.2, H2A/O, H2A/q, H2AFO, Hist2, HIST2H2AA, Hist2h2aa1 | histone cluster 2, H2aa3 | 8337 | 15267 | 365877 |
| ID1 | 208937_s_at | AI323524, D2Wsu140e, ID, ID-1H, ID125A, Idb1, MGC156482 | inhibitor of DNA binding 1, dominant negative helix-loop-helix protein | 3397 | 15901 | 25261 |
| KALRN | 227750_at | 2210407G14Rik, AV235988, DUET, Duo, E530005C20Rik, FLJ16443, Gm539, HAPIP, KALIRIN, Kalirin7, Pcip10, TRAD | kalirin, RhoGEF kinase | 8997 | 545156 | 84009 |
| KDELR1 | 200922_at | 8030486F04Rik, AW215843, ERD2, ERD2.1, HDEL, KDEL RECEPTOR, Kdelr, MGC109169, PM23 | KDEL (Lys-Asp-Glu-Leu) endoplasmic reticulum protein retention receptor 1 | 10945 | 68137 | 361577 |
| KIAA0738 | 210529_s_at | 2810407D09Rik, 3321401G04Rik, A230020K05Rik, AI848529, RGD1565474 | KIAA0738 gene product | 9747 | 77574 | 362353 |
| KIT | 205051_s_at | Bs, C-KIT, c-Kit Gnnk+, CD117, Fdc, SCFR, Ssm, Tr Kit, white-spotted | v-kit Hardy-Zuckerman 4 feline sarcoma viral oncogene homolog | 3815 | 16590 | 64030 |
| LGR4 | 230674_at | 9130225G07, A930009A08Rik, GPCR48, GPR48 | leucine-rich repeat-containing G protein-coupled receptor 4 | 55366 | 107515 | 286994 |
| LHX2 (includes EG: 9355) | 211219_s_at | ap, apterous, hLhx2, Lh-2, LH2A, Lhx2, Lim2, MGC138390 | LIM homeobox 2 | 9355 | 16870 | 296706 |
| LMO4 | 209204_at | A730077C12Rik, Crp3, Etohi4, MGC105593 | LIM domain only 4 | 8543 | 16911 | 362051 |
| LOC254100 | 1557131_at | | hypothetical protein LOC254100 | 254100 | | |
| LRIG1 | 236173_s_at, 238339_x_at | D6Bwg0781e, DKFZP586O1624, Img, LIG-1 | leucine-rich repeats and immunoglobulin-like domains 1 | 26018 | 16206 | 312574 |

TABLE 1-continued

| name | matched term | synonym | description | Entrez Gene ID for Human | Entrez Gene ID for Mouse | Entrez Gene ID for Rat |
|---|---|---|---|---|---|---|
| MED28 | 222635_s_at | 1500003D12Rik, AI451633, AU045690, DKFZP434N185, EG1, FKSG20, magicin, RGD1305875 | mediator of RNA polymerase II transcription, subunit 28 homolog (*S. cerevisiae*) | 80306 | 66999 | 305391 |
| MKL1 | 215292_s_at | AI852829, AMKL, AW743281, AW821984, BSAC, MAL, MRTF-A | megakaryoblastic leukemia (translocation) 1 | 57591 | 223701 | 315151 |
| MLANA | 206426_at, 206427_s_at | A930034P04Rik, MART-1, MELAN-A, MGC130556 | melan-A | 2315 | 77836 | 293890 |
| MLLT6 | 225628_s_at | AF17, AI315037, FLJ23480 | myeloid/lymphoid or mixed-lineage leukemia (trithorax homolog, *Drosophila*); translocated to, 6 | 4302 | 246198 | 303504 |
| MLPH | 218211_s_at | 2210418F23Rik, 5031433I09Rik, AW228792, D1Wsu84e, l(1)-3Rk, 11Rk3, ln, MGC2771, MGC59733, SLAC2-A | melanophilin | 79083 | 171531 | 316620 |
| MYEF2 | 222771_s_at, 232676_x_at | 9430071B01, FLJ11213, HsT18564, KIAA1341, MEF-2, MGC109392, MGC87325, mKIAA1341, MST156, MSTP156 | myelin expression factor 2 | 50804 | 17876 | 362207 |
| MYL6B | 204173_at | 5730437E04Rik, Atrial Myosin Light Chain 1, BC037527, MGC41229, MLC1SA, RGD1560334 | myosin, light chain 6B, alkali, smooth muscle and non-muscle | 140465 | 216459 | 317454 |
| MYO5A | 227761_at | 9630007J19Rik, AI413174, AI661011, Br Myosin5a, d-120J, Dbv, Dop, flail, flr, GS1, hcBM-V, MVa, MYH12, MYO5, myosin V, MYOSIN VA, MYOSIN VA EXON CONTAINING, MYOVA, MYOXIN, MYR12, Sev-1 | myosin VA (heavy chain 12, myoxin) | 4644 | 17918 | 25017 |
| NBL1 | 37005_at | D1S1733E, D4H1S1733E, DAN, Dana, DAND1, MGC123430, MGC8972, NB, NO3 | neuroblastoma, suppression of tumorigenicity 1 | 4681 | 17965 | 50594 |

TABLE 1-continued

| name | matched term | synonym | description | Entrez Gene ID for Human | Entrez Gene ID for Mouse | Entrez Gene ID for Rat |
|---|---|---|---|---|---|---|
| NFIB | 230791_at | 6720429L07Rik, CTF/NF1B, E030026I10Rik, NF1-B, NFI-RED, NFIB2, NFIB3, Nuclear factor 1/B | nuclear factor I/B | 4781 | 18028 | 29227 |
| OSTM1 | 218196_at | 1200002H13Rik, AW123348, GIPN, GL, HSPC019 | osteopetrosis associated transmembrane protein 1 | 28962 | 14628 | 445370 |
| PDK3 | 221957_at | 2610001M10Rik, AI035637, MGC6383 | pyruvate dehydrogenase kinase, isozyme 3 | 5165 | 236900 | 296849 |
| PKD1 | 241090_at | FLJ00285, mFLJ00285, MGC118471, PBP, PC-1, POLYCYSTIN1 | polycystic kidney disease 1 (autosomal dominant) | 5310 | 18763 | 24650 |
| PLEKHA5 | 220952_s_at | 2810431N21Rik, AI428202, AK129423, Ayu21-9, FLJ10667, FLJ31492, Gt(pU21)9Imeg, Image: 3710928, KIAA1686, MGC38455, PEPP2, TRS1 | pleckstrin homology domain containing, family A member 5 | 54477 | 109135 | 246237 |
| PLP1 | 210198_s_at | DM20, jimpy, jp, MMPL, Msd, PLP, PLP/DM20, PMD, PROTEOLIPID, RSH, SPG2 | proteolipid protein 1 (Pelizaeus-Merzbacher disease, spastic paraplegia 2, uncomplicated) | 5354 | 18823 | 24943 |
| PLXNC1 | 213241_at | 2510048K12Rik, AW742158, CD232, Plexin C1, VESPR | plexin C1 | 10154 | 54712 | 362873 |
| PPP3CA | 202425_x_at | 2900074D19Rik, AI841391, AW413465, Calcineurin, Calcineurin A Alpha, CALN, CALNA, CALNA1, CCN1, CN, CnA, CnA-alpha, CNA1, MGC106804, Pp2b Subunit A, PPP2B | protein phosphatase 3 (formerly 2B), catalytic subunit, alpha isoform (calcineurin A alpha) | 5530 | 19055 | 24674 |
| PRKCSH | 200707_at | 80K-H, AGE-R2, G19P1, PCLD, PLD, PLD1 | protein kinase C substrate 80K-H | 5589 | 19089 | 300445 |
| PRKD3 | 222565_s_at | 4930557O20Rik, 5730497N19Rik, EPK2, MGC47171, nPKC-NU, PKC-NU, PKD3, PRKCN | protein kinase D3 | 23683 | 75292 | 313834 |
| PRMT1 | 206445_s_at | 6720434D09Rik, ANM1, AW214366, HCP1, heterogeneous ribonucleooproteins methyltransferase-like 2, Hnmtl2, Hramt, HRMT1L2, IR1B4, Mrmt1 | protein arginine methyltransferase 1 | 3276 | 15469 | 60421 |

TABLE 1-continued

| name | matched term | synonym | description | Entrez Gene ID for Human | Entrez Gene ID for Mouse | Entrez Gene ID for Rat |
|---|---|---|---|---|---|---|
| PSCD3 | 225147_at | AI648983, ARNO3, CYTOHESIN-3, GRP1, KIAA4241, MGC124579, mKIAA4241, Sec7, Sec7C | pleckstrin homology, Sec7 and coiled-coil domains 3 | 9265 | 19159 | 116693 |
| PTPRF | 200635_s_at, 200637_s_at | AA591035, FLJ43335, FLJ45062, FLJ45567, LAR, Lar ptp2b, LARFN5C, LARS | protein tyrosine phosphatase, receptor type, F | 5792 | 19268 | 360406 |
| PTPRM | 1555579_s_at | HR-PTPU, KIAA4044, MGC90724, mKIAA4044, PTP-MU, PTPRL1, R-PTP-MU, RPTPM, RPTPU | protein tyrosine phosphatase, receptor type, M | 5797 | 19274 | 29616 |
| PVRL1 | 225211_at | AI835281, AW549174, CD111, CLPED1, ED4, HIgR, HVEC, MGC142031, MGC16207, NECTIN-1, Nectin1 alpha, Nectin1 delta, OFC7, PRR, PRR1, PVRR, PVRR1, SK-12 | poliovirus receptor-related 1 (herpesvirus entry mediator C; nectin) | 5818 | 58235 | 192183 |
| RAB40C | 227269_s_at | RAB40, RAR3, RARL, RASL8C | RAB40C, member RAS oncogene family | 57799 | 224624 | 359728 |
| RASSF3 | 230466_s_at | AW212023, AW322379, MGC119194, MGC119195, MGC119197, RASSF5 | Ras association (RalGDS/AF-6) domain family 3 | 283349 | 192678 | 362886 |
| RHOQ | 212120_at | ARHQ, RASL7A, Rhot, TC10, TC10 BETA, TC10A | ras homolog gene family, member Q | 23433 | 104215 | 85428 |
| SAT1 | 203455_s_at, 210592_s_at, 213988_s_at, 230333_at | AA617398, Ab2-402, DC21, KFSD, MGC72945, SAT, Spermidine/spermine N1-acetyl transferase, SSAT, SSAT-1 | spermidine/spermine N1-acetyltransferase 1 | 6303 | 20229 | 302642 |
| SDCBP | 200958_s_at | MDA-9, ST1, SYCL, SYNTENIN, Syntenin-1, TACIP18 | syndecan binding protein (syntenin) | 6386 | 53378 | 83841 |
| SEC61A1 | 217716_s_at, 222385_x_at | AA408394, AA410007, HSEC61, rSEC61alpha p, SEC61, Sec61 alpha, SEC61 ALPHA1, SEC61A | Sec61 alpha 1 subunit (*S. cerevisiae*) | 29927 | 53421 | 80843 |
| SEMA3C | 236947_at | 1110036B02Rik, SEMAE, SEMAPHORINE, SemE | sema domain, immunoglobulin domain (Ig), short basic domain, secreted, (semaphorin) 3C | 10512 | 20348 | 296787 |

TABLE 1-continued

| name | matched term | synonym | description | Entrez Gene ID for Human | Entrez Gene ID for Mouse | Entrez Gene ID for Rat |
|---|---|---|---|---|---|---|
| SERGEF | 220482_s_at, 232983_s_at | DELGEF, Gef, Gnef, Gnefr, MGC141208, MGC141209, RGD1563497 | secretion regulating guanine nucleotide exchange factor | 26297 | 27414 | 365243 |
| SILV | 209848_s_at | D10H12S53E, D12S53E, D12S53Eh, GP100, gp87, ME20, PMEL17, SI, SIL | silver homolog (mouse) | 6490 | 20431 | 362818 |
| SLC2A4RG | 227362_at | GEF, HDBP1, Si-1-2, Si-1-2-19 | SLC2A4 regulator | 56731 | | |
| SLC7A1 | 212295_s_at | 4831426K01Rik, AI447493, ATRC1, CAT-1, EcoR, ER, ERR, HCAT1, mCAT-1, Rec-1, REC1L, REV-1 | solute carrier family 7 (cationic amino acid transporter, y+ system), member 1 | 6541 | 11987 | 25648 |
| SRGAP2 | 1568957_x_at | 9930124L22Rik, AI448945, FBP2, FNBP2, KIAA0456, RGD1566016, srGAP3 | SLIT-ROBO Rho GTPase activating protein 2 | 23380 | 14270 | 360840 |
| SSBP3 | 217991_x_at, 223635_s_at | 2610021L12Rik, 2610200M23Rik, 5730488C10Rik, AI854733, AW551939, CSDP, FLJ10355, LAST, MGC124589, SSDP, SSDP1, Ssdp3 | single stranded DNA binding protein 3 | 23648 | 72475 | 84354 |
| STAM (includes EG: 8027) | 203544_s_at | DKFZp686J2352, RGD1564499, Stam, STAM1 | signal transducing adaptor molecule (SH3 domain and ITAM motif) 1 | 8027 | 20844 | 498798 |
| SYNGR2 | 201079_at | CELLUGYRIN, Clast2, MGC102914 | synaptogyrin 2 | 9144 | 20973 | 89815 |
| TCF7L2 (includes EG: 6934) | 212759_s_at | mTcf-4B, mTcf-4E, TCF-4, TCF4B, TCF4E, Tcf7l2 | transcription factor 7-like 2 (T-cell specific, HMG-box) | 6934 | 21416 | |
| TIMM17A | 215171_s_at | 17 kDa, Mitochondrial import inner membrane translocase, Mitochondrial protein import protein 2, mTim17a, TIM17, TIM17A, Timm17 | translocase of inner mitochondrial membrane 17 homolog A (yeast) | 10440 | 21854 | 54311 |
| TP53 | 201746_at | bbl, bfy, bhy, Delta N p53, LFS1, MGC112612, P53, TRP53 | tumor protein p53 (Li-Fraumeni syndrome) | 7157 | 22059 | 24842 |
| TP53INP1 | 235602_at | 2700057G22Rik, DKFZP434M1317, FLJ22139, p53DINP1, SIP, SIP18, SIP27, Stinp, Teap, Thymus Expressed Acidic Protein, TP53DINP1, TP53DINP1alpha, TP53INP1A, | tumor protein p53 inducible nuclear protein 1 | 94241 | 60599 | 297822 |

TABLE 1-continued

| name | matched term | synonym | description | Entrez Gene ID for Human | Entrez Gene ID for Mouse | Entrez Gene ID for Rat |
|---|---|---|---|---|---|---|
| TRIB2 | 202478_at | TP53INP1B, Trp53inp1 AW319517, C5fw, GS3955, RGD1564451, TRB-2 | tribbles homolog 2 (*Drosophila*) | 28951 | 217410 | 313974 |
| TRPM1 (includes EG: 4308) | 237070_at | 4732499L03Rik, AI606771, LTRPC1, melastatin, MLSN, MLSN1, Trpm1 | transient receptor potential cation channel, subfamily M, member 1 | 4308 | 17364 | |
| TSPAN6 | 209108_at | 6720473L21Rik, AI316786, MGC117923, T245, Tm4sf, TM4SF6 | tetraspanin 6 | 7105 | 56496 | 302313 |
| TSTA3 | 36936_at | AI256181, FX, FX protein, MGC113801, P35B, Tstap35b | tissue specific transplantation antigen P35B | 7264 | 22122 | 300036 |
| TTC3 | 208073_x_at, 210645_s_at | 2610202A04Rik, AA409221, D16Ium21, D16Ium21e, DCRR1, DKFZp686M0150, KIAA4119, mKIAA4119, Mtprd, RNF105, TPRD, TPRDIII | tetratricopeptide repeat domain 3 | 7267 | 22129 | 360702 |
| TUBB4 | 212664_at | AI325297, Beta tubulin, BETA TUBULIN 4 ALPHA, Beta tubulin class iv, beta-5, Beta4 Tubulin, M(beta)4, Tubb, TUBB5, TUBULIN BETA (5-BETA), TUBULIN BETA5 | tubulin, beta 4 | 10382 | 22153 | 29213 |
| TYR | 206630_at | albino, Dopa oxidase, Melanogenesis Related Tyrosinase, OCA1A, OCAIA, skc35, Tyr< c-em>, TYROSINASE | tyrosinase (oculocutaneous albinism IA) | 7299 | 22173 | 308800 |
| TYRP1 | 205694_at | b-PROTEIN, brown, CAS2, CATB, GP75, isa, MELANOMA ANTIGEN GP75, TRP, TRP-1, TYRP | tyrosinase-related protein 1 | 7306 | 22178 | 298182 |
| VDR | 204255_s_at | NR1I1, VD3R, VITAMIN D RECEPTOR | vitamin D (1,25-dihydroxyvitamin D3) receptor | 7421 | 22337 | 24873 |
| VGLL4 | 214004_s_at | BC048841, KIAA0121, MGC109514, MGC54805, VGL-4 | vestigial like 4 (*Drosophila*) | 9686 | 232334 | 297523 |

TABLE 1-continued

| name | matched term | synonym | description | Entrez Gene ID for Human | Entrez Gene ID for Mouse | Entrez Gene ID for Rat |
|---|---|---|---|---|---|---|
| YIPF5 | 224949_at | 2610311I19Rik, AA408236, Ac2-256, DKFZp313L2216, FinGER5, SB140, SMAP-5, YIP1A | Yip1 domain family, member 5 | 81555 | 67180 | 361315 |
| ZFHX1B | 1557797_a_at, 203603_s_at | 9130203F04Rik, D130016B08Rik, KIAA0569, mKIAA0569, SIP-1, SMADIP1, ZEB2, Zfx1b, Zfxh1b | zinc finger homeobox 1b | 9839 | 24136 | 311071 |
|  | 1558019_at | —: Homo sapiens, clone IMAGE: 4732650, mRNA |  |  |  |  |
|  | 233551_at | LOC642776: hypothetical protein LOC642776 |  |  |  |  |
|  | 208646_at | RPS14: ribosomal protein S14 /// similar to ribosomal protein S14 |  |  |  |  |
|  | 208929_x_at | RPL13: ribosomal protein L13 |  |  |  |  |
|  | 214351_x_at | RPL13: ribosomal protein L13 /// similar to ribosomal protein L13 |  |  |  |  |
|  | 200817_x_at | RPS10: ribosomal protein S10 |  |  |  |  |
|  | 213296_at | —: Transcribed locus |  |  |  |  |
|  | 213692_s_at | —: — |  |  |  |  |
|  | 227957_at | —: — |  |  |  |  |
|  | 232462_s_at | FLJ23569: BC040926 |  |  |  |  |
|  | 227722_at | RPS23: ribosomal protein S23 |  |  |  |  |
|  | 217466_x_at | RPS2: ribosomal protein S2 /// similar to ribosomal protein S2 |  |  |  |  |
|  | 235534_at | —: Homo sapiens, clone IMAGE: 5723825, mRNA |  |  |  |  |
|  | 230741_at | —: Full length insert cDNA clone YX74D05 |  |  |  |  |
|  | 229067_at | LOC653464: Similar to SLIT-ROBO Rho GTPase-activating protein 2 (srGAP2) (Formin0binding protein 2) |  |  |  |  |

TABLE 2

| name | matched term |
|---|---|
| ANKRD44 | 228471_at |
| ARHGEF19 | 226857_at |
| ATPBD4 | 238662_at |
| BARX2 | 210419_at |
| BDNF | 206382_s_at |
| BLOC1S1 | 202592_at |
| C16ORF48 | 223407_at |
| C6ORF218 | 244829_at |

TABLE 2-continued

| name | matched term |
|---|---|
| C8ORF13 | 233641_s_at |
| CCHCR1 | 37425_g_at |
| CIRBP | 230142_s_at |
| CLSTN2 | 219414_at |
| COL7A1 | 217312_s_at |
| DACH1 | 205472_s_at, 228915_at |
| DCT | 205337_at, 205338_s_at |
| DOCK10 | 219279_at |
| DRAP1 | 1556181_at |
| EDNRB | 204271_s_at, 206701_x_at |
| EFNA4 | 205107_s_at |
| EHD2 | 45297_at |
| ETS1 | 224833_at |
| FAM33A | 225684_at |
| FGFR1 | 210973_s_at, 211535_s_at |
| FOXO1A | 202723_s_at |
| GGA3 | 209411_s_at |
| GPR161 | 214104_at |
| HIST2H2AA3 | 214290_s_at |
| ID1 | 208937_s_at |
| KDELR1 | 200922_at |
| KIAA0738 | 210529_s_at |
| KIT | 205051_s_at |
| LGR4 | 230674_at |
| LHX2 (includes EG: 9355) | 211219_s_at |
| LMO4 | 209204_at |
| LOC254100 | 1557131_at |
| LRIG1 | 238339_x_at |
| MED28 | 222635_s_at |
| MKL1 | 215292_s_at |
| MLANA | 206426_at, 206427_s_at |
| MLPH | 218211_s_at |
| MYEF2 | 222771_s_at, 232676_x_at |
| MYO5A | 227761_at |
| NBL1 | 37005_at |
| OSTM1 | 218196_at |
| PDK3 | 221957_at |
| PKD1 | 241090_at |
| PLEKHA5 | 220952_s_at |
| PLP1 | 210198_s_at |
| PLXNC1 | 213241_at |
| PRKCSH | 200707_at |
| PRKD3 | 222565_s_at |
| PRMT1 | 206445_s_at |
| PSCD3 | 225147_at |
| PTPRF | 200637_s_at |
| PTPRM | 1555579_s_at |
| RAB40C | 227269_s_at |

TABLE 2-continued

| name | matched term |
|---|---|
| RASSF3 | 230466_s_at |
| RHOQ | 212120_at |
| RPL13 | 214351_x_at |
| RPS23 | 227722_at |
| SAT1 | 203455_s_at, 213988_s_at, 230333_at |
| SDCBP | 200958_s_at |
| SEC61A1 | 222385_x_at |
| SEMA3C | 236947_at |
| SERGEF | 232983_s_at |
| SILV | 209848_s_at |
| SLC2A4RG | 227362_at |
| SLC7A1 | 212295_s_at |
| SSBP3 | 217991_x_at, 223635_s_at |
| STAM (includes EG: 8027) | 203544_s_at |
| SYNGR2 | 201079_at |
| TCF7L2 (includes EG: 6934) | 212759_s_at |
| TIMM17A | 215171_s_at |
| TRIB2 | 202478_at |
| TRPM1 (includes EG: 4308) | 237070_at |
| TSPAN6 | 209108_at |
| TTC3 | 208073_x_at, 210645_s_at |
| TUBB4 | 212664_at |
| TYR | 206630_at |
| VDR | 204255_s_at |
| YIPF5 | 224949_at |
| ZFHX1B | 1557797_a_at, 203603_s_at |
| | 229067_at |
| | 213692_s_at |
| | 227957_at |
| | 213296_at |
| | 235534_at |
| | 233551_at |
| | 1558019_at |

TABLE 3

| matched term | description |
|---|---|
| 208073_x_at | TTC3: tetratricopeptide repeat domain 3 |
| 210645_s_at | TTC3: tetratricopeptide repeat domain 3 |
| 206630_at | TYR: tyrosinase (oculocutaneous albinism IA) |
| 203544_s_at | STAM: signal transducing adaptor molecule (SH3 domain and ITAM motif) 1 |
| 230741_at | —: Full length insert cDNA clone YX74D05 |

TABLE 4

| matched term | description |
|---|---|
| 205694_at | TYRP1: tyrosinase-related protein 1 |
| 206427_s_at | MLANA: melan-A |
| 206140_at | LHX2: LIM homeobox 2 |
| 206630_at | TYR: tyrosinase (oculocutaneous albinism IA) |
| 203921_at | CHST2: carbohydrate (N-acetylglucosamine-6-O) sulfotransferase 2 |
| 205337_at | DCT: dopachrome tautomerase (dopachrome delta-isomerase, tyrosine-related protein 2) |
| 228245_s_at | OVOS2: ovostatin 2 /// similar to cDNA sequence BC048546 |
| 205338_s_at | DCT: dopachrome tautomerase (dopachrome delta-isomerase, tyrosine-related protein 2) |
| 1557797_a_at | ZFHX1B: Zinc finger homeobox 1b |
| 204271_s_at | EDNRB: endothelin receptor type B |
| 237070_at | TRPM1: transient receptor potential cation channel, subfamily M, member 1 |
| 200716_x_at | RPL13A: ribosomal protein L13a |
| 1555579_s_at | PTPRM: protein tyrosine phosphatase, receptor type, M |
| 205051_s_at | KIT: v-kit Hardy-Zuckerman 4 feline sarcoma viral oncogene homolog |
| 200665_s_at | SPARC: secreted protein, acidic, cysteine-rich (osteonectin) /// secreted protein, acidic, cysteine-rich (osteonectin) |
| 205174_s_at | QPCT: glutaminyl-peptide cyclotransferase (glutaminyl cyclase) |
| 200725_x_at | RPL10: ribosomal protein L10 |
| 232602_at | WFDC3: WAP four-disulfide core domain 3 |
| 202478_at | TRIB2: tribbles homolog 2 (*Drosophila*) |
| 209230_s_at | P8: p8 protein (candidate of metastasis 1) |
| 232676_x_at | MYEF2: myelin expression factor 2 |
| 222565_s_at | PRKD3: protein kinase D3 |

TABLE 4-continued

| matched term | description |
| --- | --- |
| 212295_s_at | SLC7A1: solute carrier family 7 (cationic amino acid transporter, y+ system), member 1 |
| 212594_at | PDCD4: programmed cell death 4 (neoplastic transformation inhibitor) |
| 218211_s_at | MLPH: melanophilin |
| 206426_at | MLANA: melan-A |
| 207065_at | K6HF: cytokeratin type II |
| 202500_at | DNAJB2: DnaJ (Hsp40) homolog, subfamily B, member 2 |
| 203706_s_at | FZD7: frizzled homolog 7 (*Drosophila*) |
| 209969_s_at | STAT1: signal transducer and activator of transcription 1, 91 kDa |

TABLE 5

| matched term | description |
| --- | --- |
| 205694_at | tyrosinase-related protein 1 |
| 206140_at | LIM homeobox 2 |
| 206427_s_at | melan-A |
| 203455_s_at | spermidine/spermine N1-acetyltransferase |
| 206453_s_at | NDRG family member 2 |
| 203921_at | carbohydrate (N-acetylglucosamine-6-O) sulfotransferase 2 |
| 200958_s_at | syndecan binding protein (syntenin) |
| 209283_at | crystallin, alpha B |
| 204271_s_at | endothelin receptor type B |
| 208073_x_at | tetratricopeptide repeat domain 3 |
| 232602_at | WAP four-disulfide core domain 3 |
| 202435_s_at | cytochrome P450, family 1, subfamily B, polypeptide 1 |
| 209230_s_at | p8 protein (candidate of metastasis 1) |
| 208966_x_at | interferon, gamma-inducible protein 16 |
| 205337_at | dopachrome tautomerase (dopachrome delta-isomerase, tyrosine-related protein 2) |
| 202088_at | solute carrier family 39 (zinc transporter), member 6 |
| 211538_s_at | heat shock 70 kDa protein 2 |
| 201556_s_at | vesicle-associated membrane protein 2 (synaptobrevin 2) |
| 241455_at | Similar to AI661453 protein |
| 237070_at | transient receptor potential cation channel, subfamily M, member 1 |

TABLE 6

| matched term | description |
| --- | --- |
| 1555505_a_at | tyrosinase (oculocutaneous albinism IA) |
| 204271_s_at | endothelin receptor type B |
| 208073_x_at | tetratricopeptide repeat domain 3 |
| 200958_s_at | syndecan binding protein (syntenin) |
| 205051_s_at | v-kit Hardy-Zuckerman 4 feline sarcoma viral oncogene homolog |
| 201245_s_at | OTU domain, ubiquitin aldehyde binding 1 |
| 201603_at | protein phosphatase 1, regulatory (inhibitor) subunit 12A |
| 201605_x_at | calponin 2 |
| 201908_at | dishevelled, dsh homolog 3 (*Drosophila*) |
| 202478_at | tribbles homolog 2 (*Drosophila*) |
| 1557292_a_at | mucolipin 3 |
| 200601_at | actinin, alpha 4 |
| 200819_s_at | ribosomal protein S15 |
| 209953_s_at | CDC37 cell division cycle 37 homolog (*S. cerevisiae*) |
| 213146_at | jumonji domain containing 3 |
| 222670_s_at | v-maf musculoaponeurotic fibrosarcoma oncogene homolog B (avian) |
| 224991_at | c-Maf-inducing protein |
| 226988_s_at | myosin, heavy polypeptide 14 |
| 244829_at | Hypothetical protein MGC40222 |

TABLE 7

| matched term | description |
| --- | --- |
| 204271_s_at | endothelin receptor type B |
| 244829_at | Hypothetical protein MGC40222 |
| 208073_x_at | tetratricopeptide repeat domain 3 |
| 213037_x_at | staufen, RNA binding protein (*Drosophila*) |
| 200601_at | actinin, alpha 4 |
| 219387_at | KIAA1212 |
| 209168_at | glycoprotein M6B |
| 205051_s_at | v-kit Hardy-Zuckerman 4 feline sarcoma viral oncogene homolog |
| 224991_at | c-Maf-inducing protein |
| 200613_at | adaptor-related protein complex 2, mu 1 subunit |
| 203330_s_at | syntaxin 5A |
| 225009_at | chemokine-like factor superfamily 4 |
| 221485_s_at | UDP-Gal:betaGlcNAc beta 1,4-galactosyltransferase, polypeptide 5 |
| 218255_s_at | fibrosin 1 |
| 227870_at | likely ortholog of mouse neighbor of Punc E11 |
| 226988_s_at | myosin, heavy polypeptide 14 |
| 204086_at | preferentially expressed antigen in melanoma |
| 213146_at | jumonji domain containing 3 |
| 205681_at | BCL2-related protein A1 |
| 213940_s_at | formin binding protein 1 |
| 202478_at | tribbles homolog 2 (*Drosophila*) |
| 226702_at | hypothetical protein LOC129607 |
| 218402_s_at | Hermansky-Pudlak syndrome 4 |
| 227099_s_at | hypothetical LOC387763 |
| 218211_s_at | melanophilin |
| 217738_at | pre-B-cell colony enhancing factor 1 |
| 228488_at | TBC1 domain family, member 16 |
| 215695_s_at | glycogenin 2 |
| 241898_at | Transcribed locus, moderately similar to XP_517655.1 PREDICTED: similar to KIAA0825 protein [Pan troglodytes] |
| 202479_s_at | tribbles homolog 2 (*Drosophila*) |
| 201453_x_at | Ras homolog enriched in brain |

TABLE 7-continued

| matched term | description |
|---|---|
| 228415_at | Adaptor-related protein complex 1, sigma 2 subunit |
| 201908_at | dishevelled, dsh homolog 3 (*Drosophila*) |
| 225600_at | MRNA; cDNA DKFZp779L1068 (from clone DKFZp779L1068) |
| 221951_at | transmembrane protein 80 |
| 203455_s_at | spermidine/spermine N1-acetyltransferase |
| 201603_at | protein phosphatase 1, regulatory (inhibitor) subunit 12A |
| 1558702_at | Testis expressed sequence 10 |
| 204527_at | myosin VA (heavy polypeptide 12, myoxin) |
| 235222_x_at | baculoviral IAP repeat-containing 4 |
| 1560445_x_at | Rho guanine nucleotide exchange factor (GEF) 1 |
| 1556205_at | CDNA FLJ37227 fis, clone BRAMY2000277 |
| 226054_at | bromodomain containing 4 |
| 210198_s_at | proteolipid protein 1 (Pelizaeus-Merzbacher disease, spastic paraplegia 2, uncomplicated) |
| 202370_s_at | core-binding factor, beta subunit |
| 209058_at | endothelial differentiation-related factor 1 |
| 211755_s_at | ATP synthase, H+ transporting, mitochondrial F0 complex, subunit b, isoform 1; ATP synthase, H+ transporting, mitochondrial F0 complex, subunit b, isoform 1 |
| 229713_at | CDNA FLJ13267 fis, clone OVARC1000964 |
| 209514_s_at | RAB27A, member RAS oncogene family |
| 201299_s_at | MOB1, Mps One Binder kinase activator-like 1B (yeast) |
| 211909_x_at | prostaglandin E receptor 3 (subtype EP3); prostaglandin E receptor 3 (subtype EP3) |
| 209234_at | kinesin family member 1B |
| 207622_s_at | ATP-binding cassette, sub-family F (GCN20), member 2 |
| 212421_at | chromosome 22 open reading frame 9 |
| 219636_s_at | armadillo repeat containing 9 |
| 223407_at | chromosome 16 open reading frame 48 |
| 200645_at | GABA(A) receptor-associated protein |
| 242049_s_at | neuroblastoma-amplified protein |
| 230793_at | Leucine rich repeat containing 16 |
| 215409_at | PLSC domain containing protein |
| 202984_s_at | BCL2-associated athanogene 5 |
| 201864_at | GDP dissociation inhibitor 1 |
| 209780_at | putative homeodomain transcription factor 2 |
| 218143_s_at | secretory carrier membrane protein 2 |
| 228919_at | |
| 228095_at | PHD finger protein 14 |
| 213736_at | Cytochrome c oxidase subunit Vb |
| 213655_at | Tyrosine 3-monooxygenase/tryptophan 5-monooxygenase activation protein, epsilon polypeptide |
| 218419_s_at | hypothetical protein MGC3123 |
| 200755_s_at | calumenin |
| 223220_s_at | poly (ADP-ribose) polymerase family, member 9 |
| 237464_at | LAT1-3TM protein 2 |
| 229679_at | FLJ40142 protein |
| | IL-1 RI (Interleukin-1 RI) |
| | EDN2 (endothelin-2) |
| | EFNA5 (ephrin-A5) |
| | IGFBP7 (IGF Binding Protein 7) |
| | HLA-A0202 heavy chain (Human Leukocyte Antigen-A0202 heavy chain) |
| | Activin A (βA subunit) |
| | TNF RII (tumor necrosis factor receptor II) |
| | SPC4 (Subtilisin-Like Proprotein Convertase, PACE4) |
| | CNTF Rα (Ciliary neurotrophic factor receptor α) |

TABLE 8

| Gene | Description |
|---|---|
| 204271_s_at | endothelin receptor type B |
| 244829_at | Hypothetical protein MGC40222 |
| 208073_x_at | tetratricopeptide repeat domain 3 |
| 213037_x_at | staufen, RNA binding protein (*Drosophila*) |
| 200601_at | actinin, alpha 4 |
| 219387_at | KIAA1212 |
| 209168_at | glycoprotein M6B |
| 205051_s_at | v-kit Hardy-Zuckerman 4 feline sarcoma viral oncogene homolog |
| 224991_at | c-Maf-inducing protein |
| 200613_at | adaptor-related protein complex 2, mu 1 subunit |
| 203330_s_at | syntaxin 5A |
| 225009_at | chemokine-like factor superfamily 4 |
| 221485_at | UDP-Gal:betaGlcNAc beta 1,4-galactosyltransferase, polypeptide 5 |
| 218255_s_at | fibrosin 1 |
| 227870_at | likely ortholog of mouse neighbor of Punc E11 |
| 226988_s_at | myosin, heavy polypeptide 14 |
| 204086_at | preferentially expressed antigen in melanoma |
| 213146_at | jumonji domain containing 3 |
| 205681_at | BCL2-related protein A1 |
| 213940_s_at | formin binding protein 1 |

TABLE 10

| Gene | Description |
| --- | --- |
| 221750_at | 3-hydroxy-3-methylglutaryl-Coenzyme A synthase 1 (soluble) |
| 225283_at | arrestin domain containing 4 |
| 212952_at | Calreticulin |
| 226920_at | Casein kinase 1, alpha 1 |
| 201533_at | catenin (cadherin-associated protein), beta 1, 88 kDa |
| 225551_at | chromosome 1 open reading frame 71 |
| 227736_at | chromosome 10 open reading frame 99 |
| 217883_at | chromosome 2 open reading frame 25 |
| 226614_s_at | chromosome 8 open reading frame 13 |
| 214073_at | cortactin |
| 233929_x_at | CXYorf1-related protein |
| 225035_x_at | CXYorf1-related protein; CXYorf1-related protein; CXYorf1-related protein |
| 200953_s_at | cyclin D2 |
| 206595_at | cystatin E/M |
| 224831_at | cytoplasmic polyadenylation element binding protein 4 |
| 201211_s_at | DEAD (Asp-Glu-Ala-Asp) box polypeptide 3, X-linked |
| 200762_at | dihydropyrimidinase-like 2 |
| 219648_at | dilute suppressor |
| 202572_s_at | discs, large (*Drosophila*) homolog-associated protein 4 |
| 200664_s_at | DnaJ (Hsp40) homolog, subfamily B, member 1 |
| 208811_s_at | DnaJ (Hsp40) homolog, subfamily B, member 6 |
| 208370_s_at | Down syndrome critical region gene 1 |
| 214445_at | elongation factor, RNA polymerase II, 2 |
| 214446_at | elongation factor, RNA polymerase II, 2 |
| 201436_at | eukaryotic translation initiation factor 4E |
| 208290_s_at | eukaryotic translation initiation factor 5 |
| 200748_s_at | ferritin, heavy polypeptide 1 |
| 211628_x_at | ferritin, heavy polypeptide pseudogene 1; ferritin, heavy polypeptide pseudogene 1 |
| 205409_at | FOS-like antigen 2 |
| 200959_at | fusion (involved in t(12; 16) in malignant liposarcoma) |
| 201065_s_at | general transcription factor II, i; general transcription factor II, i, pseudogene 1 |
| 218238_at | GTP binding protein 4 |
| 201841_s_at | heat shock 27 kDa protein 1 |
| 225988_at | hect domain and RLD 4 |
| 241683_at | HECT domain containing 1 |
| 201944_at | hexosaminidase B (beta polypeptide) |
| 219976_at | hook homolog 1 (*Drosophila*) |
| 213079_at | hypothetical protein DT1P1A10 |
| 215434_x_at | hypothetical protein FLJ20719; AG1 protein |
| 1569157_s_at | hypothetical protein LOC162993 |
| 227052_at | Hypothetical protein LOC201895 |
| 225065_x_at | hypothetical protein MGC40157 |
| 231733_at | ICEBERG caspase-1 inhibitor |
| 240941_at | Intersectin 2 |
| 208881_x_at | isopentenyl-diphosphate delta isomerase 1 |
| 204615_x_at | isopentenyl-diphosphate delta isomerase 1 |
| 213507_s_at | karyopherin (importin) beta 1 |
| 203068_at | kelch-like 21 (*Drosophila*) |
| 225142_at | KIAA1718 protein |
| 220368_s_at | KIAA2010 |
| 1559226_x_at | late cornified envelope 1E |
| 1559224_at | late cornified envelope 1E |
| 200673_at | lysosomal-associated protein transmembrane 4 alpha |
| 223480_s_at | mitochondrial ribosomal protein L47 |
| 207121_s_at | mitogen-activated protein kinase 6 |
| 214939_x_at | myeloid/lymphoid or mixed-lineage leukemia (trithorax homolog, *Drosophila*); translocated to, 4 |
| 203315_at | NCK adaptor protein 2 |
| 230291_s_at | Nuclear factor I/B |
| 211467_s_at | nuclear factor I/B |
| 213032_at | Nuclear factor I/B |
| 223650_s_at | nuclear receptor binding factor 2 |
| 222878_s_at | OTU domain, ubiquitin aldehyde binding 2 |
| 217608_at | p18 splicing regulatory protein |
| 200907_s_at | palladin |
| 202290_at | PDGFA associated protein 1 |
| 218942_at | phosphatidylinositol-4-phosphate 5-kinase, type II, gamma |
| 225147_at | pleckstrin homology, Sec7 and coiled-coil domains 3 |
| 216515_x_at | prothymosin, alpha (gene sequence 28); hypothetical gene supported by BC013859; hypothetical gene supported by BC013859; BC070480 |
| 200773_x_at | prothymosin, alpha (gene sequence 28); similar to prothymosin alpha; hypothetical gene supported by BC013859; hypothetical gene supported by BC013859; BC070480 |
| 212099_at | ras homolog gene family, member B |
| 212124_at | retinoic acid induced 17 |
| 200022_at | ribosomal protein L18; ribosomal protein L18 |
| 201909_at | ribosomal protein S4, Y-linked 1 |
| 215127_s_at | RNA binding motif, single stranded interacting protein 1 |
| 218143_s_at | secretory carrier membrane protein 2 |

TABLE 10-continued

| Gene | Description |
| --- | --- |
| 205185_at | serine peptidase inhibitor, Kazal type 5 |
| 1554089_s_at | Shwachman-Bodian-Diamond syndrome; Shwachman-Bodian-Diamond syndrome pseudogene |
| 208991_at | signal transducer and activator of transcription 3 (acute-phase response factor) |
| 224573_at | similar to DNA segment, Chr 11, Brigham & Womens Genetics 0434 expressed |
| 242687_at | Similar to RIKEN cDNA 9930021J17 |
| 206675_s_at | SKI-like |
| 1553602_at | small breast epithelial mucin |
| 213879_at | SMT3 suppressor of mif two 3 homolog 2 (yeast) |
| 208738_x_at | SMT3 suppressor of mif two 3 homolog 2 (yeast); similar to SMT3 suppressor of mif two 3 homolog 2 |
| 1556839_s_at | Spectrin, beta, non-erythrocytic 5 |
| 220983_s_at | sprouty homolog 4 (*Drosophila*); sprouty homolog 4 (*Drosophila*) |
| 205966_at | TAF13 RNA polymerase II, TATA box binding protein (TBP)-associated factor, 18 kDa |
| 217733_s_at | thymosin, beta 10 |
| 216438_s_at | thymosin, beta 4, X-linked; thymosin-like 3 |
| 226835_s_at | transaldolase 1; similar to RPE-spondin |
| 224680_at | transmembrane emp24 protein transport domain containing 4 |
| 210987_x_at | tropomyosin 1 (alpha) |
| 211702_s_at | ubiquitin specific peptidase 32; ubiquitin specific peptidase 32 |
| 203798_s_at | visinin-like 1 |
| 210935_s_at | WD repeat domain 1 |
| 224905_at | WD repeat domain 26 |
| 215150_at | YOD1 OTU deubiquinating enzyme 1 homolog (yeast) |
| 227309_at | YOD1 OTU deubiquinating enzyme 1 homolog (yeast) |
| 204180_s_at | zinc finger protein 297B |
| 219163_at | zinc finger protein 562 |
| 220854_at | |
| 224051_at | |
| 224050_s_at | |

TABLE 11

| Gene | Description |
| --- | --- |
| 225519_at | protein phosphatase 4, regulatory subunit 2 |
| 219199_at | AF4/FMR2 family, member 4 |
| 203450_at | PKD2 interactor, golgi and endoplasmic reticulum associated 1 |
| 213729_at | formin binding protein 3 |
| 220748_s_at | zinc finger protein 580 |
| 216480_x_at | Myeloid/lymphoid or mixed-lineage leukemia (trithorax homolog, *Drosophila*); translocated to, 10 |
| 200043_at | enhancer of rudimentary homolog (*Drosophila*); enhancer of rudimentary homolog (*Drosophila*) |
| 211075_s_at | CD47 antigen (Rh-related antigen, integrin-associated signal transducer); CD47 antigen (Rh-related antigen, integrin-associated signal transducer) |
| 1555945_s_at | chromosome 9 open reading frame 10 |
| 212295_s_at | solute carrier family 7 (cationic amino acid transporter, y+ system), member 1 |
| 212687_at | LIM and senescent cell antigen-like domains 1 |
| 224714_at | MKI67 (FHA domain) interacting nucleolar phosphoprotein |
| 218768_at | nucleoporin 107 kDa |
| 228196_s_at | La ribonucleoprotein domain family, member 5 |
| 217836_s_at | YY1 associated protein 1 |
| 212620_at | zinc finger protein 609 |
| 226845_s_at | myeloma overexpressed 2 |
| 200747_s_at | nuclear mitotic apparatus protein 1 |
| 242304_at | within bgcn homolog (*Drosophila*) |
| 204767_s_at | flap structure-specific endonuclease 1 |
| 217869_at | hydroxysteroid (17-beta) dehydrogenase 12 |
| 222729_at | F-box and WD-40 domain protein 7 (archipelago homolog, *Drosophila*) |
| 201776_s_at | KIAA0494 |
| 1552658_a_at | neuron navigator 3 |
| 1555972_s_at | F-box protein 28 |
| 216242_x_at | DNA directed RNA polymerase II polypeptide J-related gene |
| 231505_s_at | Sideroflexin 4 |
| 228738_at | hypothetical protein MGC25181 |
| 228942_s_at | DAB2 interacting protein |
| 208959_s_at | thioredoxin domain containing 4 (endoplasmic reticulum) |
| 223407_at | chromosome 16 open reading frame 48 |
| 1555278_a_at | cytoskeleton associated protein 5 |
| 219375_at | choline/ethanolamine phosphotransferase 1 |
| 208728_s_at | cell division cycle 42 (GTP binding protein, 25 kDa) |
| 50376_at | zinc finger protein 444 |
| 243108_at | RAN binding protein 9 |
| 212884_x_at | Apolipoprotein E |

TABLE 11-continued

| Gene | Description |
| --- | --- |
| 65630_at | transmembrane protein 80 |
| 214953_s_at | amyloid beta (A4) precursor protein (peptidase nexin-II, Alzheimer disease) |
| 223946_at | cofactor required for Sp1 transcriptional activation, subunit 3, 130 kDa |
| 232926_x_at | ankyrin repeat domain 19 |
| 203597_s_at | WW domain binding protein 4 (formin binding protein 21) |
| 223601_at | olfactomedin 2 |
| 212365_at | myosin IB |
| 203297_s_at | Jumonji, AT rich interactive domain 2 |
| 231019_x_at | Serine/threonine kinase 11 (Peutz-Jeghers syndrome) |
| 201291_s_at | topoisomerase (DNA) II alpha 170 kDa |
| 211846_s_at | poliovirus receptor-related 1 (herpesvirus entry mediator C; nectin) |
| 226843_s_at | PAP associated domain containing 5 |
| 225243_s_at | sarcolemma associated protein |
| 236651_at | kalirin, RhoGEF kinase |
| 214792_x_at | vesicle-associated membrane protein 2 (synaptobrevin 2) |
| 228922_at | Src homology 2 domain containing F |
| 225537_at | trafficking protein particle complex 6B |
| 46665_at | sema domain, immunoglobulin domain (Ig), transmembrane domain (TM) and short cytoplasmic domain, (semaphorin) 4C |
| 209702_at | fatso |
| 203358_s_at | enhancer of zeste homolog 2 (*Drosophila*) |
| 211310_at | enhancer of zeste homolog 1 (*Drosophila*) |
| 242767_at | LIM and cysteine-rich domains 1 |
| 1555575_a_at | KDEL (Lys-Asp-Glu-Leu) endoplasmic reticulum protein retention receptor 1 |
| 223151_at | DCN1, defective in cullin neddylation 1, domain containing 5 (*S. cerevisiae*) |
| 204170_s_at | CDC28 protein kinase regulatory subunit 2 |
| 229420_at | Luminal binding protein 1 (BiP-1) (BP1) |
| 202355_s_at | general transcription factor IIF, polypeptide 1, 74 kDa |
| 206061_s_at | Dicer1, Dcr-1 homolog (*Drosophila*) |
| 224597_at | Transcribed locus, strongly similar to XP_523650.1 PREDICTED: similar to keratin 17 [*Pan troglodytes*] |
| 217739_s_at | pre-B-cell colony enhancing factor 1 |
| 218943_s_at | DEAD (Asp-Glu-Ala-Asp) box polypeptide 58 |
| 211087_x_at | mitogen-activated protein kinase 14; mitogen-activated protein kinase 14 |
| 220193_at | chromosome 1 open reading frame 113 |
| 229410_at | progestagen-associated endometrial protein (placental protein 14, pregnancy-associated endometrial alpha-2-globulin, alpha uterine protein) |
| 221844_x_at | CDNA clone IMAGE: 6208446 |
| 227683_x_at | Nudix (nucleoside diphosphate linked moiety X)-type motif 4 pseudogene 2 |
| 233621_s_at | Rho guanine nucleotide exchange factor (GEF) 12 |
| 214270_s_at | microtubule-associated protein, RP/EB family, member 3 |
| 217762_s_at | RAB31, member RAS oncogene family |
| 231271_x_at | HSCARG protein |
| 227330_x_at | similar to hypothetical protein MGC27019 |
| 209773_s_at | ribonucleotide reductase M2 polypeptide |
| 225227_at | SKI-like |
| 218428_s_at | REV1-like (yeast) |
| 201556_s_at | vesicle-associated membrane protein 2 (synaptobrevin 2) |

TABLE 12

| Gene | Description |
| --- | --- |
| 1552477_a_at | interferon regulatory factor 6 |
| 228707_at | claudin 23 |
| 206427_s_at | melan-A |
| 218196_at | osteopetrosis associated transmembrane protein 1 |
| 219142_at | RAS-like, family 11, member B |
| 200601_at | actinin, alpha 4 |
| 226483_at | transmembrane protein 68 |
| 243568_at | Glycine-rich protein (GRP3S) |
| 212382_at | Transcription factor 4 |
| 218417_s_at | hypothetical protein FLJ20489 |
| 208905_at | cytochrome c, somatic |
| 203753_at | transcription factor 4 |
| 244535_at | Forkhead box P1 |
| 222243_s_at | transducer of ERBB2, 2 |
| 205174_s_at | glutaminyl-peptide cyclotransferase (glutaminyl cyclase) |
| 231851_at | hypothetical protein FLJ10770 |
| 200961_at | selenophosphate synthetase 2 |
| 210880_s_at | embryonal Fyn-associated substrate |
| 230986_at | Kruppel-like factor 8 |
| 229689_s_at | Discs, large homolog 5 (*Drosophila*) |
| 204319_s_at | regulator of G-protein signalling 10 |
| 219842_at | ADP-ribosylation factor related protein 2 |
| 224560_at | TIMP metallopeptidase inhibitor 2 |
| 208758_at | 5-aminoimidazole-4-carboxamide ribonucleotide formyltransferase/IMP cyclohydrolase |
| 238662_at | similar to RIKEN cDNA 5730421E18 gene |
| 214000_s_at | Regulator of G-protein signalling 10 |
| 1559360_at | Nuclear RNA-binding protein, putative |
| 205694_at | tyrosinase-related protein 1 |
| 231579_s_at | TIMP metallopeptidase inhibitor 2 |
| 238967_at | Claudin 1 |
| 222146_s_at | transcription factor 4 |
| 230748_at | solute carrier family 16 (monocarboxylic acid transporters), member 6; similar to solute carrier family 16, member 6; monocarboxylate transporter 6 |

TABLE 13

| gene | description | Sample | | | | | |
|---|---|---|---|---|---|---|---|
| | | Melanoma DT357-M | Melanoma DT330-M | Melanoma DT359-M | Melanoma DT419-M | Melanoma DT407-M | Melanoma DT412-M |
| 244829_at | C6orf218 | 114.5632 | 19.56224 | 0.594604 | 7.412704 | 53.81737 | 0.456916 |
| 204271_s_at | EDNRB | 225.972 | 151.1671 | 18.89588 | 16.67945 | 754.8258 | 17.26765 |
| 200601_at | ACTN4 | 30.90996 | 23.10287 | 10.05611 | 1.484524 | 60.96883 | 5.241574 |
| 226988_s_at | MYH14 | 0.192109 | 0.343885 | 0.032804 | 0.140632 | 0.009486 | 0.554785 |
| 202478_at | TRIB2 | 99.73307 | 75.58353 | 28.84001 | 12.72858 | 464.6498 | 15.67072 |
| 1557292_a_at | MCOLN3 | 28.05138 | 8.282119 | 5.464161 | 4.084049 | 64.89341 | 3.555371 |
| 224991_at | CMIP | 0.615572 | 0.208772 | 0.214641 | 0.205898 | 0.115023 | 1.741101 |
| 1555505_a_at | TYR | 21.25897 | 23.26356 | 9.849155 | 0.952638 | 150.1229 | 5.426417 |
| 201908_at | DVL3 | 0.339151 | 0.088388 | 0.239816 | 8.111676 | 5.502167 | 4.924578 |
| 222670_s_at | MAFB | 0.070316 | 0.069348 | 0.005263 | 0.00146 | 0.532185 | 0.164938 |
| 201605_x_at | CNN2 | 150.1229 | 58.48521 | 15.13692 | 13.54793 | 324.0337 | 17.5087 |
| 213146_at | JMJD3 | 0.005048 | 0.003879 | 0.02683 | 0.00198 | 0.009486 | 0.001211 |
| 201603_at | PPP1R12A | 2.188587 | 4.69134 | 0.817902 | 0.281265 | 7.361501 | 0.05954 |
| 209953_s_at | CDC37 | 12.72858 | 34.05985 | 4.756828 | 0.615572 | 13.73705 | 2.732081 |
| 201245_s_at | OTUB1 | 9.063071 | 6.233317 | 5.464161 | 1.905276 | 10.77787 | 1.580083 |
| 208073_x_at | TTC3 | 15.34823 | 12.72858 | 8.168097 | 8.224911 | 36.50444 | 6.916298 |
| 200958_s_at | SDCBP | 3.07375 | 1.197479 | 0.336808 | 0.078021 | 6.916298 | 0.065154 |
| 205051_s_at | KIT | 86.82268 | 54.1917 | 2.713209 | 8.815241 | 55.71524 | 4.055838 |
| 200819_s_at | RPS15 | 1584.707 | 1640.591 | 491.1432 | 182.2784 | 3795.305 | 377.4129 |

| gene | description | Sample | | | |
|---|---|---|---|---|---|
| | | Melanoma DT403-M | Melanoma DT406-M | Melanoma DT356-M | Melanoma DT405-M |
| 244829_at | C6orf218 | 16.44982 | 10884.59 | 17.14838 | 2797.65 |
| 204271_s_at | EDNRB | 81.00842 | 45073.75 | 63.11889 | 11828.67 |
| 200601_at | ACTN4 | 38.85424 | 4269.94 | 9.000468 | 13682.08 |
| 226988_s_at | MYH14 | 0.004613 | 1 | 0.164938 | 1045.516 |
| 202478_at | TRIB2 | 19.42712 | 1 | 24.93327 | 14972.21 |
| 1557292_a_at | MCOLN3 | 3.24901 | 1067.485 | 4.756828 | 1082.386 |
| 224991_at | CMIP | 1.148698 | 1 | 0.122428 | 1351.176 |
| 1555505_a_at | TYR | 2.928171 | 4870.992 | 2.732081 | 3468.269 |
| 201908_at | DVL3 | 1.292353 | 32.89964 | 4.169863 | 7281.399 |
| 222670_s_at | MAFB | 0.145592 | 1 | 0.000816 | 103.9683 |
| 201605_x_at | CNN2 | 28.44297 | 22226.61 | 32.67239 | 46340.95 |
| 213146_at | JMJD3 | 0.018326 | 37.01402 | 0.078563 | 50.91433 |
| 201603_at | PPP1R12A | 0.926588 | 481.0356 | 0.103665 | 205.0739 |
| 209953_s_at | CDC37 | 21.70567 | 1226.218 | 7.310652 | 9410.137 |
| 201245_s_at | OTUB1 | 11.87619 | 3691.522 | 1.840375 | 4182.066 |
| 208073_x_at | TTC3 | 7.674113 | 4973.342 | 1.741101 | 4299.64 |
| 200958_s_at | SDCBP | 0.389582 | 261.3791 | 0.5 | 247.2797 |
| 205051_s_at | KIT | 0.435275 | 3082.745 | 12.81712 | 689.7836 |
| 200819_s_at | RPS15 | 1884.544 | 389158.9 | 484.3815 | 668236.8 |

TABLE 14

| gene | description | Sample | | | | | |
|---|---|---|---|---|---|---|---|
| | | Nevus DF543 | Nevus DF544 | Nevus DT343 | Nevus DT342 | Nevus DT344 | Nevus DT345 |
| 244829_at | C6orf218 | 0.094732 | 0.80107 | 0.297302 | 0.00849 | 0.000905 | 1 |
| 204271_s_at | EDNRB | 393.44 | 16 | 401.7071 | 0.135842 | 0.010598 | 225.972 |
| 200601_at | ACTN4 | 0.289172 | 44.3235 | 5712.87 | 65.79928 | 12.21007 | 14462.21 |
| 226988_s_at | MYH14 | 0.094732 | 1.404445 | 430.539 | 48.50293 | 0.109576 | 2304.12 |
| 202478_at | TRIB2 | 23.26356 | 6.868523 | 797.8645 | 0.00849 | 0.005601 | 1 |
| 1557292_a_at | MCOLN3 | 0.25 | 0.882703 | 0.297302 | 0.00849 | 0.000905 | 1 |
| 224991_at | CMIP | 3.944931 | 0.664343 | 132.5139 | 7.727491 | 0.61132 | 1686.714 |
| 1555505_a_at | TYR | 2.297397 | 9.189587 | 0.297302 | 0.00849 | 0.010167 | 63.55792 |
| 201908_at | DVL3 | 0.094732 | 2.219139 | 139.1021 | 0.993092 | 0.248273 | 404.5012 |
| 222670_s_at | MAFB | 0.233258 | 1.006956 | 41.93259 | 1.879045 | 0.112656 | 418.7659 |
| 201605_x_at | CNN2 | 41.93259 | 183.5463 | 21027.65 | 855.13 | 50.91433 | 3615.551 |
| 213146_at | JMJD3 | 0.094732 | 0.496546 | 4.69134 | 0.07911 | 0.000905 | 1.580083 |
| 201603_at | PPP1R12A | 0.094732 | 3.680751 | 85.03589 | 19.02731 | 0.543367 | 16.22335 |
| 209953_s_at | CDC37 | 1.918528 | 8.815241 | 699.4126 | 34.5353 | 0.959264 | 2957.167 |
| 201245_s_at | OTUB1 | 0.094732 | 11.87619 | 1663.493 | 45.25483 | 11.08678 | 9026.807 |
| 208073_x_at | TTC3 | 0.882703 | 58.08123 | 1478.583 | 12.295 | 0.132127 | 6472.018 |
| 200958_s_at | SDCBP | 0.094732 | 0.188156 | 3.317278 | 0.986233 | 0.016402 | 7.568461 |
| 205051_s_at | KIT | 0.094732 | 0.239816 | 34.5353 | 2.602684 | 0.011203 | 1 |
| 200819_s_at | RPS15 | 13124.73 | 4299.64 | 205674 | 11346.82 | 584.071 | 736333.6 |

TABLE 14-continued

| gene | description | Nevus DT427 | Nevus DT337 | Nevus DT340 | Nevus DT338 |
|---|---|---|---|---|---|
| 244829_at | C6orf218 | 0.550953 | 0.939523 | 0.001236 | 0.479632 |
| 204271_s_at | EDNRB | 1136.199 | 0.20733 | 0.001236 | 393.44 |
| 200601_at | ACTN4 | 3350.127 | 127.1158 | 64.44516 | 3236.009 |
| 226988_s_at | MYH14 | 867.0672 | 2.907945 | 1.265757 | 410.1478 |
| 202478_at | TRIB2 | 8422.308 | 4.287094 | 3.434262 | 12.46663 |
| 1557292_a_at | MCOLN3 | 116.9704 | 14.12325 | 0.001236 | 0.479632 |
| 224991_at | CMIP | 369.6459 | 1.021012 | 1.918528 | 433.5336 |
| 1555505_a_at | TYR | 10.33882 | 1.94531 | 0.001236 | 39.67065 |
| 201908_at | DVL3 | 1097.496 | 6.588728 | 1.580083 | 9.38268 |
| 222670_s_at | MAFB | 12.64066 | 0.946058 | 0.002577 | 51.98415 |
| 201605_x_at | CNN2 | 10015.87 | 181.0193 | 58.48521 | 3821.703 |
| 213146_at | JMJD3 | 0.550953 | 0.628507 | 0.001236 | 0.479632 |
| 201603_at | PPP1R12A | 202.2506 | 3.160165 | 0.008373 | 942.2722 |
| 209953_s_at | CDC37 | 94.35323 | 60.54769 | 7.110741 | 3929.146 |
| 201245_s_at | OTUB1 | 10297.45 | 47.50475 | 9.063071 | 2179.83 |
| 208073_x_at | TTC3 | 1937.526 | 50.56264 | 0.314253 | 2836.704 |
| 200958_s_at | SDCBP | 0.550953 | 0.346277 | 0.001236 | 1.049717 |
| 205051_s_at | KIT | 37.01402 | 1.22264 | 0.001236 | 0.479632 |
| 200819_s_at | RPS15 | 137588.5 | 7967.989 | 600.4915 | 269513.9 |

TABLE 15

| Gene | Lentigo Maligna Mean expression | Solar lentigo Mean expression | (Lentigo Maligna)/(Solar Lentigo) fold change | Description |
|---|---|---|---|---|
| 200961_at | 455.88 | 223.03 | 2.04 | selenophosphate synthetase 2 |
| 200782_at | 379.88 | 70.68 | 5.37 | annexin A5 |
| 206427_s_at | 1899.38 | 165.82 | 11.45 | melan-A |
| 217998_at | 416.81 | 99.94 | 4.17 | pleckstrin homology-like domain, family A, member 1 |
| 226602_s_at | 117.73 | 209.24 | 0.56 | breakpoint cluster region; similar to breakpoint cluster region isoform 1 |
| 240366_at | 70.62 | 6.65 | 10.62 | Lipoma HMGIC fusion partner-like 3 |
| 208325_s_at | 760.50 | 1233.35 | 0.62 | A kinase (PRKA) anchor protein 13 |
| 225202_at | 196.73 | 24.59 | 8.00 | Rho-related BTB domain containing 3 |
| 225946_at | 46.81 | 5.74 | 8.16 | Ras association (RalGDS/AF-6) domain family 8 |
| 1553603_s_at | 37.15 | 61.18 | 0.61 | ADP-ribosylation factor-like 6 interacting protein 2 |
| 220625_s_at | 125.23 | 75.62 | 1.66 | E74-like factor 5 (ets domain transcription factor) |
| 229982_at | 28.00 | 20.79 | 1.35 | hypothetical protein FLJ21924 |
| 1552283_s_at | 17.50 | 35.56 | 0.49 | zinc finger, DHHC-type containing 11 |
| 200723_s_at | 203.23 | 113.68 | 1.79 | membrane component, chromosome 11, surface marker 1 |
| 209174_s_at | 57.35 | 106.44 | 0.54 | FLJ20259 protein |
| 233599_at | 244.31 | 403.97 | 0.60 | Chromosome 9 open reading frame 3 |
| 201739_at | 4791.23 | 2597.32 | 1.84 | serum/glucocorticoid regulated kinase |
| 209392_at | 403.54 | 12.79 | 31.54 | ectonucleotide pyrophosphatase/phosphodiesterase 2 (autotaxin) |
| 209487_at | 185.54 | 46.44 | 4.00 | RNA binding protein with multiple splicing |
| 221653_x_at | 882.08 | 458.24 | 1.92 | apolipoprotein L, 2 |
| 209185_s_at | 349.73 | 118.85 | 2.94 | insulin receptor substrate 2 |
| 222809_x_at | 227.73 | 336.12 | 0.68 | chromosome 14 open reading frame 65 |
| 223363_at | 150.69 | 280.06 | 0.54 | hypothetical protein MGC10911 |

TABLE 15-continued

| Gene | Lentigo Maligna Mean expression | Solar lentigo Mean expression | (Lentigo Maligna)/(Solar Lentigo) fold change | Description |
|---|---|---|---|---|
| 208456_s_at | 56.19 | 122.65 | 0.46 | related RAS viral (r-ras) oncogene homolog 2 |
| 221449_s_at | 69.81 | 41.09 | 1.70 | T-cell immunomodulatory protein; T-cell immunomodulatory protein |
| 215268_at | 24.12 | 46.74 | 0.52 | KIAA0754 protein |
| 217188_s_at | 146.88 | 397.50 | 0.37 | chromosome 14 open reading frame 1 |
| 236972_at | 302.00 | 27.09 | 11.15 | tripartite motif-containing 63 |

TABLE 16

| gene | solar lentigo DF529-S | solar lentigo DF530-S | solar lentigo DF633-S | solar lentigo DF634-S | solar lentigo DF635-S | solar lentigo DF636-S | solar lentigo DF637-S | solar lentigo DF638-S | solar lentigo DF639-S | solar lentigo DF640-S | solar lentigo DF641-S | solar lentigo DF642-S |
|---|---|---|---|---|---|---|---|---|---|---|---|---|
| 200961_at | 106 | 217 | 101 | 38 | 161 | 221 | 160 | 336 | 304 | 256 | 63 | 210 |
| 200782_at | 122 | 21 | 45 | 8 | 70 | 27 | 104 | 195 | 200 | 63 | 101 | 114 |
| 206427_s_at | 58 | 28 | 92 | 19 | 132 | 29 | 92 | 72 | 1708 | 12 | 92 | 190 |
| 217998_at | 106 | 67 | 180 | 18 | 86 | 76 | 181 | 95 | 238 | 169 | 7 | 8 |
| 226602_s_at | 654 | 97 | 144 | 691 | 129 | 265 | 109 | 194 | 137 | 277 | 194 | 130 |
| 240366_at | 6 | 6 | 7 | 6 | 5 | 6 | 27 | 6 | 6 | 6 | 6 | 6 |
| 225202_at | 5 | 6 | 22 | 9 | 84 | 14 | 13 | 14 | 35 | 8 | 21 | 5 |
| 225946_at | 5 | 5 | 5 | 5 | 6 | 5 | 5 | 5 | 13 | 6 | 5 | 5 |
| 1553603_s_at | 33 | 70 | 60 | 5 | 67 | 59 | 40 | 26 | 54 | 127 | 21 | 43 |
| 220625_s_at | 37 | 35 | 6 | 6 | 17 | 173 | 55 | 29 | 42 | 5 | 13 | 5 |
| 229982_at | 58 | 17 | 25 | 9 | 15 | 13 | 22 | 17 | 9 | 33 | 16 | 12 |
| 1552283_s_at | 14 | 31 | 38 | 14 | 49 | 10 | 14 | 33 | 19 | 23 | 41 | 13 |
| 200723_s_at | 94 | 159 | 201 | 22 | 263 | 94 | 299 | 157 | 95 | 217 | 75 | 93 |
| 209174_s_at | 118 | 143 | 64 | 25 | 107 | 89 | 103 | 236 | 46 | 256 | 38 | 110 |
| 233599_at | 89 | 322 | 294 | 116 | 433 | 380 | 295 | 370 | 306 | 241 | 252 | 294 |
| 201739_at | 1421 | 958 | 3724 | 618 | 2023 | 2741 | 3098 | 4062 | 3856 | 1907 | 1530 | 1569 |
| 209392_at | 7 | 44 | 6 | 19 | 10 | 9 | 9 | 10 | 47 | 6 | 17 | 17 |
| 209487_at | 6 | 403 | 9 | 6 | 16 | 6 | 24 | 163 | 94 | 5 | 5 | 23 |
| 221653_x_at | 88 | 379 | 298 | 349 | 396 | 575 | 322 | 372 | 3571 | 319 | 1159 | 1349 |
| 209185_s_at | 307 | 365 | 182 | 58 | 86 | 140 | 195 | 127 | 44 | 97 | 165 | 130 |
| 222809_x_at | 646 | 253 | 322 | 6 | 358 | 262 | 319 | 316 | 490 | 277 | 381 | 654 |
| 223363_at | 206 | 112 | 192 | 102 | 324 | 318 | 343 | 323 | 185 | 694 | 706 | 860 |
| 208456_s_at | 322 | 22 | 30 | 34 | 83 | 22 | 125 | 71 | 129 | 125 | 43 | 122 |
| 221449_s_at | 35 | 26 | 73 | 7 | 69 | 31 | 51 | 37 | 8 | 52 | 66 | 49 |
| 215268_at | 11 | 12 | 43 | 9 | 30 | 8 | 22 | 8 | 44 | 73 | 11 | 51 |
| 217188_s_at | 1276 | 36 | 545 | 12 | 519 | 479 | 281 | 801 | 209 | 500 | 99 | 457 |
| 236972_at | 6 | 6 | 6 | 11 | 6 | 6 | 6 | 6 | 12 | 6 | 6 | 13 |

TABLE 17

| gene | solar lentigo DF643-S | solar lentigo DT024-S | solar lentigo DT055-S | solar lentigo DT069-S | solar lentigo DT079-S | solar lentigo DT123-S | solar lentigo DT146-S | solar lentigo DT187-S | solar lentigo DT306-S | solar lentigo DT365-S | solar lentigo DT367-S | solar lentigo DT368-S |
|---|---|---|---|---|---|---|---|---|---|---|---|---|
| 200961_at | 223 | 149 | 159 | 8 | 113 | 202 | 2155 | 152 | 177 | 56 | 76 | 180 |
| 200782_at | 17 | 79 | 6 | 84 | 136 | 8 | 5 | 95 | 65 | 34 | 29 | 11 |
| 206427_s_at | 9 | 444 | 5 | 13 | 29 | 7 | 11 | 500 | 672 | 5 | 6 | 20 |
| 217998_at | 15 | 178 | 8 | 104 | 181 | 64 | 6 | 62 | 31 | 205 | 42 | 16 |
| 226602_s_at | 286 | 212 | 327 | 97 | 368 | 456 | 57 | 84 | 154 | 301 | 50 | 24 |
| 240366_at | 6 | 6 | 6 | 7 | 6 | 6 | 6 | 6 | 6 | 6 | 6 | 6 |
| 208325_s_at | 1565 | 923 | 877 | 30 | 973 | 1508 | 1981 | 1326 | 1289 | 863 | 354 | 3194 |
| 225202_at | 49 | 40 | 8 | 9 | 21 | 101 | 8 | 47 | 22 | 12 | 31 | 8 |
| 225946_at | 5 | 6 | 5 | 6 | 6 | 5 | 5 | 5 | 9 | 5 | 5 | 6 |
| 1553603_s_at | 54 | 72 | 76 | 21 | 84 | 84 | 44 | 71 | 80 | 71 | 100 | 168 |
| 220625_s_at | 118 | 5 | 6 | 5 | 5 | 14 | 865 | 17 | 5 | 5 | 6 | 6 |
| 229982_at | 8 | 8 | 13 | 8 | 33 | 6 | 16 | 18 | 22 | 13 | 13 | 18 |
| 1552283_s_at | 10 | 23 | 9 | 11 | 12 | 9 | 13 | 155 | 122 | 10 | 13 | 67 |
| 200723_s_at | 32 | 21 | 21 | 7 | 179 | 50 | 220 | 171 | 93 | 92 | 17 | 83 |
| 209174_s_at | 172 | 38 | 48 | 85 | 256 | 115 | 110 | 147 | 109 | 141 | 27 | 96 |
| 233599_at | 594 | 125 | 489 | 243 | 695 | 36 | 931 | 591 | 623 | 1648 | 346 | 1044 |
| 201739_at | 3963 | 4104 | 8062 | 2767 | 2729 | 2760 | 378 | 2524 | 1236 | 3566 | 2237 | 785 |
| 209392_at | 8 | 8 | 7 | 10 | 10 | 7 | 7 | 35 | 14 | 7 | 9 | 7 |

TABLE 17-continued

| gene | solar lentigo DF643-S | solar lentigo DT024-S | solar lentigo DT055-S | solar lentigo DT069-S | solar lentigo DT079-S | solar lentigo DT123-S | solar lentigo DT146-S | solar lentigo DT187-S | solar lentigo DT306-S | solar lentigo DT365-S | solar lentigo DT367-S | solar lentigo DT368-S |
|---|---|---|---|---|---|---|---|---|---|---|---|---|
| 209487_at | 39 | 139 | 6 | 7 | 84 | 12 | 201 | 44 | 8 | 19 | 6 | 6 |
| 221653_x_at | 330 | 198 | 139 | 243 | 341 | 331 | 301 | 382 | 511 | 137 | 564 | 306 |
| 209185_s_at | 53 | 83 | 133 | 7 | 201 | 137 | 170 | 91 | 84 | 78 | 32 | 86 |
| 222809_x_at | 323 | 478 | 622 | 65 | 190 | 729 | 938 | 438 | 211 | 284 | 180 | 249 |
| 223363_at | 196 | 291 | 109 | 85 | 163 | 290 | 331 | 165 | 279 | 161 | 145 | 234 |
| 208456_s_at | 43 | 211 | 509 | 472 | 81 | 24 | 298 | 32 | 69 | 19 | 75 | 231 |
| 221449_s_at | 121 | 78 | 31 | 6 | 39 | 10 | 46 | 74 | 56 | 60 | 6 | 31 |
| 215268_at | 36 | 19 | 18 | 8 | 102 | 119 | 104 | 133 | 24 | 14 | 108 | 27 |
| 217188_s_at | 692 | 225 | 228 | 11 | 480 | 1467 | 195 | 178 | 306 | 423 | 29 | 189 |
| 236972_at | 6 | 34 | 6 | 17 | 5 | 6 | 6 | 6 | 6 | 6 | 7 | 6 |

TABLE 18

| gene | solar lentigo DT369-S | solar lentigo DT370-S | solar lentigo DT371-S | solar lentigo DT372-S | solar lentigo DT373-S | solar lentigo DT409-S | solar lentigo DT414-S | solar lentigo DT422-S | solar lentigo DT459-S | solar lentigo DT460-S |
|---|---|---|---|---|---|---|---|---|---|---|
| 200961_at | 55 | 39 | 38 | 124 | 262 | 37 | 881 | 60 | 128 | 136 |
| 200782_at | 139 | 50 | 248 | 17 | 73 | 48 | 117 | 11 | 53 | 8 |
| 206427_s_at | 9 | 92 | 20 | 7 | 625 | 9 | 585 | 19 | 7 | 20 |
| 217998_at | 496 | 34 | 123 | 58 | 140 | 71 | 22 | 31 | 98 | 182 |
| 226602_s_at | 123 | 46 | 107 | 349 | 95 | 97 | 184 | 440 | 119 | 117 |
| 240366_at | 6 | 6 | 6 | 6 | 6 | 6 | 6 | 6 | 6 | 6 |
| 208325_s_at | 1373 | 60 | 557 | 201 | 1500 | 2266 | 1545 | 1500 | 2099 | 839 |
| 225202_at | 20 | 12 | 9 | 122 | 9 | 8 | 5 | 11 | 40 | 8 |
| 225946_at | 6 | 6 | 6 | 6 | 6 | 5 | 5 | 6 | 6 | 5 |
| 1553603_s_at | 57 | 101 | 22 | 34 | 47 | 33 | 47 | 39 | 102 | 68 |
| 220625_s_at | 5 | 6 | 5 | 6 | 6 | 5 | 974 | 6 | 11 | 67 |
| 229982_at | 58 | 6 | 13 | 13 | 13 | 8 | 13 | 31 | 117 | 13 |
| 1552283_s_at | 65 | 12 | 18 | 9 | 15 | 6 | 87 | 138 | 25 | 81 |
| 200723_s_at | 95 | 97 | 11 | 41 | 97 | 77 | 253 | 7 | 103 | 329 |
| 209174_s_at | 177 | 31 | 140 | 123 | 28 | 163 | 134 | 13 | 47 | 84 |
| 233599_at | 453 | 300 | 195 | 152 | 58 | 166 | 802 | 300 | 279 | 273 |
| 201739_at | 2723 | 3494 | 2757 | 850 | 3680 | 3553 | 721 | 897 | 3544 | 3472 |
| 209392_at | 6 | 9 | 31 | 7 | 7 | 7 | 12 | 10 | 9 | 7 |
| 209487_at | 15 | 6 | 7 | 6 | 6 | 6 | 166 | 7 | 23 | 6 |
| 221653_x_at | 237 | 204 | 353 | 362 | 354 | 249 | 229 | 108 | 171 | 353 |
| 209185_s_at | 100 | 15 | 10 | 82 | 94 | 6 | 496 | 13 | 101 | 73 |
| 222809_x_at | 167 | 215 | 248 | 121 | 408 | 209 | 336 | 138 | 226 | 369 |
| 223363_at | 121 | 145 | 83 | 121 | 984 | 182 | 227 | 150 | 466 | 229 |
| 208456_s_at | 168 | 41 | 216 | 39 | 230 | 22 | 77 | 23 | 28 | 134 |
| 221449_s_at | 34 | 6 | 5 | 10 | 7 | 160 | 18 | 7 | 27 | 61 |
| 215268_at | 88 | 9 | 11 | 52 | 55 | 13 | 24 | 9 | 254 | 40 |
| 217188_s_at | 647 | 119 | 93 | 79 | 122 | 694 | 269 | 111 | 834 | 910 |
| 236972_at | 6 | 36 | 619 | 8 | 11 | 6 | 6 | 17 | 5 | 6 |

TABLE 19

| gene | lentigo maligna DF569-LM | lentigo maligna DF557-LM | lentigo maligna DF579-LM | lentigo maligna DF580-LM | lentigo maligna DF582-LM | lentigo maligna DF596-LM | lentigo maligna DF623-LM | lentigo maligna DF624-LM | lentigo maligna DF625-LM | lentigo maligna DF626-LM | lentigo maligna DF627-LM |
|---|---|---|---|---|---|---|---|---|---|---|---|
| 200961_at | 847 | 567 | 158 | 531 | 234 | 359 | 357 | 330 | 347 | 518 | 1667 |
| 200782_at | 154 | 500 | 157 | 193 | 764 | 1310 | 331 | 27 | 157 | 161 | 16 |
| 206427_s_at | 1833 | 2805 | 95 | 1327 | 2219 | 6320 | 3253 | 49 | 274 | 193 | 121 |
| 217998_at | 185 | 1245 | 726 | 88 | 907 | 773 | 789 | 182 | 340 | 114 | 10 |
| 226602_s_at | 49 | 47 | 59 | 51 | 71 | 36 | 50 | 51 | 137 | 91 | 579 |
| 240366_at | 139 | 251 | 6 | 43 | 122 | 35 | 15 | 6 | 12 | 25 | 6 |
| 208325_s_at | 20 | 1362 | 725 | 408 | 882 | 430 | 568 | 1583 | 1867 | 1460 | 699 |
| 225202_at | 25 | 16 | 44 | 312 | 237 | 1183 | 170 | 33 | 26 | 83 | 8 |
| 225946_at | 48 | 57 | 9 | 76 | 12 | 7 | 35 | 5 | 5 | 6 | 28 |
| 1553603_s_at | 8 | 21 | 43 | 67 | 45 | 21 | 37 | 38 | 50 | 23 | 10 |
| 220625_s_at | 5 | 5 | 5 | 288 | 29 | 5 | 132 | 154 | 126 | 206 | 1427 |
| 229982_at | 8 | 8 | 19 | 8 | 28 | 21 | 13 | 44 | 35 | 28 | 93 |
| 1552283_s_at | 11 | 14 | 12 | 16 | 5 | 13 | 68 | 10 | 35 | 13 | 13 |
| 200723_s_at | 159 | 480 | 276 | 85 | 369 | 112 | 349 | 90 | 319 | 242 | 134 |
| 209174_s_at | 135 | 24 | 48 | 68 | 87 | 130 | 40 | 58 | 85 | 110 | 60 |
| 233599_at | 158 | 60 | 524 | 126 | 283 | 385 | 298 | 183 | 228 | 276 | 165 |
| 201739_at | 6073 | 10285 | 3008 | 5935 | 4757 | 3159 | 3792 | 3462 | 3128 | 2916 | 826 |

TABLE 19-continued

| gene | lentigo maligna DF569-LM | lentigo maligna DF557-LM | lentigo maligna DF579-LM | lentigo maligna DF580-LM | lentigo maligna DF582-LM | lentigo maligna DF596-LM | lentigo maligna DF623-LM | lentigo maligna DF624-LM | lentigo maligna DF625-LM | lentigo maligna DF626-LM | lentigo maligna DF627-LM |
|---|---|---|---|---|---|---|---|---|---|---|---|
| 209392_at | 772 | 235 | 14 | 1088 | 210 | 243 | 912 | 9 | 8 | 8 | 7 |
| 209487_at | 291 | 148 | 21 | 315 | 280 | 1146 | 521 | 31 | 16 | 71 | 61 |
| 221653_x_at | 433 | 203 | 613 | 743 | 1224 | 5336 | 983 | 425 | 227 | 141 | 43 |
| 209185_s_at | 1935 | 1458 | 124 | 482 | 85 | 535 | 182 | 98 | 169 | 308 | 154 |
| 222809_x_at | 33 | 32 | 55 | 45 | 161 | 31 | 36 | 437 | 163 | 170 | 1483 |
| 223363_at | 161 | 136 | 139 | 92 | 156 | 129 | 114 | 241 | 122 | 147 | 105 |
| 208456_s_at | 20 | 27 | 27 | 21 | 49 | 57 | 8 | 33 | 39 | 210 | 46 |
| 221449_s_at | 7 | 7 | 28 | 54 | 30 | 50 | 199 | 185 | 57 | 24 | 156 |
| 215268_at | 9 | 11 | 157 | 41 | 17 | 11 | 42 | 11 | 27 | 9 | 9 |
| 217188_s_at | 8 | 8 | 94 | 11 | 148 | 39 | 8 | 1146 | 455 | 62 | 107 |
| 236972_at | 1318 | 1977 | 6 | 137 | 77 | 247 | 51 | 8 | 31 | 6 | 13 |

TABLE 20

| gene | lentigo maligna DF629-LM | lentigo maligna DF630-LM | lentigo maligna DF631-LM | lentigo maligna DF632-LM | lentigo maligna DT017-LM | lentigo maligna DT266-LM | lentigo maligna DT268-LM | lentigo maligna DT269-LM | lentigo maligna DT270-LM | lentigo maligna DT331-LM | lentigo maligna DT355-LM | lentigo maligna DT423-LM |
|---|---|---|---|---|---|---|---|---|---|---|---|---|
| 200961_at | 350 | 139 | 465 | 196 | 510 | 439 | 435 | 383 | 744 | 306 | 398 | 420 |
| 200782_at | 291 | 156 | 265 | 8 | 551 | 52 | 255 | 33 | 825 | 469 | 1914 | 308 |
| 206427_s_at | 2834 | 317 | 1121 | 5 | 4173 | 290 | 1952 | 181 | 3873 | 3913 | 9382 | 990 |
| 217998_at | 307 | 241 | 427 | 38 | 521 | 285 | 328 | 48 | 1470 | 344 | 879 | 184 |
| 226602_s_at | 114 | 46 | 230 | 74 | 48 | 184 | 81 | 280 | 13 | 46 | 30 | 107 |
| 240366_at | 6 | 6 | 6 | 6 | 6 | 43 | 8 | 8 | 115 | 262 | 642 | 47 |
| 208325_s_at | 529 | 101 | 448 | 1404 | 956 | 506 | 782 | 632 | 608 | 2658 | 396 | 642 |
| 225202_at | 139 | 152 | 36 | 66 | 143 | 121 | 83 | 46 | 1987 | 65 | 23 | 31 |
| 225946_at | 6 | 6 | 81 | 6 | 28 | 14 | 32 | 9 | 415 | 46 | 202 | 67 |
| 1553603_s_at | 34 | 40 | 21 | 32 | 52 | 13 | 37 | 37 | 22 | 56 | 11 | 37 |
| 220625_s_at | 5 | 6 | 69 | 95 | 11 | 23 | 33 | 90 | 5 | 6 | 6 | 239 |
| 229982_at | 36 | 14 | 56 | 47 | 29 | 13 | 21 | 13 | 12 | 13 | 12 | 12 |
| 1552283_s_at | 13 | 12 | 10 | 10 | 16 | 10 | 13 | 9 | 38 | 26 | 34 | 13 |
| 200723_s_at | 321 | 300 | 70 | 118 | 138 | 68 | 21 | 54 | 80 | 97 | 67 | 113 |
| 209174_s_at | 84 | 52 | 12 | 40 | 38 | 26 | 84 | 70 | 28 | 47 | 63 | 29 |
| 233599_at | 296 | 32 | 96 | 80 | 1338 | 115 | 314 | 86 | 131 | 497 | 62 | 235 |
| 201739_at | 2421 | 3869 | 4568 | 3885 | 2679 | 4995 | 4927 | 4514 | 12929 | 5385 | 9033 | 5005 |
| 209392_at | 273 | 223 | 464 | 11 | 656 | 26 | 498 | 7 | 1581 | 287 | 2683 | 238 |
| 209487_at | 101 | 6 | 338 | 6 | 661 | 19 | 36 | 6 | 366 | 33 | 243 | 90 |
| 221653_x_at | 626 | 873 | 983 | 336 | 1599 | 265 | 780 | 493 | 516 | 1548 | 1540 | 437 |
| 209185_s_at | 389 | 115 | 164 | 214 | 105 | 201 | 102 | 255 | 1272 | 161 | 139 | 160 |
| 222809_x_at | 166 | 105 | 461 | 83 | 125 | 527 | 435 | 453 | 22 | 186 | 56 | 322 |
| 223363_at | 314 | 122 | 132 | 90 | 191 | 105 | 206 | 373 | 167 | 113 | 167 | 104 |
| 208456_s_at | 17 | 26 | 122 | 27 | 44 | 203 | 61 | 36 | 71 | 22 | 27 | 196 |
| 221449_s_at | 36 | 171 | 107 | 142 | 39 | 74 | 48 | 83 | 11 | 10 | 40 | 162 |
| 215268_at | 11 | 7 | 9 | 9 | 43 | 11 | 24 | 16 | 8 | 11 | 11 | 98 |
| 217188_s_at | 175 | 638 | 24 | 79 | 138 | 166 | 95 | 50 | 8 | 144 | 25 | 84 |
| 236972_at | 33 | 34 | 328 | 7 | 365 | 41 | 51 | 9 | 1766 | 698 | 421 | 200 |

TABLE 21

| gene | lentigo maligna DT425-LM | lentigo maligna DT461-LM | lentigo maligna DF523-LM |
|---|---|---|---|
| 200961_at | 798 | 348 | 7 |
| 200782_at | 150 | 328 | 502 |
| 206427_s_at | 177 | 778 | 909 |
| 217998_at | 38 | 233 | 135 |
| 226602_s_at | 492 | 49 | 46 |
| 240366_at | 6 | 9 | 6 |
| 208325_s_at | 20 | 38 | 49 |
| 225202_at | 68 | 9 | 9 |
| 225946_at | 5 | 6 | 6 |
| 1553603_s_at | 168 | 21 | 22 |
| 220625_s_at | 204 | 6 | 76 |
| 229982_at | 58 | 62 | 25 |
| 1552283_s_at | 13 | 18 | 10 |
| 200723_s_at | 863 | 24 | 335 |
| 209174_s_at | 49 | 12 | 12 |
| 233599_at | 93 | 53 | 238 |
| 201739_at | 2997 | 4238 | 5786 |
| 209392_at | 20 | 9 | 10 |
| 209487_at | 6 | 6 | 6 |
| 221653_x_at | 750 | 1089 | 728 |
| 209185_s_at | 273 | 7 | 6 |
| 222809_x_at | 111 | 35 | 188 |
| 223363_at | 107 | 83 | 102 |
| 208456_s_at | 22 | 10 | 40 |
| 221449_s_at | 22 | 22 | 51 |
| 215268_at | 6 | 6 | 13 |
| 217188_s_at | 38 | 6 | 63 |
| 236972_at | 8 | 7 | 13 |

Although the invention has been described with reference to the above examples, it will be understood that modifications and variations are encompassed within the spirit and scope of the invention. Accordingly, the invention is limited only by the following claims.

What is claimed is:

1. A method of detecting melanoma in a human subject comprising:
   (a) obtaining a sample of a skin lesion suspected of comprising melanoma from a human subject, wherein the skin lesion sample comprises or is suspected of comprising a nucleic acid molecule expressed from C6orf218;
   (b) detecting the presence of a nucleic acid molecule expressed from C6orf218 in the skin lesion sample, whereby the presence of a nucleic acid molecule expressed from C6orf218 in the skin lesion sample in an amount that is greater than the presence of C6orf218 in a non-melanoma sample is indicative of melanoma in the skin lesion sample, wherein detecting the presence of a nucleic acid molecule expressed from C6orf218 is by application of a detectably labeled probe that hybridizes to a nucleic acid molecule expressed from C6orf218; and
   (c) characterizing the skin lesion as having melanoma or not having melanoma.

2. The method of claim 1, wherein the nucleic acid molecule is RNA.

3. The method of claim 1, further comprising amplifying the nucleic acid molecule.

4. The method of claim 1, wherein the nucleic acid molecule or an amplification product thereof, is quantified using quantitative real-time PCR.

5. The method of claim 1, further comprising amplifying the nucleic acid molecule and quantifying the amplification product using quantitative real-time PCR.

6. The method of claim 1, wherein the skin lesion sample is obtained by applying an adhesive tape to a target area of skin in a manner sufficient to isolate the skin lesion sample adhering to the adhesive tape.

7. The method of claim 1, wherein the skin lesion sample is obtained from a biopsy taken at the site of the skin lesion.

8. The method of claim 6, wherein the tape comprises a rubber adhesive on a polyurethane film.

9. The method of claim 6, wherein about one to ten adhesive tapes or one to ten applications of a tape are applied and removed from the skin.

10. The method of claim 6, wherein about one to eight adhesive tapes or one to eight applications of a tape are applied and removed from the skin.

11. The method of claim 6, wherein about one to five adhesive tapes or one to five applications of a tape are applied and removed from the skin.

12. The method of claim 6, wherein the method further comprises taking a biopsy of the target area of the skin.

13. The method of claim 1, wherein the detecting is performed in situ.

14. The method of claim 1, further comprising determining a treatment regimen.

15. A method for diagnosing melanoma in a subject, comprising:
   (a) obtaining a sample of a skin lesion suspected of comprising melanoma from a subject, wherein the skin lesion sample comprises or is suspected of comprising a nucleic acid molecule expressed from C6orf218;
   (b) detecting the presence of a nucleic acid molecule expressed from C6orf218 in the skin lesion sample, wherein detecting the presence of a nucleic acid molecule expressed from C6orf218 is by application of a detectably labeled probe that hybridizes to a nucleic acid molecule expressed from C6orf218; and
   (c) comparing the presence of a nucleic acid molecule expressed from C6orf218 in the skin lesion sample to the presence of C6orf218 in a non-melanoma sample, whereby the increased presence of a nucleic acid molecule expressed from C6orf218 in the skin lesion sample as compared to the non-melanoma sample is indicative of melanoma, thereby diagnosing the skin lesion as having melanoma.

16. The method of claim 15, further comprising determining a treatment regimen.

17. The method of claim 15, wherein the presence of a nucleic acid molecule expressed from C6orf218 in the non-melanoma skin sample is contained with a database.

18. The method of claim 15, wherein the analyzing step is carried out using a computer.

* * * * *

UNITED STATES PATENT AND TRADEMARK OFFICE
CERTIFICATE OF CORRECTION

Page 1 of 1

PATENT NO. : 9,057,109 B2
APPLICATION NO. : 14/199900
DATED : June 16, 2015
INVENTOR(S) : Sherman H. Chang It is certified that error appears in the above-identified patent and that said Letters Patent is hereby corrected as shown below:

In the Specification

In Column 1, at Line 14, "U.S. Application Ser. No. 61/053,998 filed May 16, 2008" should read -- U.S. Application Ser. No. 61/053,988 filed May 16, 2008 --

Signed and Sealed this
Twentieth Day of April, 2021

Drew Hirshfeld
*Performing the Functions and Duties of the
Under Secretary of Commerce for Intellectual Property and
Director of the United States Patent and Trademark Office*